US011957353B2

(12) United States Patent
Shelton, IV et al.

(10) Patent No.: US 11,957,353 B2
(45) Date of Patent: Apr. 16, 2024

(54) IMPLANTABLE SPHINCTER ASSISTANCE DEVICE WITH REDIRECTED OR FOCUSED MAGNETIC FIELDS FOR INTERACTION BETWEEN ADJACENT BEADS

(71) Applicant: Cilag GmbH International, Zug (CH)

(72) Inventors: Frederick E. Shelton, IV, Hillsboro, OH (US); Kevin M. Fiebig, Cincinnati, OH (US); Glenn W. Ellison, Maineville, OH (US); Tylor C. Muhlenkamp, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 20 days.

(21) Appl. No.: 17/552,506

(22) Filed: Dec. 16, 2021

(65) Prior Publication Data

US 2023/0190284 A1  Jun. 22, 2023

(51) Int. Cl.
*A61B 17/12* (2006.01)
*A61B 17/00* (2006.01)

(52) U.S. Cl.
CPC ............ *A61B 17/12013* (2013.01); *A61B 2017/00876* (2013.01)

(58) Field of Classification Search
CPC ........ A61B 17/12009; A61B 17/12099; A61B 17/12013; A61B 17/12036; A61B 17/12109; A61B 2017/00818; A61B 2017/00827; A61B 2017/00876; A61B 2017/00526; A61B 2017/00411; A61B 2018/00553; A61B 2050/0063; A61B 2050/0067; A61B 2050/0068;
(Continued)

(56) References Cited

U.S. PATENT DOCUMENTS 7,175,589 B2   2/2007   Deem et al.
7,695,427 B2   4/2010   Kugler et al.
(Continued)

FOREIGN PATENT DOCUMENTS

DE   3011742 A1   10/1981
EP   2182885 B1   3/2015

OTHER PUBLICATIONS

U.S. Appl. No. 17/552,469.
(Continued)

*Primary Examiner* — Jocelin C Tanner
(74) *Attorney, Agent, or Firm* — Frost Brown Todd LLP

(57) ABSTRACT

An apparatus includes at least one link and a plurality of beads. The plurality of beads is joined using the at least one link and is configured to be arranged in an annular arrangement. The annular arrangement is sized and configured to form a loop around an anatomical structure in a patient. The annular arrangement is configured to move between a contracted configuration and an expanded configuration. The loop in the contracted configuration is configured to prevent fluid flow through the anatomical structure. Each bead includes a housing, a magnet contained within the housing, and a secondary element that is different from the magnet. The magnet is configured to emit a magnetic field. The magnets of the plurality of beads are configured to magnetically bias the loop toward the contracted configuration. The secondary element is contained within the housing and is configured to increase the magnetic field of the magnet.

18 Claims, 37 Drawing Sheets

(58) Field of Classification Search
CPC .... A61B 2050/0076; A61B 2050/0082; A61B 2050/0084; A61F 2/0004; A61F 2/04; A61F 2002/044; A61F 2210/009
See application file for complete search history.

(56) References Cited

U.S. PATENT DOCUMENTS

| | | | |
|---|---|---|---|
| 8,070,670 | B2 | 12/2011 | Deem et al. |
| 8,734,475 | B2 | 5/2014 | Ekvall et al. |
| 8,870,898 | B2 | 10/2014 | Beisel et al. |
| 10,245,133 | B2 | 4/2019 | Alharmi et al. |
| 10,405,865 | B2 | 9/2019 | Shelton, IV et al. |
| 10,517,600 | B2 | 12/2019 | Beisel et al. |
| 10,543,074 | B2 | 1/2020 | Frigstad et al. |
| 10,716,570 | B2 | 7/2020 | Shelton, IV et al. |
| 10,813,737 | B2 | 10/2020 | Auld et al. |
| 10,828,064 | B2 | 11/2020 | Flakne et al. |
| 10,842,496 | B2 | 11/2020 | Shelton, IV et al. |
| 10,945,738 | B2 | 3/2021 | Auld et al. |
| 11,071,619 | B2 | 7/2021 | Shelton, IV et al. |
| 11,076,856 | B2 | 8/2021 | Kopelman |
| 11,207,173 | B2 | 12/2021 | Popescu |
| 11,298,136 | B2 | 4/2022 | Shelton, IV et al. |
| 11,350,946 | B2 | 6/2022 | Dobashi et al. |
| 11,399,928 | B2 | 8/2022 | Shelton, IV et al. |
| 11,478,347 | B2 | 10/2022 | Fiebig et al. |
| 2005/0197715 | A1 | 9/2005 | Kugler et al. |
| 2011/0098731 | A1 | 4/2011 | Whitbrook et al. |
| 2014/0088342 | A1 | 3/2014 | Djurovic |
| 2017/0112650 | A1 | 4/2017 | Hingston et al. |
| 2019/0274687 | A1 | 9/2019 | Wang et al. |
| 2020/0187949 | A1* | 6/2020 | Shelton, IV ....... A61B 17/1204 |
| 2023/0190277 | A1 | 6/2023 | Shelton, IV et al. |
| 2023/0190278 | A1 | 6/2023 | Shelton, IV et al. |
| 2023/0190279 | A1 | 6/2023 | Shelton, IV et al. |
| 2023/0190280 | A1 | 6/2023 | Shelton, IV et al. |
| 2023/0190283 | A1 | 6/2023 | Shelton, IV et al. |

OTHER PUBLICATIONS

U.S. Appl. No. 17/552,474.
U.S. Appl. No. 17/552,477.
U.S. Appl. No. 17/552,481.
U.S. Appl. No. 17/552,483.
U.S. Appl. No. 17/552,485.
U.S. Appl. No. 17/552,488.
U.S. Appl. No. 17/552,494.
U.S. Appl. No. 17/552,780.
U.S. Appl. No. 17/552,793.
U.S. Appl. No. 17/552,800.
U.S. Appl. No. 17/552,810.
U.S. Appl. No. 17/552,796.
U.S. Appl. No. 17/552,502.
U.S. Appl. No. 17/552,503.
U.S. Appl. No. 17/552,508.
U.S. Appl. No. 17/552,510.
U.S. Appl. No. 17/552,514.
U.S. Appl. No. 17/552,520.
U.S. Appl. No. 17/552,522.

* cited by examiner

IMPLANTABLE SPHINCTER ASSISTANCE DEVICE WITH REDIRECTED OR FOCUSED MAGNETIC FIELDS FOR INTERACTION BETWEEN ADJACENT BEADS

BACKGROUND

In some instances, it may be desirable to place a medical implant within or surrounding a biological lumen/passageway in order to improve or assist the function of, or otherwise affect, the biological lumen/passageway. Examples of such biological lumens/passageways include, but are not limited to, the esophagus, a fallopian tube, a urethra, or a blood vessel. Some biological passages normally function by expanding and contracting actively or passively to regulate the flow of solids, liquids, gasses, or a combination thereof. The ability of a biological passage to expand and contract may be compromised by defects or disease. One merely illustrative example of a condition associated with decreased functionality of a body passage is Gastro Esophageal Reflux Disease ("GERD"), which effects the esophagus.

A normal, healthy, esophagus is a muscular tube that carries food from the mouth, through the chest cavity and into the upper part of the stomach. A small-valved opening in the esophagus, called the lower esophageal sphincter ("LES"), regulates the passage of food from the esophagus into the stomach, as well as the passage of acidic fluids and food from the stomach toward the esophagus. The LES may also regulate stomach intra-gastric pressures. A healthy LES may contain pressure of gasses within the stomach at around 10 mm Hg greater than normal intragastrical pressure, thereby impeding acidic gases/fluids from refluxing from the stomach back into the esophagus. When functioning properly, a pressure difference greater than 10 mm Hg may regulate when the LES opens to allow gasses to be vented from the stomach toward the esophagus.

If the LES relaxes, atrophies, or degrades for any reason, the LES may cease functioning properly. Therefore, the LES may fail to sufficiently contain pressure of gasses within the stomach such that acidic contents of the stomach may travel back into the esophagus, resulting in reflux symptoms. Two primary components that control the LES are the intrinsic smooth muscle of the distal esophagus wall and the skeletal muscle of the crural diaphragm or esophageal hiatus. A causation of esophageal reflux, which may be associated with GERD, is relaxation of one or both of the smooth muscle of the distal esophagus wall or the hiatal diaphragm sphincter mechanisms. Chronic or excessive acid reflux exposure may cause esophageal damage. Conventionally, treatment for GERD may involve either open or endoscopic surgical procedures. Some procedures may include a fundoplication that mobilizes the stomach relative to the lower esophagus; or suturing a pleat of tissue between the LES and the stomach to make the lower esophagus tighter.

Examples of devices and methods that have been developed to treat anatomical lumens by providing sphincter augmentation are described in U.S. Pat. No. 7,175,589, entitled "Methods and Devices for Luminal and Sphincter Augmentation," issued Feb. 13, 2007, the disclosure of which is incorporated by reference herein, in its entirety; U.S. Pat. No. 7,695,427, entitled "Methods and Apparatus for Treating Body Tissue Sphincters and the Like," issued Apr. 13, 2010, the disclosure of which is incorporated by reference herein, in its entirety; U.S. Pat. No. 8,070,670, entitled "Methods and Devices for Luminal and Sphincter Augmentation," issued Dec. 6, 2011, the disclosure of which is incorporated by reference herein, in its entirety; and U.S. Pat. No. 8,734,475, entitled "Medical Implant with Floating Magnets," issued May 27, 2014, the disclosure of which is incorporated by reference herein, in its entirety.

While various kinds and types of instruments have been made and used to treat or otherwise engage anatomical lumens, it is believed that no one prior to the inventors has made or used an invention as described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
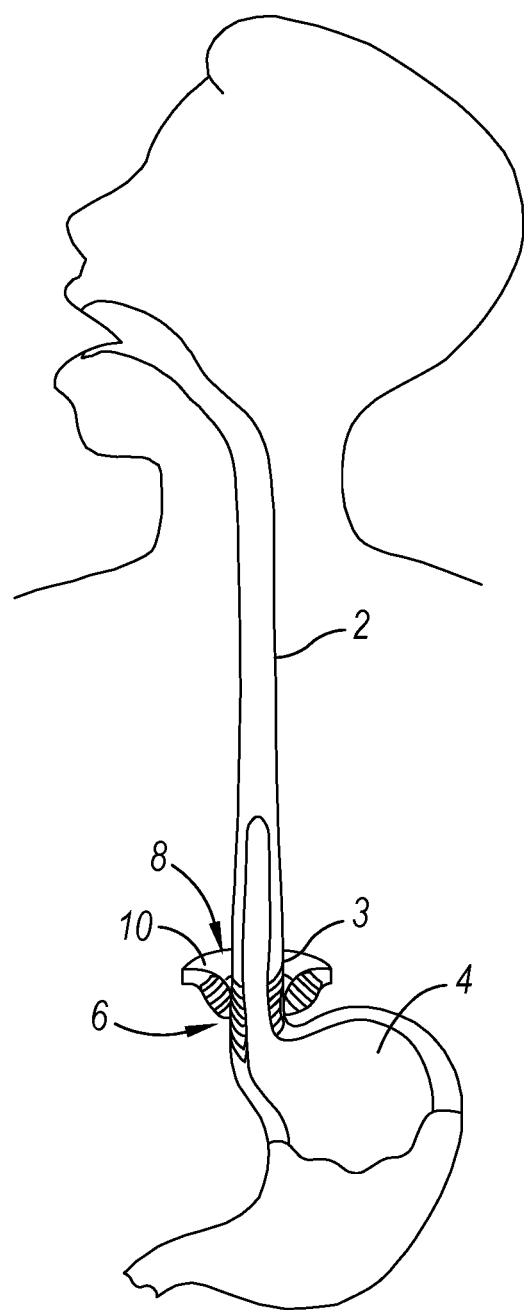
FIG. 1 depicts a cross-sectional side view, taken along a coronal plane of the body, of a biological passage.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. OVERVIEW OF EXAMPLE OF SPHINCTER AUGMENTATION DEVICE

Figure 2:
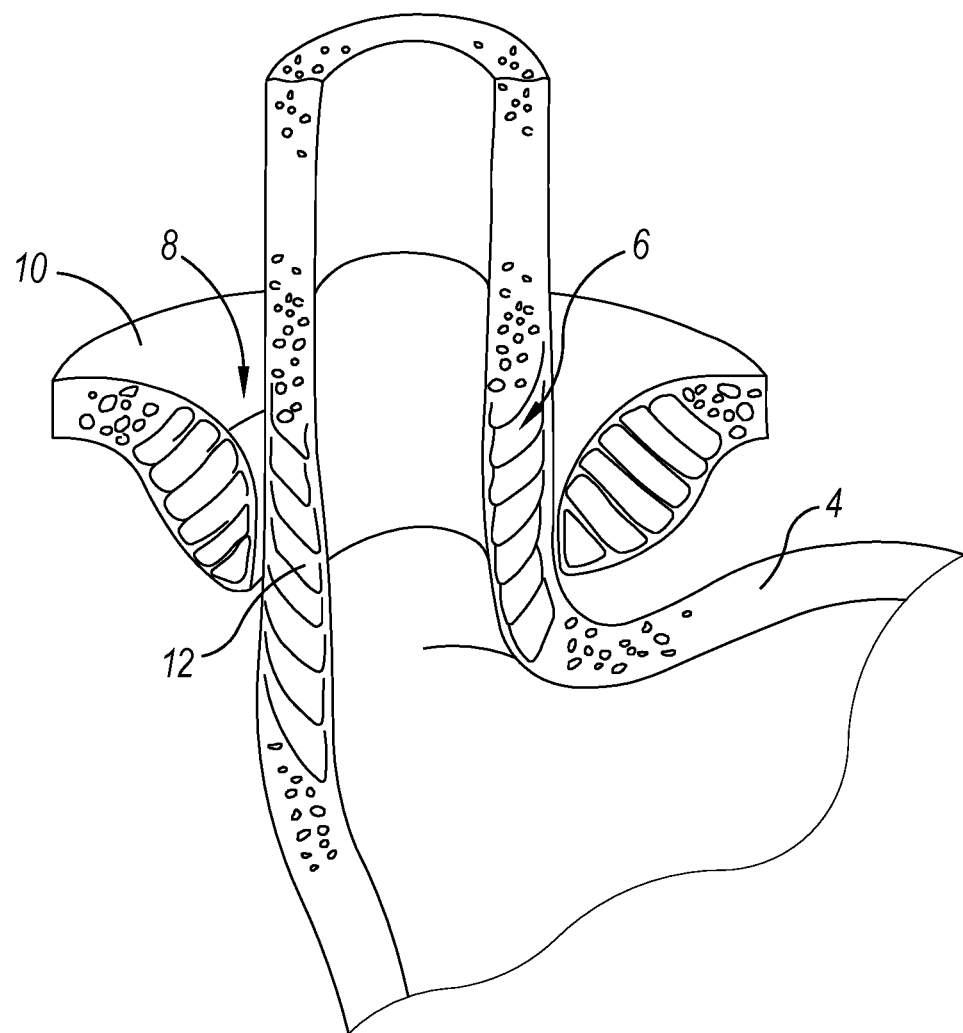
FIG. 2 depicts a cross-sectional isometric view, taken along a coronal plane of the body, of a human esophago-gastric junction.
Figure 3:
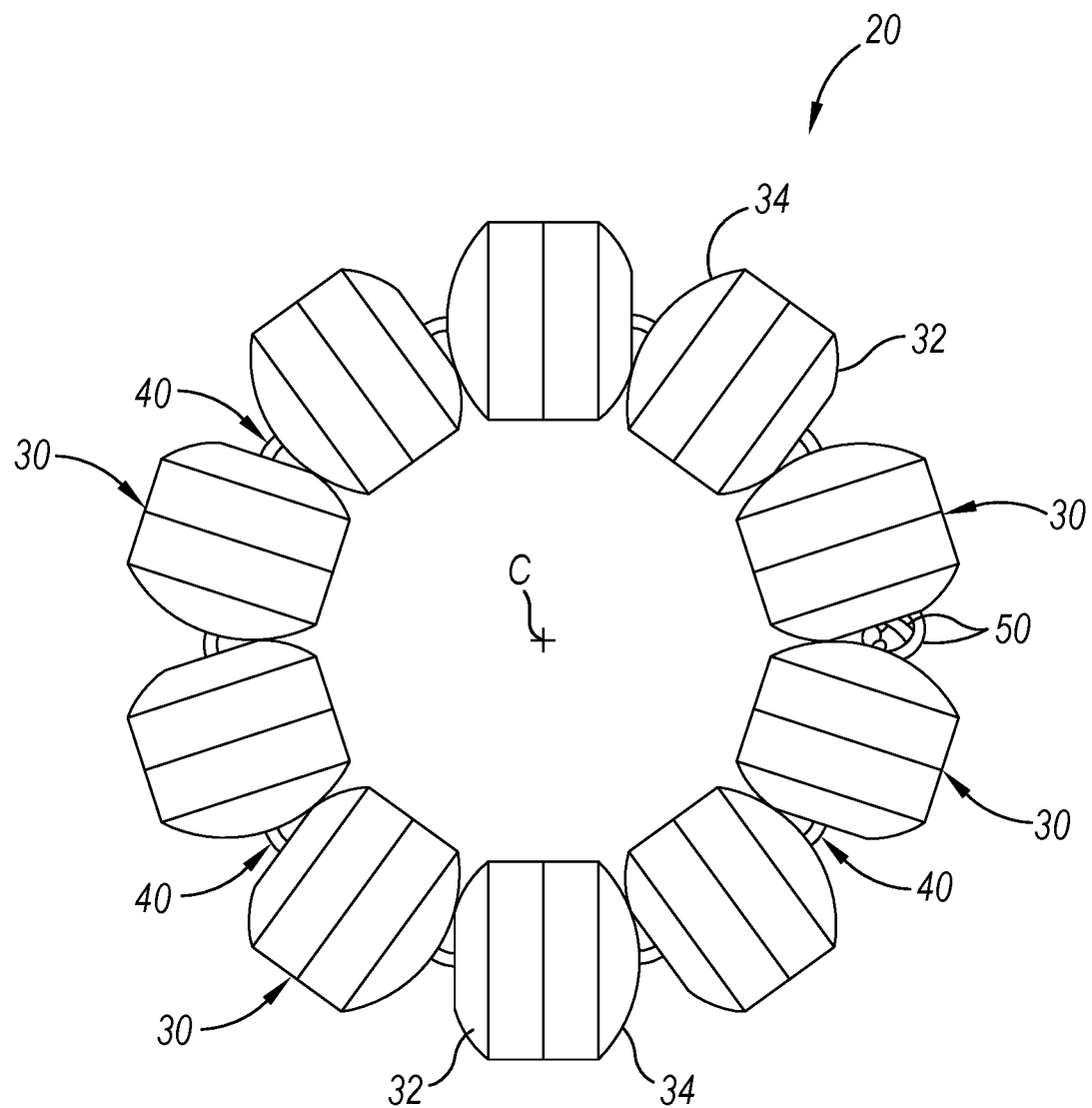
FIG. 3 depicts a top plan view of an example of a sphincter augmentation device.

FIGS. 1-2 show selected portions of human anatomy, which includes an esophagus (2) extending from the mouth, through a hiatus (8) defined by a diaphragm (10), and into a stomach (4). Esophagus (2) also includes a distal esophagus (3) and an LES (6). LES (6) is located along distal esophagus (3) adjacent to the junction of esophagus (2) and stomach (4). The portion of LES (6) extending through hiatus (8) is supported by diaphragm (10). When functioning properly, LES (6) is configured to transition between an occluded state and an opened state (as shown in FIG. 2). As best seen in FIG. 2, LES (6) includes a plurality of sling fibers (12). Sling fibers (12) are smooth muscle tissue that may help regulate LES (6) transition between the occluded state and the open state. Hiatus (8) of diaphragm (10) may also help LES (6) transition between the occluded state and the open state.

A healthy LES (6) transitions between the occluded state and the opened state to act as a valve. In other words, a healthy LES (6) may transition from the occluded state to the opened state to allow solids, liquids, and/or gasses to selectively travel between esophagus (2) and stomach (4). For example, a healthy LES (6) may transition from the occluded state to the opened state to permit a bolus of food to travel from esophagus (2) into stomach (4) during peristalsis; or to vent intra-gastric pressure from stomach (4) toward esophagus (2). Additionally, in the occluded state, a healthy LES (6) may prevent digesting food and acidic fluid from exiting stomach (4) back into esophagus (2).

If LES (6) ceases functioning properly by prematurely relaxing, and thereby improperly transitioning esophagus (2) from the occluded state to the opened state, undesirable consequences may occur. Examples of such undesirable consequences may include acidic reflux from stomach (4) into esophagus (2), esophageal damage, inflamed or ulcerated mucosa, hiatal hernias, other GERD symptoms, or other undesirable consequences as will be apparent to one having ordinary skill in the art in view of the teachings herein. Therefore, if an individual has an LES (6) that prematurely relaxes, causing improper transitions from the occluded state to the opened state, it may be desirable to insert an implant around a malfunctioning LES (6) such that the implant and/or LES (6) may properly transition between the occluded state and the opened state.

Figure 4:
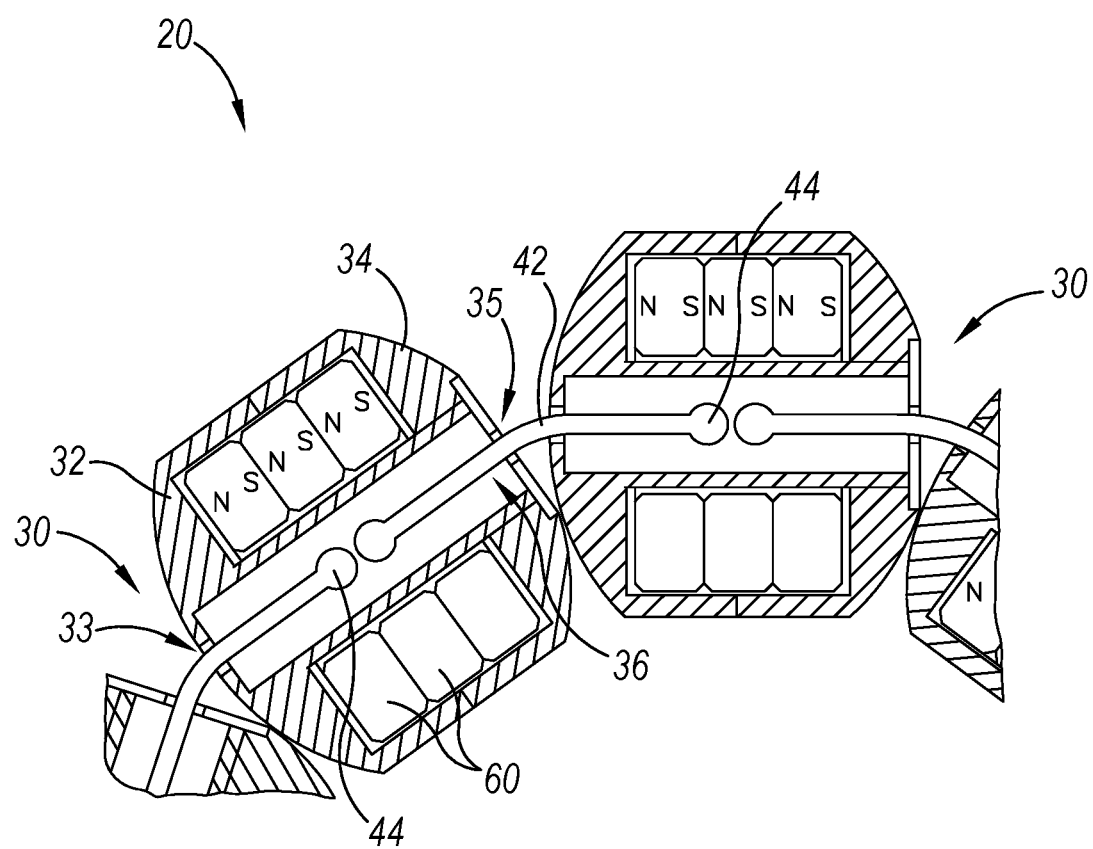
FIG. 4 depicts a partial, cross-sectional view of a portion of the sphincter augmentation device of FIG. 3.

FIGS. 3-5B show an example of a sphincter augmentation device (20) that may be used as an implant around a malfunctioning LES (6) to assist the LES (6) in transitioning between the occluded state and the opened state. Device (20) of this example comprises a plurality of beads (30) that are joined together by a plurality of links (40). Each bead (30) comprises a pair of housings (32, 34) that are securely fastened to each other. By way of example only, housings (32, 34) may be formed of a non-ferrous material (e.g., titanium, plastic, etc.). Each bead (30) further comprises a plurality of annular or toroidal rare-earth permanent magnets (60) that are stacked next to each other within housings (32, 34). In the present example, magnets (60) are completely sealed within beads (30). As best seen in FIG. 4, each bead (30) also defines a chamber (36) that is configured to receive a portion of a respective pair of links (40). Housing (32) defines an opening (33) at one end of chamber (36); while housing (34) defines an opening (35) at the other end of chamber (36).

Each link (40) of the present example comprises a wire (42) that is pre-bent to form an obtuse angle. The free end of each wire (42) terminates in a ball tip (44). Beads (30) are joined together by links (40) such that a first end portion of a link (40) is in one bead (30), a second end portion of the same link (40) is in another bead (30), and an intermediate portion of the same link (40) is positioned between those two beads (30). Chambers (36) of beads (30) are configured to freely receive ball tips (44) and adjacent regions of wires (42); while openings (33, 35) are configured to prevent ball tips (44) from exiting chambers (36). Openings (33, 35) are nevertheless sized to allow wire (42) to slide through openings (33, 35). Thus, links (40) and beads (30) are configured to allow beads (30) to slide along links (40) through a restricted range of motion.

Figure 5A:
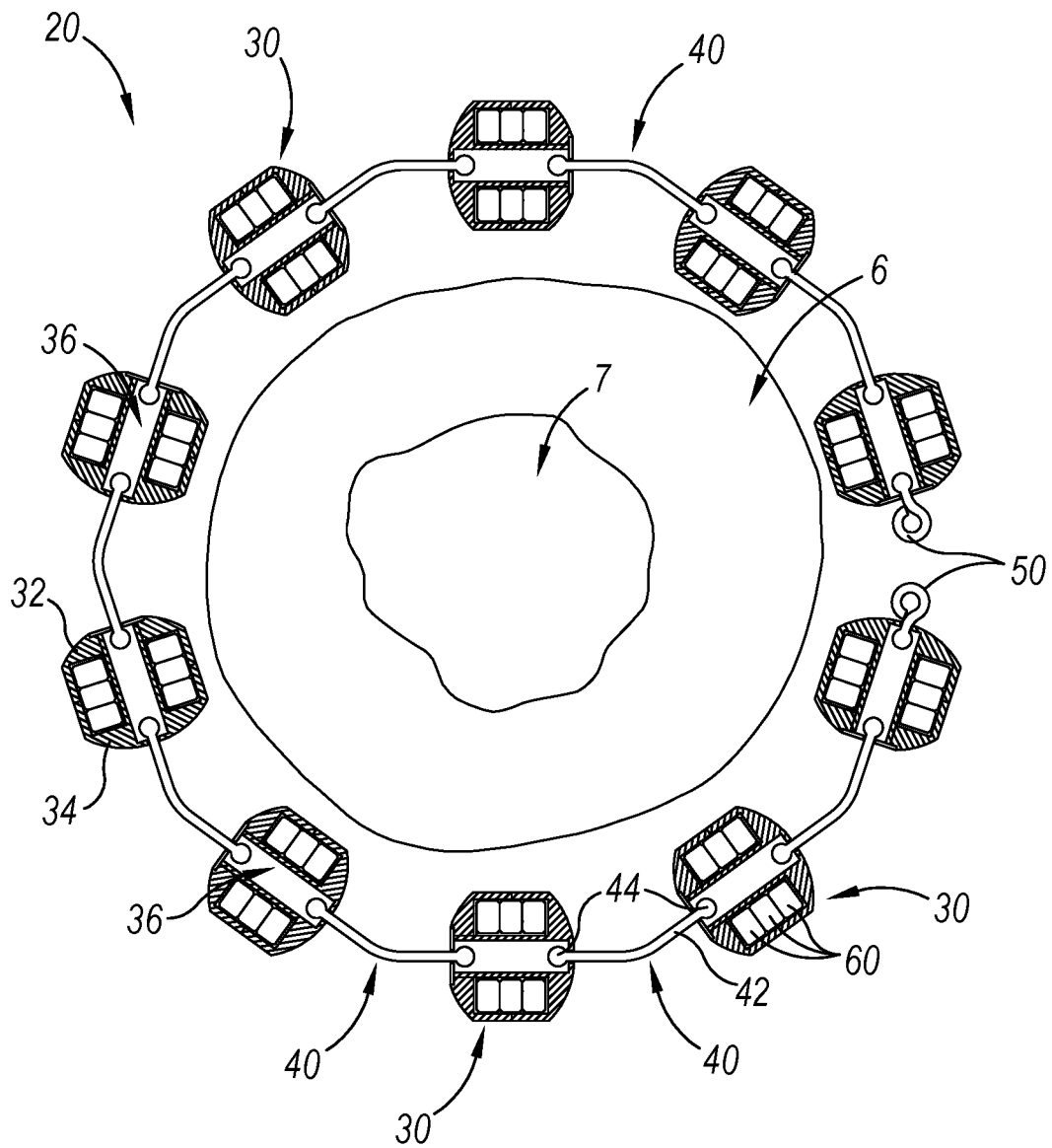
FIG. 5A depicts a top, cross-sectional view of the sphincter augmentation device of FIG. 3 positioned about an LES, with the sphincter augmentation device in an open and expanded configuration.
Figure 5B:
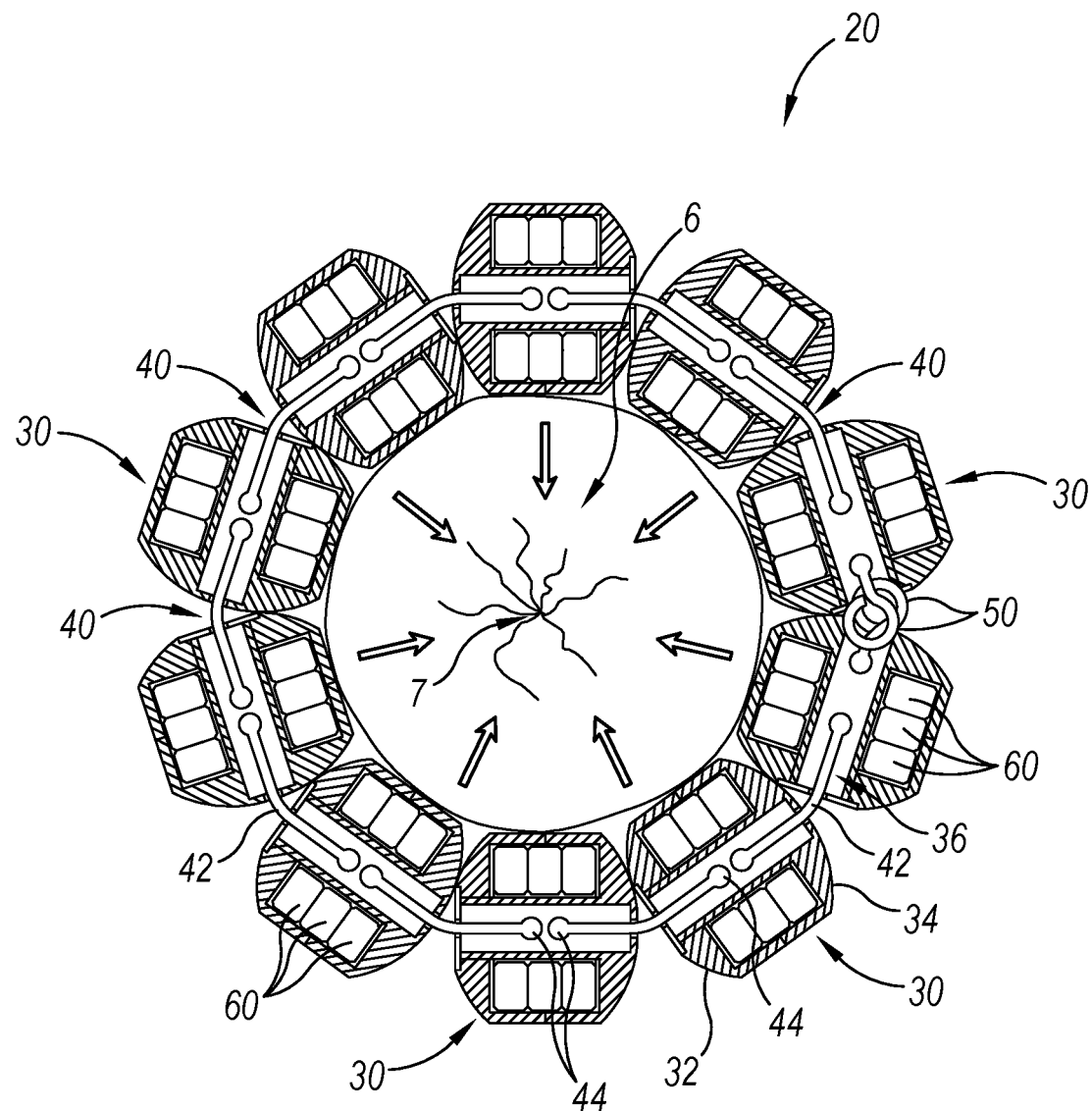
FIG. 5B depicts a top, cross-sectional view of the sphincter augmentation device of FIG. 3 positioned about the LES of FIG. 5A, with the sphincter augmentation device in a closed and contracted configuration.

As best seen in FIGS. 5A-5B, two beads (30) have opposing fastener features (50) that allow the ends of device (20) to be coupled together to form a loop. In the present example, fastener features (50) comprise eyelets. In some other versions, fastener features (50) comprise complementary clasp features. As another merely illustrative example, fastener features (50) may be configured and operable in accordance with one or more of the teachings of U.S. Pat. No. 10,405,865, entitled "Method for Assisting a Sphincter," issued Sep. 10, 2019, the disclosure of which is incorporated by reference herein, in its entirety. Other suitable ways in which the ends of device (20) may be coupled together to form a loop will be apparent to those of ordinary skill in the art in view of the teachings herein. Those of ordinary skill in the art will also recognize that it may be desirable to provide fastener features (50) that can be decoupled if it becomes necessary or otherwise warranted to remove device (20) from the patient.

FIG. 5A shows device (20) in an open, expanded state, with device (20) being positioned about LES (6). At this stage, the opening (7) defined by LES (6) is in a persistently open state (e.g., allowing the patient to undesirably experience GERD and/or other undesirable conditions), warranting the securement of device (20) about the LES (6). FIG. 5B shows device (20) secured about the LES (6), with device (20) in a closed, contracted state. Device (20) is secured closed via fastener features (50). Magnets (60) are oriented within beads (30) such that each bead (30) will be magnetically attracted to the adjacent bead (30) in device (20). In other words, beads (30) are magnetically attracted to each other to magnetically bias device (20) toward the contracted configuration shown in FIG. 5B.

With device (20) secured around the LES (6) and in the contracted configuration, device (20) deforms the LES (6) radially inwardly to substantially close the opening defined by the LES (6). In doing so, device (20) prevents the patient from experiencing GERD and/or other undesirable conditions that may be associated with a persistently open opening (7) at the LES (6). While magnets (60) have a tesla value that is high enough to substantially maintain opening (7) in a closed state to the point of preventing GERD and/or other undesirable conditions that may be associated with a persistently open opening (7), the tesla value of magnets (60) is low enough to allow LES (6) to expand radially outwardly to accommodate passage of a bolus of food, etc. through the opening (7) of LES (6). To accommodate such expansion, beads (30) may simply slide along links (40) to enlarge the effective diameter of device (20) as the bolus passes. After the bolus passes, the magnetic bias of magnets (60) will return device (20) to the contracted state shown in FIG. 5B. Device (20) thus ultimately prevents GERD and/or other undesirable conditions that may be associated with a persistently open opening (7); while still permitting the normal passage of food, etc. from the esophagus (2) to the stomach (4).

In addition to the foregoing, device (20) may be constructed and operable in accordance with at least some of the teachings of U.S. Pat. No. 7,695,427, the disclosure of which is incorporated by reference herein, in its entirety; and/or U.S. Pat. No. 10,405,865, the disclosure of which is incorporated by reference herein, in its entirety.

II. EXAMPLES OF SPHINCTER AUGMENTATION DEVICES WITH CONTROLLED HOMOGENOUS DILATION

It may be desirable for device (20) to maintain an annular arrangement in each of the expanded configuration of FIG. 5A, the contracted configuration of FIG. 5B, and positions between the expanded and the contracted configurations. However, during manufacturing, magnets (60) may be randomly placed within respective beads (30) of device (20). As a result, magnets (60) of adjacent beads (30) may pair up in various patterns due to manufacturing variation in the various components. This manufacturing variation may tend to stack up to create a cumulative variation. For example, this manufacturing variation may include differences in magnetic strength of magnets (60) and differences in the geometries of beads (30), among other manufacturing variations. This random selection of magnets (60) may cause unexpected magnetic separation forces as device (20) moves from and between the contracted configuration of FIG. 5B to the expanded configuration of FIG. 5A. For example, due to magnets (60) pairing up based on the strength of adjacent magnets, in some instances, device (20) may to provide a non-circular shaped restriction (e.g., a triangular shaped restriction).

As a result of this variability, it may be desirable to incorporate magnets (60) in beads (30) having specific magnetic force properties that collectively provide the desired effects for device (20) throughout expansion and contraction. For example, in moving from the contracted configuration to the expanded configuration, it may be beneficial that certain beads (30) of device (20) separate from each other first, before other beads (30) separate from each other, to obtain a more uniform radial expansion. Additionally, in moving from the expanded configuration to the contracted configuration, it may be beneficial that certain magnets (60) of beads (30) of device (20) attract together, before other magnets (60) of beads (30) attract together, to obtain a more uniform radial contraction. This may provide more controlled homogenous expansion and contraction of device (20).

Figure 6A:
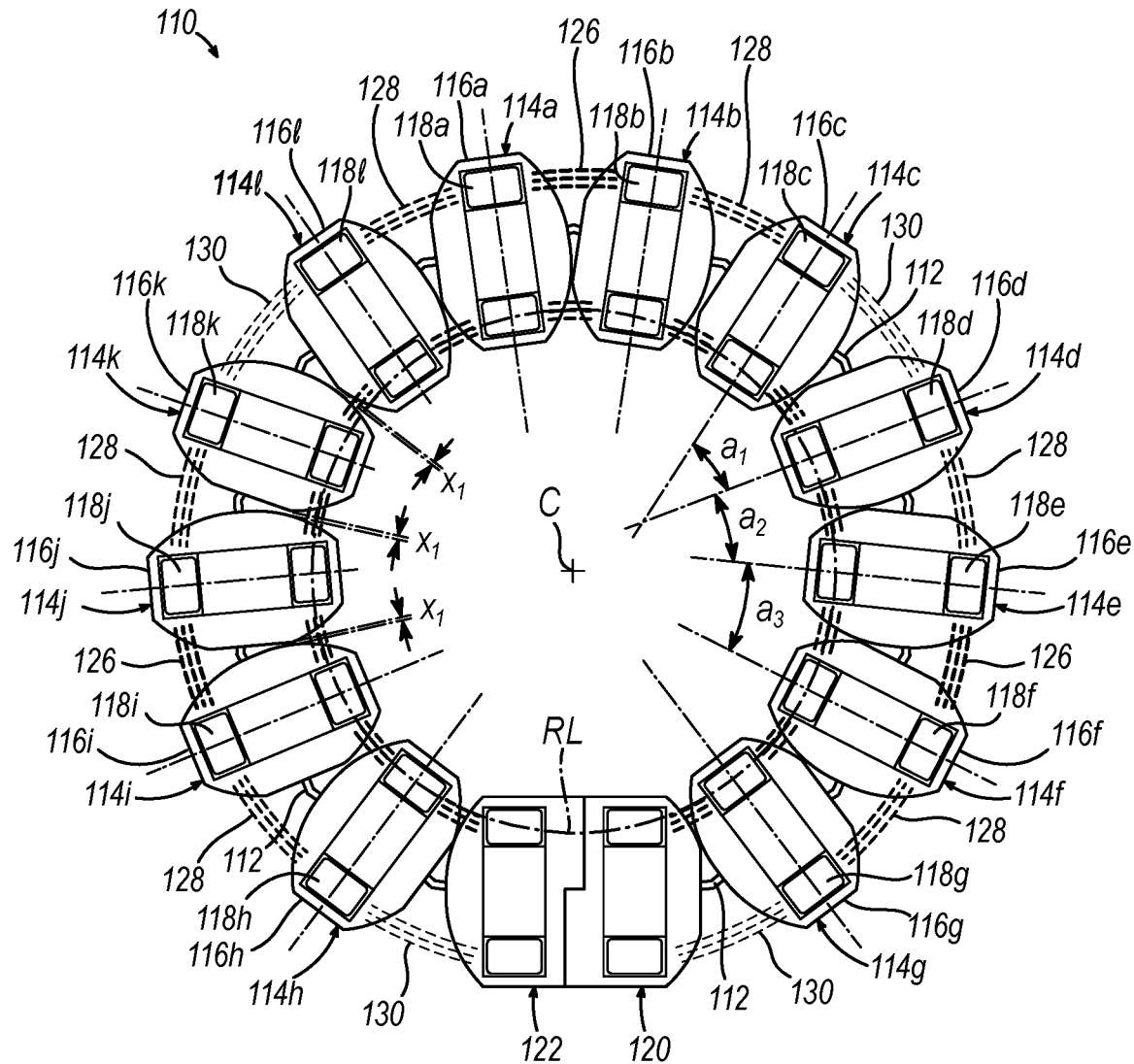
FIG. 6A depicts a top schematic plan view of a first exemplary alternative sphincter augmentation device in a closed and contracted configuration.
Figure 6B:
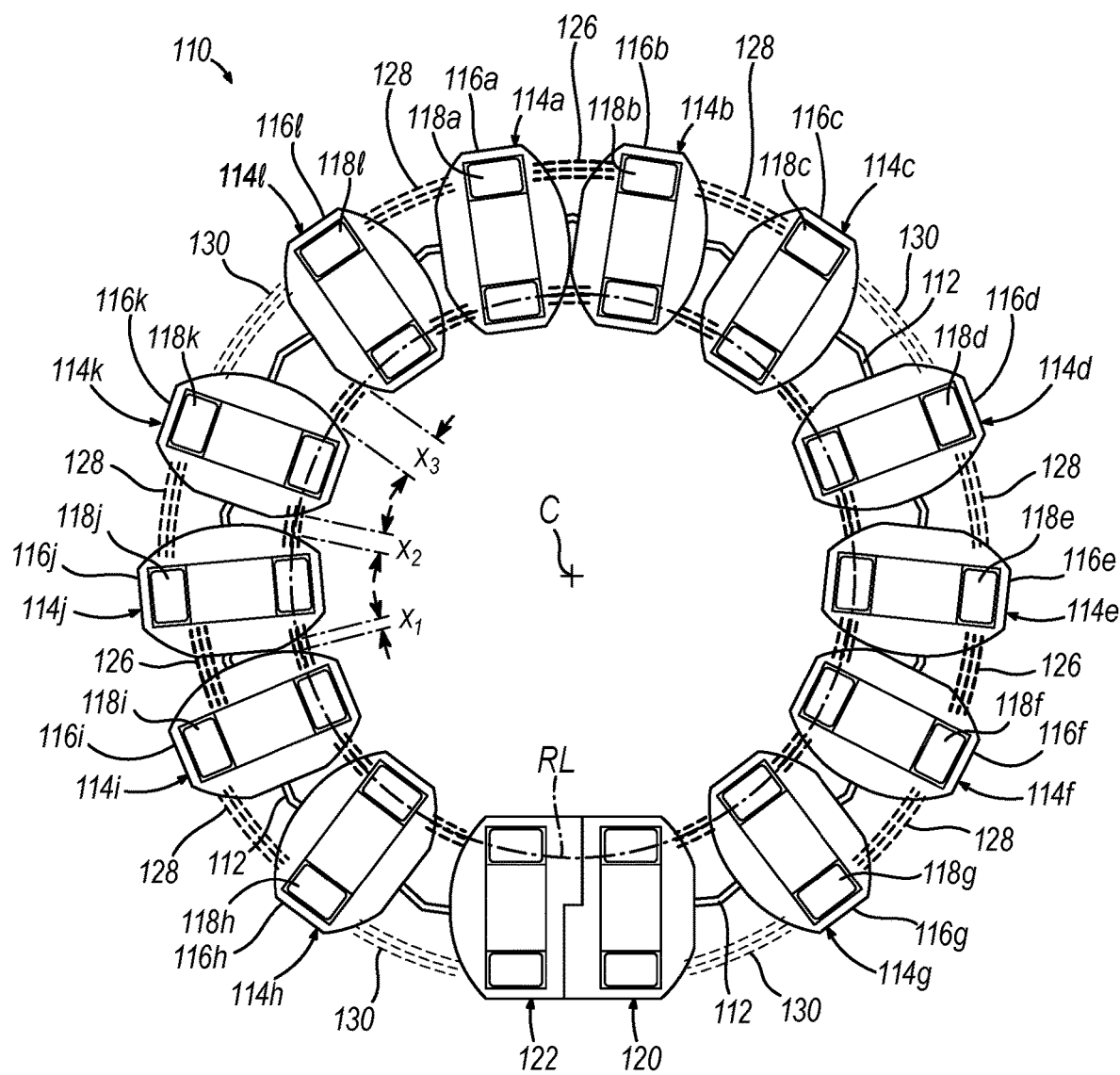
FIG. 6B depicts a top schematic plan view of the sphincter augmentation device of FIG. 6A, but in a partially closed and contracted configuration.
Figure 6C:
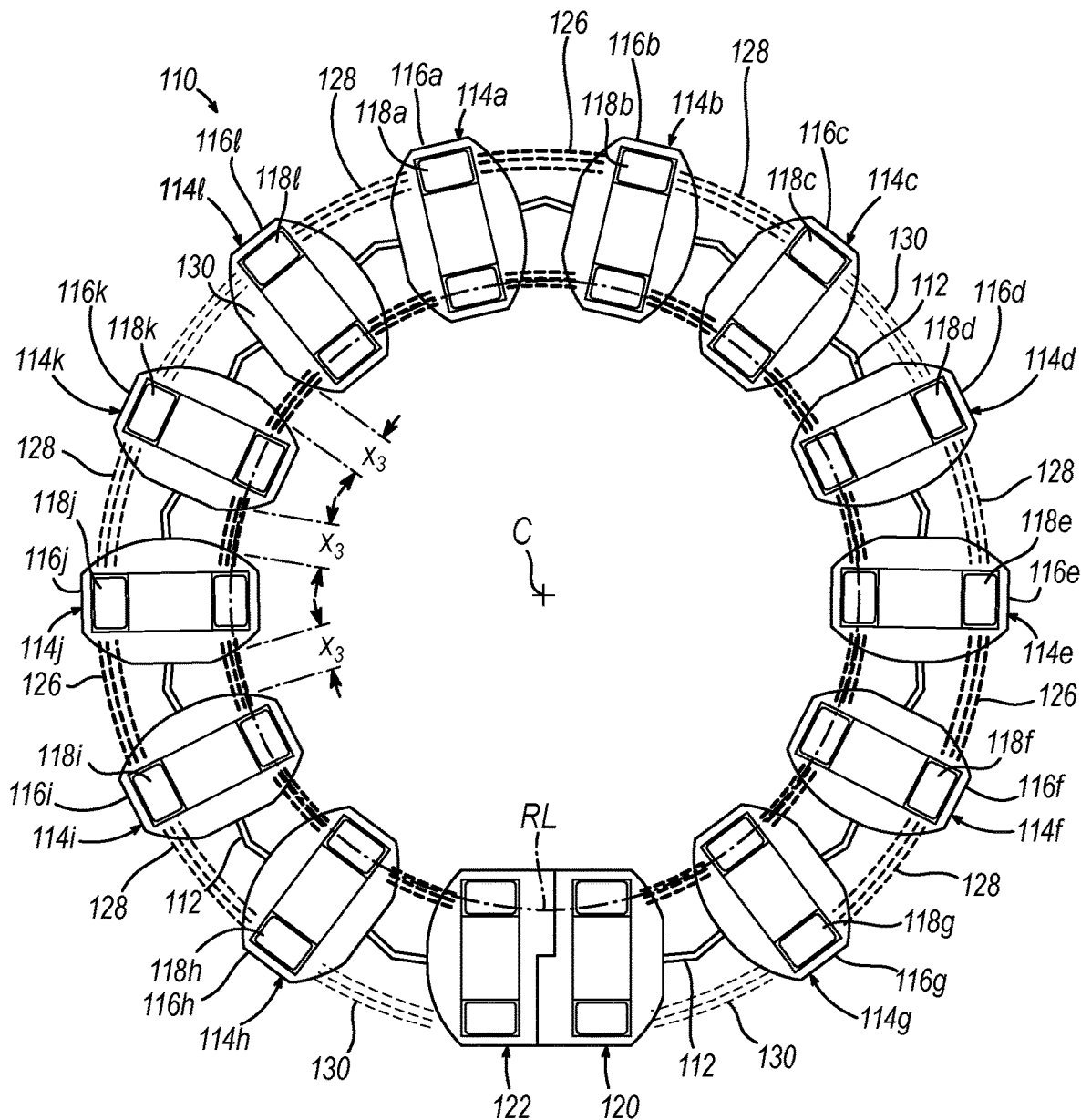
FIG. 6C depicts a top schematic plan view of the sphincter augmentation device of FIG. 6B, but in an expanded configuration.
Figure 7:
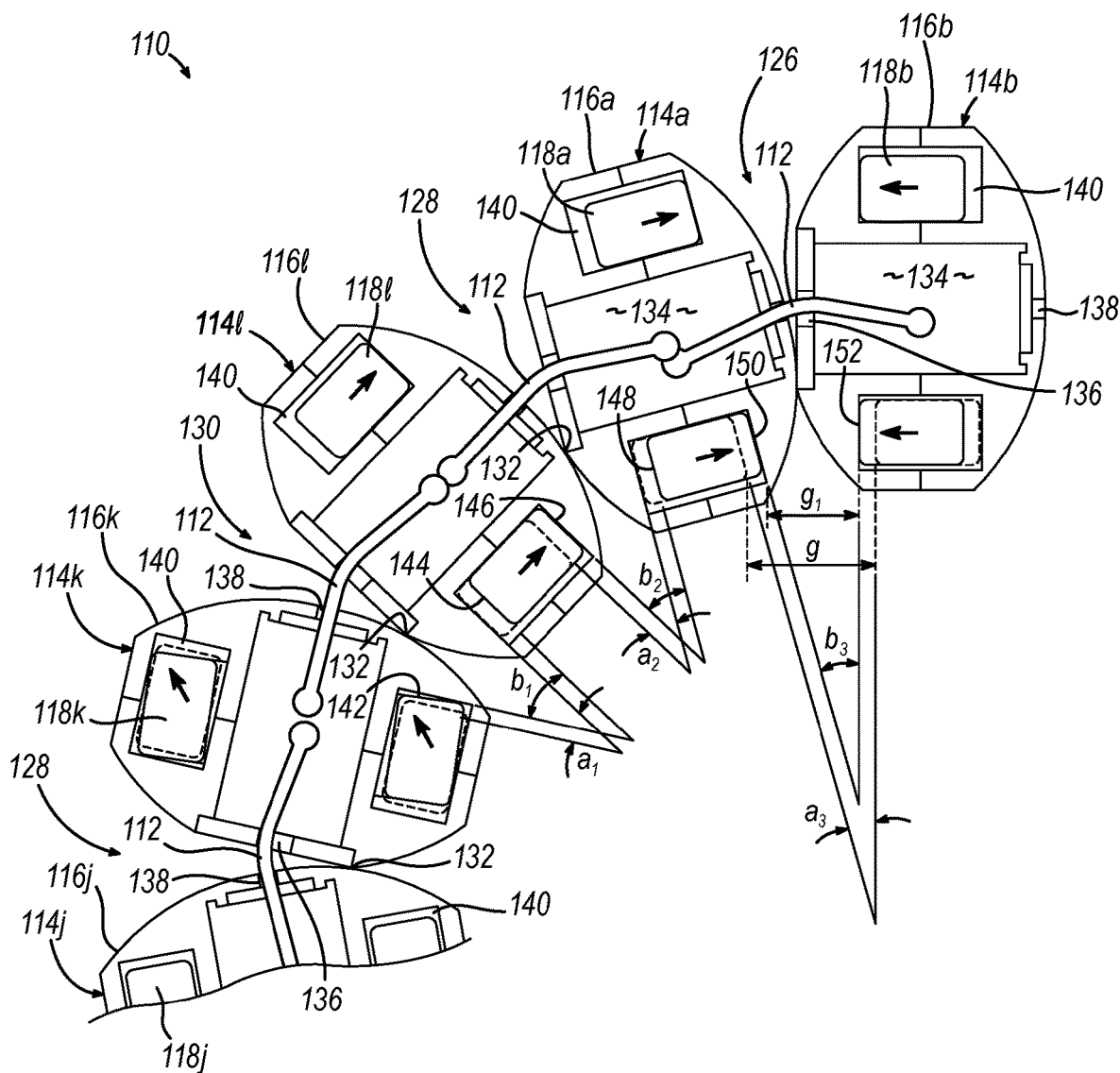
FIG. 7 depicts a partial schematic cross-sectional view of a portion of the sphincter augmentation device of FIG. 6A.

A. First Exemplary Sphincter Augmentation Device to Provide Uniform Radial Expansion and Contraction FIGS. 6A-7 show an example of an alternative sphincter augmentation device (110) that may be used in a manner similar to device (20) described above. Sphincter augmentation device (110) of this example includes at least one link (shown as a plurality of links (112)) and a plurality of beads (114a-l). Beads (114a-l) may be joined using links (112). Links (112) may be similar to links (40) and beads (114a-l) may be similar to beads (30) shown and described above with reference to FIGS. 3-4. As shown in FIGS. 6A-7, beads (114a-l) include housings (116a-l). As shown schematically in FIGS. 6A-6C, housings (116a-l) receive at least one magnet (118a-l), which may be similar to magnets (60). In some versions, each magnet (118a-l) may include one or more magnets. As shown and described in detail below, magnets (610, 710, 810, 910, 1024) may be used in place of magnets (118a-l).

Housings (116a-l) may comprise first and second housing portions (similar to housings (32, 34)). During device (110) insertion, device (110) may be positioned around LES (6), so that first and second coupling portions (120, 122) may be coupled together to form an annular arrangement. First and second coupling portions (120, 122) may utilize mechanical and/or magnetic coupling features. While first and second coupling portions (120, 122) are shown, a variety of other suitable coupling assemblies are also envisioned including those shown and described in U.S. Pat. No. 11,071,619, entitled "Coupling Assembly for Implantable Sphincter Assistance Device," issued Jul. 27, 2021, the disclosure of which is incorporated by reference herein in its entirety. In the annular arrangement, device (110) may move from the contracted configuration of FIG. 6A, through an intermediate configuration of FIG. 6B, and to the expanded configuration of FIG. 6C. Likewise, device (110) may move from the expanded configuration of FIG. 6C, through an intermediate configuration of FIG. 6B, and to the contracted configuration of FIG. 6A. The annular arrangement is sized and configured to form a loop around an anatomical structure (e.g., LES (6)) in a patient. The loop in the contracted configuration is configured to prevent fluid flow through the anatomical structure (e.g., LES (6)). The loop in the expanded configuration is configured to permit fluid flow through the anatomical structure (e.g., LES (6)). Magnets (118a-l) are configured to magnetically bias the loop toward the contracted configuration Adjacent beads (114a-l) may be magnetically attracted together at a plurality of bead-to-bead magnetic interfaces that include first, second, and third magnetic interfaces. In some versions, the first magnetic interface may include a high magnetic strength interface (126). Examples of high magnetic strength interfaces (126) are shown between beads (114a-b), between beads (114e-f), and between beads (114i-j). The second magnetic interface may include a medium magnetic strength interface (128). Examples of medium magnetic strength interfaces (128) are shown between beads (114b-c), between beads (114d-e), between beads (114f-g), between beads (114h-i), between beads (114j-k), and between beads (114a, 114l). The third magnetic interface (114c-d) may include a low magnetic strength interface (130). Examples of low magnetic strength interfaces (130) are shown between beads (114c-d), between bead (114g) and coupling portion (120), between second coupling portion (122) and bead (114h), and between beads (114k-l). As shown, high magnetic strength interfaces (126) are angularly spaced apart from each other around the annular arrangement. Similarly, medium magnetic strength interfaces (128) are angularly spaced apart from each other around the annular arrangement. Similarly, low magnetic strength interfaces (130) are angularly spaced apart from each other around the annular arrangement.

High magnetic strength interfaces (126) may have a first magnetic field strength. Medium magnetic strength interfaces (128) may have a second magnetic field strength that is less than the first magnetic field strength. Low magnetic strength interfaces (130) may have a third magnetic field strength that is less than high or medium magnetic strength interfaces (126, 128). In FIGS. 6A-6C, the thickness of the dashed lines is intended to represent the magnitude of the magnetic field, where thicker dashed lines represent stronger magnetic fields and thinner dashed lines represent weaker magnetic fields. The selective placement of high, medium, and low magnetic strength interfaces (126, 128, 130) around the annular arrangement may provide uniform radial expansion and contraction of the annular arrangement of beads (114k-l) as device (110) moves between the contracted, intermediate, and expanded configurations as well as between the expanded, intermediate, and contracted configurations. While three levels (high, medium, and low) of magnetic strength interfaces are shown in FIGS. 6A-6C, fewer levels (e.g., first and second levels) or additional levels (e.g., a fourth, fifth, sixth level, etc.) are also envisioned. Additionally, while first and second magnetic interfaces are shown and described as high and medium magnetic strength interfaces (126, 128), in other versions, the first and second magnetic interfaces may include medium and low magnetic strength interfaces or high and low magnetic strength interfaces.

When using three levels, low magnetic strength interfaces (130) are the first interfaces to separate (e.g., where beads (114a-l) spread apart) when moving from the contracted configuration of FIG. 6A to the expanded configuration of FIG. 6C; and are the last interfaces to attach when moving from the expanded configuration to the contracted configuration. Conversely, high magnetic strength interfaces (126) are the last interfaces to separate when moving from the contracted configuration to the expanded configuration; and are the first interfaces to attach when moving from the expanded configuration to the contracted configuration. Medium magnetic strength interfaces (128) separate at a time after low magnetic strength interfaces (130) but before high magnetic strength interfaces (126). Medium magnetic strength interfaces (128) attach at a time after high magnetic strength interfaces (126) but before low magnetic strength interfaces (130).

In the contracted configuration of FIG. 6A, adjacent beads (114a-l) are configured to abut each other. For example, bead (114a) is configured to abut bead (114b) at high magnetic strength interface (126). Similarly, bead (114b) is configured to abut bead (114c) at medium magnetic strength interface (128), and bead (114c) is configured to abut bead (114d) at low magnetic strength interface (130). As a result, the distance ($x_1$) between beads (114a-l) is about zero. First coupling portion (120) abuts bead (114g), and second coupling portion (122) abuts bead (114h). Changes to the interfaces between adjacent beads (124a-l) may maximize homogenous expansion between beads during device expansion. In the contracted configuration where the sphincter is closed, beads (114a-b, 114e-f, 114i-j) forming high magnetic strength interface (126) extend generally more parallel to each other. In FIGS. 6A-6C, the parallel lines along the lateral planes of the magnets show the magnetic forces. The intersection points may be located along the same radius centered at centerpoint (C) throughout the annular arrangement.

In the intermediate configuration of FIG. 6B, beads (114a-b, 114e-f, 114i-j) forming high magnetic strength interfaces (126) remain in abutting contact. As a result, the distance ($x_1$) between beads (114a-b, 114e-f, 114i-j) is about zero. Additionally, beads forming medium and low magnetic strength interfaces (128, 130) are spaced apart from one another by varying distances. As shown, in the intermediate configuration, low magnetic strength interfaces (130) are fully spaced apart and medium magnetic strength interfaces (128) are partially spaced apart. Particularly, beads forming low magnetic strength interface (130) are spaced apart by a distance ($x_3$) in the intermediate configuration which is less than a distance ($x_2$) that the beads forming medium magnetic strength interface (128) are spaced apart from each other. In the expanded configuration of FIG. 6C, adjacent beads (114a-l) are fully spaced apart. Particularly, adjacent beads (114a-l) are spaced apart a distance ($x_3$) from each other.

As shown in FIG. 7, each of housings (116a-l) of beads (114a-l) include contact surfaces (132) and a passageway (134) extending through housings (116a-l). Magnets (118a-l) are disposed around passageway (134). Each bead (114a-l) includes opposing first and second openings (136, 138). First opening (136) is configured to retain a first end of link (112) in each of the contracted and expanded configurations. Similarly, second opening (138) is configured to retain a second opposing end of another link (114) in each of the contracted and expanded configurations.

With continued reference to FIG. 7, magnets (118a-l) are received within respective magnet chambers (140) of beads (114a-l). At least one of magnet chamber (140) is sized and configured to allow for movement of magnet (118a-l) within magnet chambers (140). For example, magnets (118a-l) may shift laterally within magnet chambers (140) and/or twist within magnet chambers (140). Annular magnet (118a-l) may shift laterally based on the proximity to the adjacent bead (114a-l) and/or the magnetic strength of adjacent magnet (118a-l) disposed within adjacent bead (114a-l). This may allow the spacing between beads (114-a-l) to be adjusted by the opening and closing limits. This adjustment of magnet location affects the magnetic field interaction between adjacent beads (114-a-l).

Figure 8:
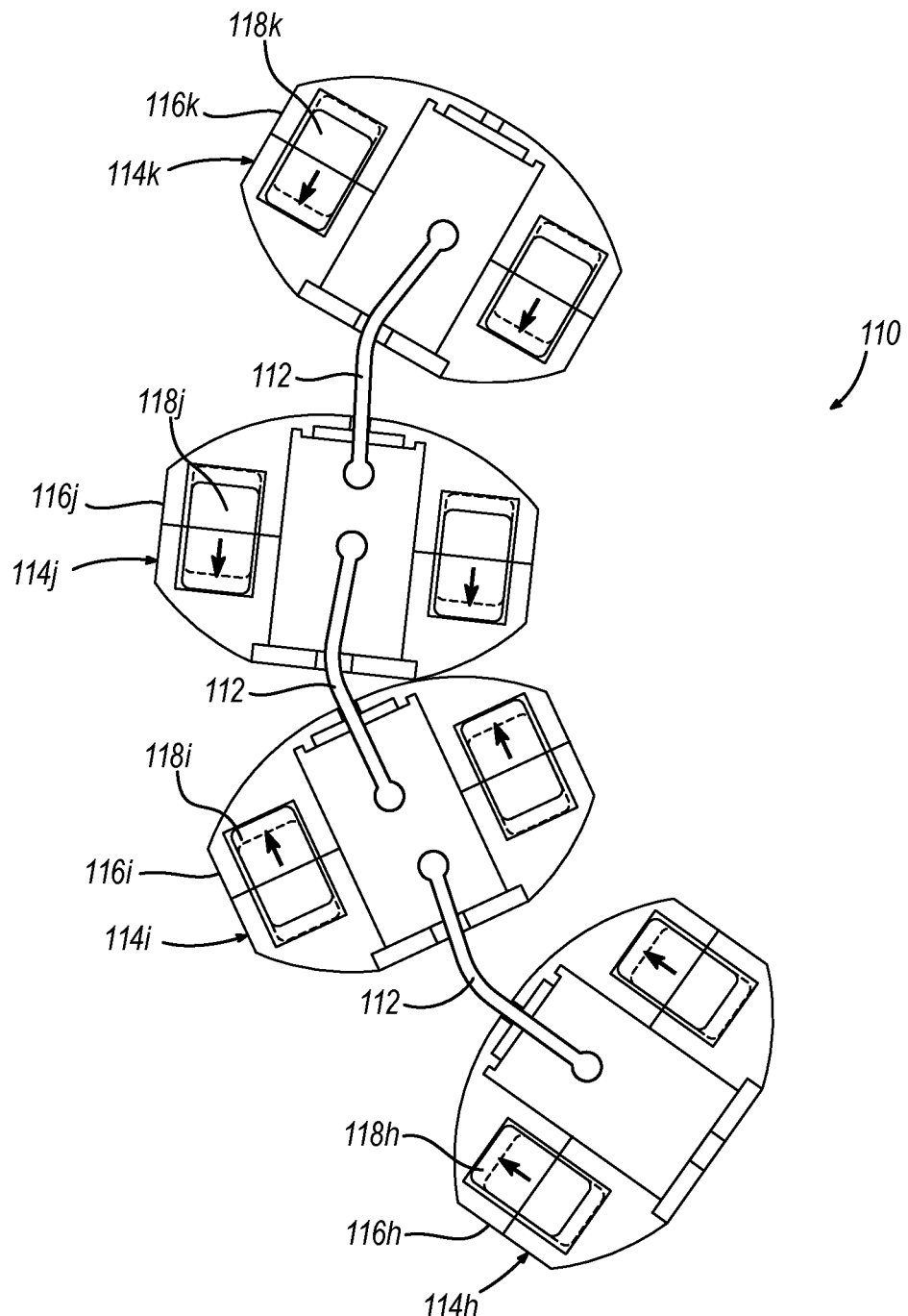
FIG. 8 depicts a partial sectional view of the sphincter augmentation device of FIG. 7 with magnets moved within beads to alter magnetic field intensity.

As shown in FIGS. 7-8, one pair of magnets (118a-l) may slide towards each other, while another pair of magnets (118a-l) may slide away from each other. Magnets (118a-l) may shift laterally left or right inside magnet chambers (140) of housings (116a-l), to increase or decrease the angle between the magnets (118a-l) and the gap therebetween. The movement of magnets (118a-l) within chambers (140) change the first and second magnetic field strengths of high, medium, and low magnetic strength interfaces (126, 128, 130). As shown, magnets (118a, 118k, 118l) shift to the right, and magnet (118b) shifts to the left. As shown in FIG. 7, low magnetic strength interfaces (130) result in a greater angle between adjacent beads (114a-l). Particularly, angle ($a_1$) for low magnetic strength interface (130) is greater than angle ($a_2$) for medium magnetic strength interfaces (128), which is greater than angle ($a_3$) for high magnetic strength interfaces (126). Angles ($a_1$, $a_2$, $a_3$) refer to the angle between unshifted magnets (118a-b, 118k-l), and angles ($b_1$, $b_2$, $b_3$) refer to the angle between the shifted magnets (118a-b, 118k-l). Angles ($a_1$, $b_1$) are measured between a second side (144) of magnet (118k) and a first side (142) of magnet (118l). Angles ($a_2$, $b_2$) are measured between a second side (142) of magnet (118l) and a first side (144) of magnet (118a). Angles ($a_3$, $b_3$) are measured between a second side (150) of magnet (118a) and a first side (152) of magnet (118b).

A gap (g) refers a distance between unshifted magnets (118a-b), and a modified gap (g1) refers to the gap between magnets (118a-b) after the shifting of magnets (118a-b). As shown in FIG. 7, gap (g) and modified gap (g1) are measured between second side (150) of magnet (118a) and first side (152) of magnet (118b). As shown, magnet (118k) twists within magnet chamber (140). Magnets (118a-l) may twist within magnet chambers (140) due to gaps between magnet (118a-l) and magnet chambers (140). As described with reference to magnets (2232o-p) in FIGS. 39-40, these gaps (G1, G2) may allow for lateral movement of magnets (118a-l) and/or twist of magnets (118a-l) within magnet chambers (140).

Figure 9:
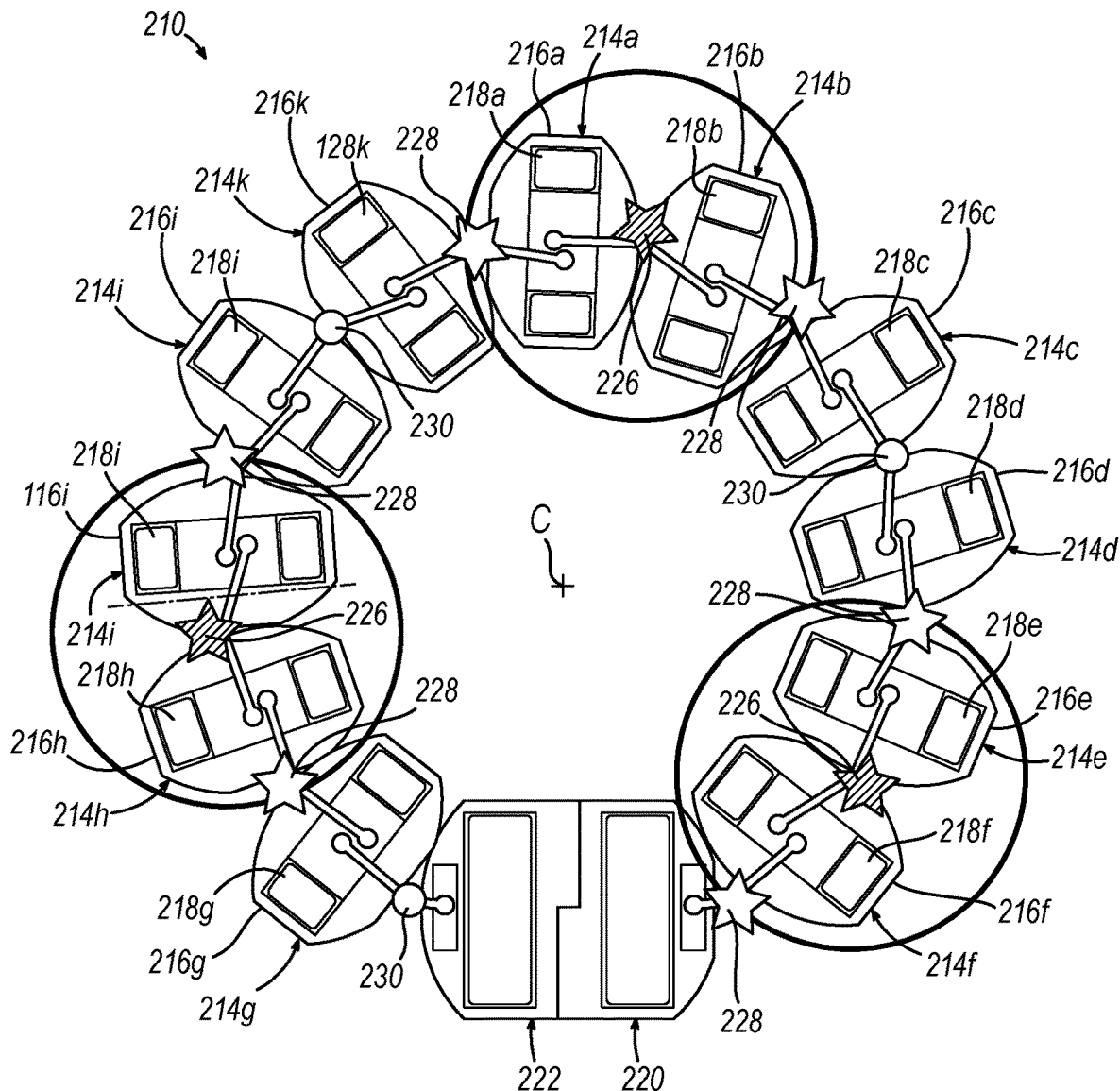
FIG. 9 depicts a top schematic plan view of a second exemplary alternative sphincter augmentation device in a closed and contracted configuration.
Figure 10:
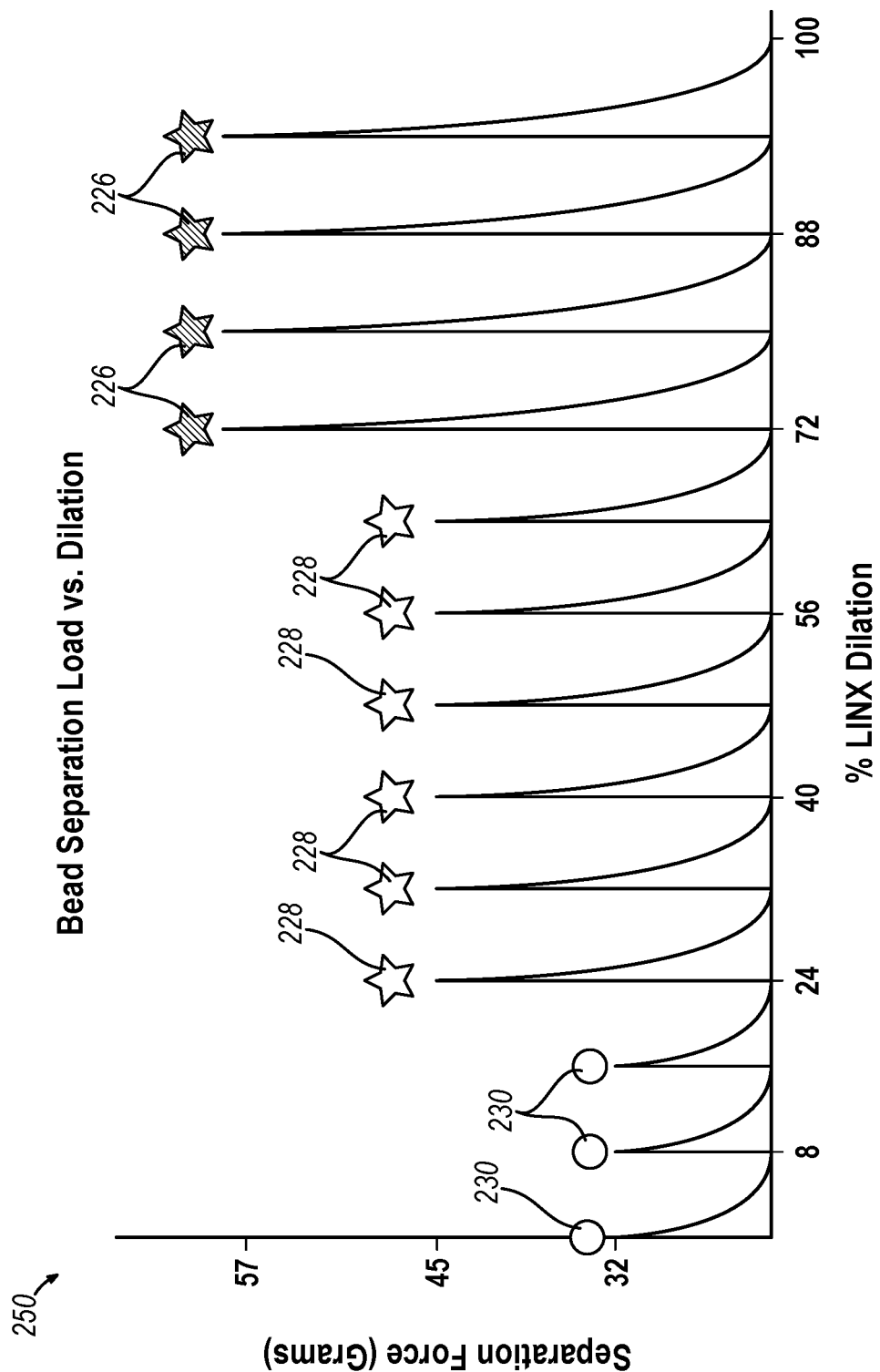
FIG. 10 depicts a graph of a plot showing the separation force relative to the expansion percentage of the sphincter augmentation device of FIG. 9.

B. Second Exemplary Sphincter Augmentation Device to Provide Uniform Radial Expansion and Contraction FIG. 9 shows a second exemplary sphincter augmentation device (210), which is similar to device (110) described above, with differences described below. Device (210) includes links (212) and beads (214a-k), which may be substantially similar to links (112) and beads (114a-l) described above. Beads (214a-k) include housings (216a-k) that each receive at least one magnet (218a-k), which may be similar to magnets (60, 118a-l). As shown and described in detail below, magnets (610, 710, 810, 910, 1024) may be used in place of magnets (218a-k). First and second coupling portions (220, 222) may be coupled together to form an annular arrangement in a similar manner to first and second coupling portions (120, 122). Instead of or in addition to incorporating magnet (118a-l) sliding within cavities shown and described with reference to FIGS. 7-8, device (210) may utilize magnets (218a-k) having different magnetic strengths to obtain a more uniform radial expansion and contraction. Such an arrangement may provide controlled homogenous expansion of beads (30) of device (20).

In the annular arrangement, device (210) may move from the contracted configuration similar to FIG. 6A, through an intermediate configuration similar to FIG. 6B, and to the expanded configuration similar to FIG. 6C. Similarly, device (210) may move from the expanded configuration similar to FIG. 6C, through the intermediate configuration similar to FIG. 6B, and to the contracted configuration similar to FIG. 6A. Beads (214a-i) are magnetically biased to the contracted state. Adjacent beads (214a-k) may be magnetically attracted together at a plurality of bead-to-bead magnetic interfaces that include first, second, and third magnetic interfaces. In some versions, the first magnetic interface may include a high magnetic strength interface (226). Examples of high magnetic strength interfaces (226) are shown between beads (214a-b), between beads (214e-f), and between beads (214h-i). The second magnetic interface may include a medium magnetic strength interface (228). Examples of medium magnetic strength interfaces (228) are shown between beads (214b-c), between beads (214d-e), between bead (214f) and coupling portion (220), between bead (214g-h), and between beads (214i-j), and between beads (214a, 214k). The third magnetic interface (214c-d) may include a low magnetic strength interface (230). Examples of low magnetic strength interfaces (230) are shown between beads (214c-d), between coupling portion (222) and bead (214g), between beads (214j-k). As shown, high magnetic strength interfaces (226) are angularly spaced apart from each other around the annular arrangement. Similarly, medium high magnetic interfaces (228) are angularly spaced apart from each other around the annular arrangement. Similarly, low magnetic strength interfaces (230) are angularly spaced apart from each other around the annular arrangement.

High magnetic strength interfaces (226) may have a first magnetic field strength. Medium magnetic strength interfaces (228) may have a second magnetic field strength that is less than the first magnetic field strength. Low magnetic strength interfaces (230) may have a third magnetic field strength that is less than the first or second magnetic field strengths. The selective placement of high, medium, and low magnetic strength interfaces (226, 228, 230) around the annular arrangement may provide uniform radial expansion and contraction of the annular arrangement of beads (214a-k) as device (210) moves between the contracted, intermediate, and expanded configurations as well as between the expanded, intermediate, and contracted configurations. While three levels (high, medium, and low) of magnetic strength interfaces are shown in FIGS. 6A-6C, fewer levels (e.g., first and second levels) or additional levels (e.g., a fourth, fifth, sixth level, etc.) are also envisioned. Additionally, while first and second magnetic interfaces are shown and described as high and medium magnetic strength interfaces (226, 228), in other versions, the first and second magnetic interfaces may include medium and low magnetic strength interfaces or high and low magnetic strength interfaces.

When using three levels, low magnetic strength interfaces (230) are the first interfaces to separate (e.g., where the beads (214a-k) spread apart) when moving from the contracted configuration of FIG. 6A to the expanded configuration of FIG. 6C; and are the last interfaces to attach when moving from the expanded configuration to the contracted configuration. Conversely, high magnetic strength interfaces (226) are the last interfaces to separate when moving from the contracted configuration to the expanded configuration; and are the first interfaces to attach when moving from the expanded configuration to the contracted configuration. Medium magnetic strength interfaces (228) separate at a time after low magnetic strength interfaces (230) but before high magnetic strength interfaces (226). Medium magnetic strength interfaces (228) attach at a time after high magnetic strength interfaces (226) but before low magnetic strength interfaces (230). As shown, beads (214a-i) have low magnet forces which would result in three separate groupings of bead separation occurring. In the arrangement shown, the shaded starred interfaces (226) separate first, followed by the non-shaded starred interfaces (228), followed by the non-shaded circled interfaces (230). By utilizing such a pattern, the load on LES (6) is more balanced around a centerpoint (C) of the annular arrangement.

It may be beneficial to control the separation force and reattachment force of magnets (218a-i) using magnets (218a-i) having specific magnetic strengths. By way of example only, magnets (218a-i) of device (210) may have a force range of between about 32 and 57 grams. During manufacturing, separating magnets (218a-i) in groups based on the magnet forces (e.g., one gram increments) and assembling those magnets (218a-i) with equivalent forces with each other may result in a more homogenous expansion since the magnetic forces between beads (214a-k) would be equivalent. For example, in some versions, two groups of magnets (e.g., high strength and low strength magnets) may be arranged in specific patterns in device (210) to drive symmetrical separation of device (210) around LES (6) and a more balanced effect on opening and closing of LES (6).

Device (210) may incorporate differing magnetic separation forces to treat different patients. For example, patients with greater stomach pressures may use versions of device (210) with magnets having a higher magnetic strength. Conversely, patients with lower stomach pressures could use versions of device (210) with magnets having lower magnetic strengths. In some instances, using magnets having lower magnetic strengths may decrease occurrences of dysphagia by better sizing patients relative to their individual needs.

Figure 11:
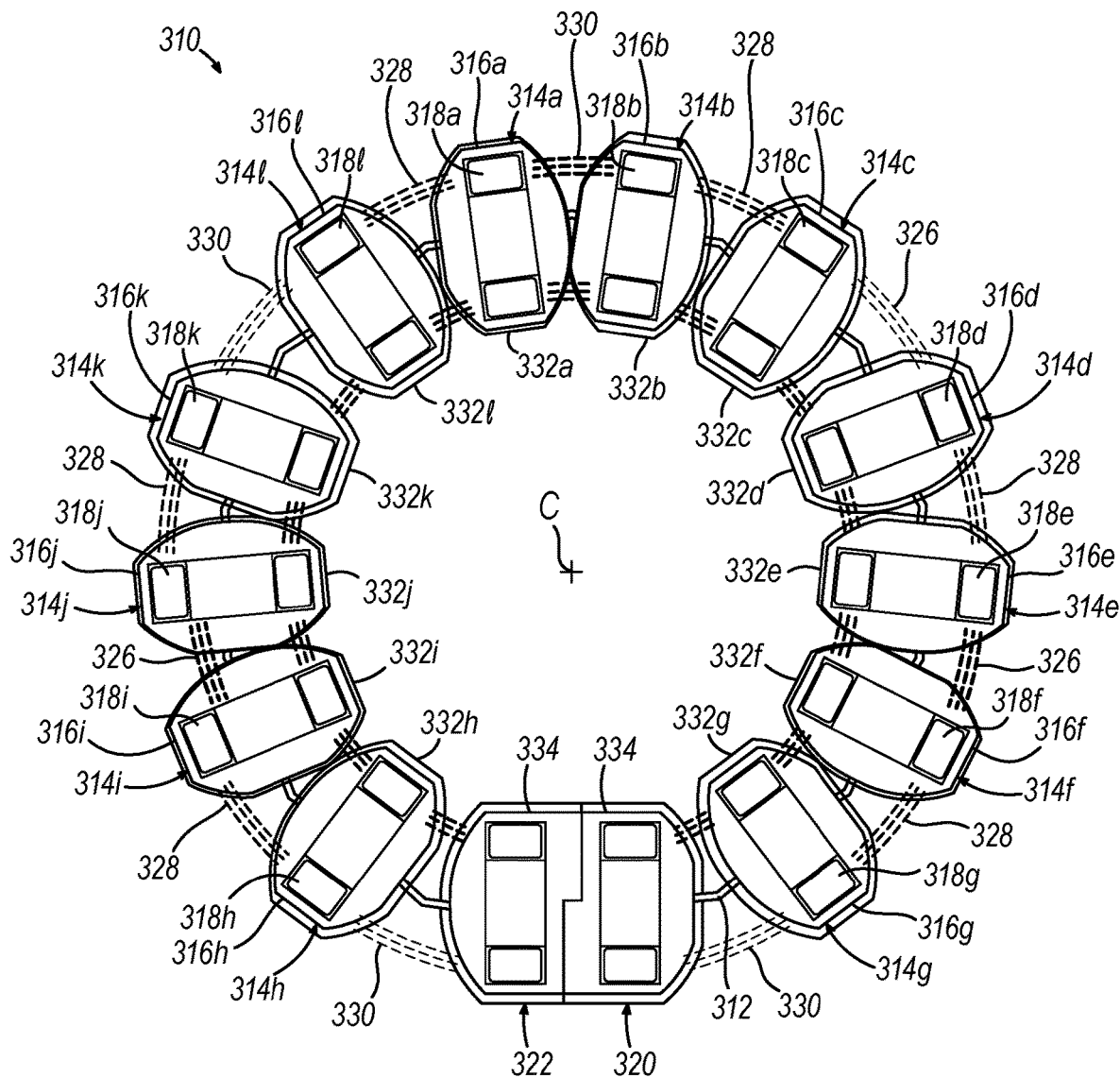
FIG. 11 depicts a top plan view of a third exemplary alternative sphincter augmentation device in a partially closed and contracted configuration.

C. Third Exemplary Sphincter Augmentation Device to Provide Uniform Radial Expansion and Contraction FIG. 11 shows a third exemplary sphincter augmentation device (310), which is similar to device (110) described above, with differences described below. Device (310) includes links (312) and beads (314a-l), which may be substantially similar to links (112) and beads (114a-l) described above. Beads (314a-l) include housings (316a-l) that each receive at least one magnet (318a-l), which may be similar to magnets (60, 118a-l). As shown and described in detail below, magnets (610, 710, 810, 910, 1024) may be used in place of magnets (318a-l). First and second coupling portions (320, 322) may be coupled together to form an annular arrangement in a similar manner to first and second coupling portions (120, 122). In the annular arrangement, device (310) may move from the contracted configuration similar to FIG. 6A, through an intermediate configuration similar to FIG. 6B, and to the expanded configuration similar to FIG. 6C. Likewise, device (310) may move from the expanded configuration similar to FIG. 6C, through the intermediate configuration similar to FIG. 6B, and to the contracted configuration similar to FIG. 6A. Instead of or in addition to incorporating magnet (118a-l) sliding within cavities shown and described with reference to FIGS. 7-8, device (310) may utilize magnets (318a-l) having different magnetic strengths to obtain a more uniform radial expansion and contraction. Such an arrangement may provide controlled homogenous expansion of beads (30) of device (20).

Adjacent beads (314a-l) may be magnetically attracted together at a plurality of bead-to-bead magnetic interfaces that include first, second, and third magnetic interfaces. In some versions, the first magnetic interface may include a high magnetic strength interface (326). Examples of high magnetic strength interfaces (326) are shown between beads (314a-b), between beads (314e-f), and between beads (314h-i). The second magnetic interface may include a medium magnetic strength interface (328). Examples of medium magnetic strength interfaces (328) are shown between beads (314b-c), between beads (314d-e), between bead (314f) and coupling portion (320), between bead (314g-h), and between beads (314i-j), and between beads (314a, 314k). The third magnetic interface (314c-d) may include a low magnetic strength interface (330). Examples of low magnetic strength interfaces (330) are shown between beads (314c-d), between coupling portion (322) and bead (314g), between beads (314j-k). As shown, high magnetic strength interfaces (326) are angularly spaced apart from each other around the annular arrangement. Similarly, medium high magnetic strength interfaces (328) are angularly spaced apart from each other around the annular arrangement. Similarly, low magnetic strength interfaces (330) are angularly spaced apart from each other around the annular arrangement.

High magnetic strength interfaces (326) may have a first magnetic field strength. Medium magnetic strength interfaces (328) may have a second magnetic field strength that is less than the first magnetic field strength. Low magnetic strength interfaces (330) may have a third magnetic field strength that is less than the first or second magnetic field strengths. The selective placement of high, medium, and low magnetic strength interfaces (326, 328, 330) around the annular arrangement may provide uniform radial expansion and contraction of the annular arrangement of plurality of beads as device (310) moves between the contracted, intermediate, and expanded configurations as well as between the expanded, intermediate, and contracted configurations. While three levels (high, medium, and low) of magnetic strength interfaces are shown in FIGS. 6A-6C, fewer levels (e.g., first and second levels) or additional levels (e.g., a fourth, fifth, sixth level, etc.) are also envisioned. Additionally, while first and second magnetic interfaces are shown and described as high and medium magnetic strength interfaces (326, 328), in other versions, the first and second magnetic interfaces may include medium and low magnetic strength interfaces or high and low magnetic strength interfaces.

At least one bead (314a-l) includes an elastomeric encasement (332a-l, 334). Elastomeric encasement (332a-l, 334) is configured to reduce the second magnetic field strength relative to the first magnetic field strength. In some versions, each bead (314a-l) includes elastomeric encasement (332a-l). In some versions, some beads (314a-l) or coupling portions (320, 322) may omit elastomeric encasement (332a-l, 334). As shown, elastomeric encasements (332a-l, 334) have different thicknesses to affect the magnetic fields between beads (314a-l) as well as coupling portions (320, 322). For example, thinner elastomeric encasements (332a-b, 332d-e, 332h-i) have increased magnetic fields relative to the same bead having thicker elastomeric encasements (332b-c, 332f, 332g, 332j-k, 334). Elastomer encasements (332a-l) over beads (314a-l) produce lower bead separation forces and/or gradual release forces until bead separation occurs. This is due to the increase in distance between magnets, which is an exponential decay of force by distance. Also, the elastomeric material of elastomeric encasements (332a-l, 334) may build-up or retain some portion of the energy and as the force is removed the elastomer durometer could adjust the minimum force to separate because it could release the energy at a constant rate rather than merely being a build up to a threshold.

III. EXAMPLES OF DEVICES WITH CONCENTRATED OR DIFFUSED BEAD-TO-BEAD MAGNETIC FIELD INTERACTIONS

Figure 12:
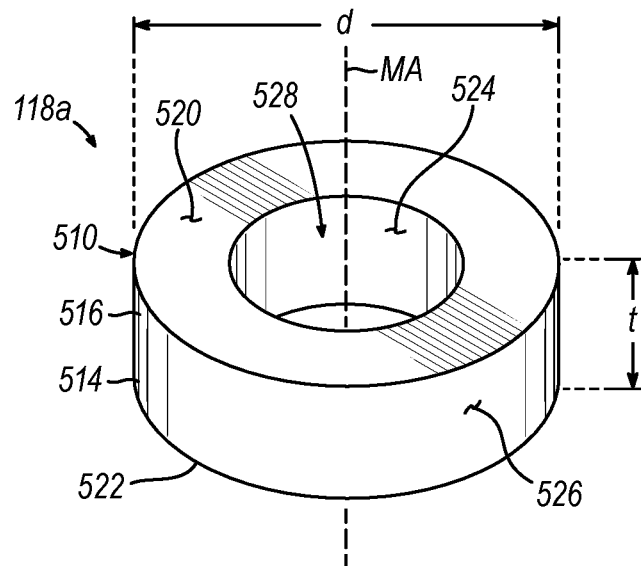
FIG. 12 depicts a perspective view of an annular magnet of the sphincter augmentation device of FIG. 6A.
Figure 13:
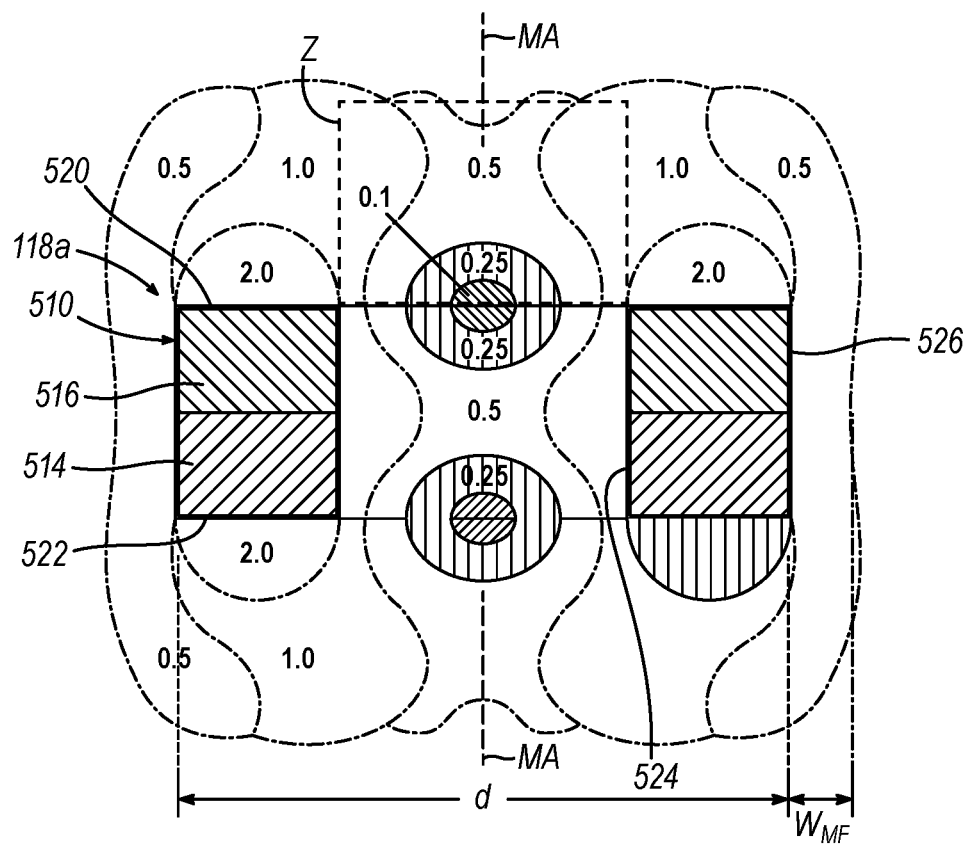
FIG. 13 depicts a sectional view of the annular magnet of FIG. 12 and the corresponding magnetic field intensity.

FIGS. 12-13 show an annular magnet (118a) configured for use with beads (30, 114a-l, 214a-k, 314a-l) of devices (20, 110, 210, 310). Magnet (118a) includes an annular body (512). While a single annular magnet (118a) is shown, a plurality of annular magnets (e.g., annular or toroidal rare-earth permanent magnets (60)) stacked next to each other may be used. Magnets (610, 710, 810, 910, 1024) may be used in place of magnet (118a). Annular body (512) includes a north pole section (514) and a south pole section (516). As shown in FIG. 13, annular body (512) has a thickness (t) and a diameter (d). Magnet (118a) includes first flat magnet surface (520), a second flat magnet surface (522), an inner magnet surface (524), and an outer magnet surface (526). Inner magnet surface (524) defines an aperture (528). A center of aperture (528) defines a magnet axis (MA). Second flat magnet surface (522) is disposed opposite the first flat magnet surface (520). First flat magnet surface (520, 522) includes south pole section (516), and second flat magnet surface (522) includes north pole section (514). Annular body (512) may be centered in housing (116a) of bead (112a). Annular body (512) is not shown as including any surface features.

FIG. 13 shows various magnetic field regions, where the shape of magnet (118a) may control the size and shape of each magnetic field region. As shown, the 1.0 value represents 100% of the ideal magnetic strength of device (20). The 2.0 value region represents 200% of the ideal magnetic strength of device (20), the 0.5 value region represents 50% of the ideal magnetic strength of device (20), the 0.25 value region represents 25% of the ideal magnetic strength of device (20), and the 0.1 value region represents 10% of the ideal magnetic strength of device (20). In some instances, if the magnetic strength that is too high magnet (118a) may cause migration of device (20) through tissue of the sphincter (e.g., the LES (6)); and conversely, if the magnetic strength is too low, magnets (118a-l) may insufficiently contract the sphincter. Thus, an "ideal magnetic strength" may avoid migration of device (20) through tissue while providing sufficient contraction of the sphincter when device (20) is in the contracted state.

The shape of housing (32) may complement the shape of magnet (118a) and direct the magnetic field towards a contact area of adjacent beads (30). This may control the force of housing (116a) on device (20) surrounding tissue. In addition, controlling the magnetic field may aid and/or control the retraction and guidance of links (112) to the desired position. It may be beneficial to alter the geometry of magnet (118a) to focus or concentrate the magnetic field at a defined contact point. As a result of altering the geometry of magnet (118a), the magnetic field may be increased at a predetermined location.

As will be described in detail below with reference to FIGS. 14-21, annular magnet (118a-l) may include one or more surface features to drive the focal point of the magnetic field to a tunable point with respect to housing (116a) and the interface with an adjacent housing (e.g., 116b, 116l). The surface feature may include one or more of extending aspects, surface facets, edge or end conditions, or voids of the magnetic element to concentrate or diffuse the bead-to-bead magnetic field interactions of two adjacent beads (112a-l). Geometric differences in the magnet shapes or features may induce magnetic pull in predefined locations.

Alterations of the magnet shape in the surfaces facing each other may alter the homogeneity or the intensity of the magnetic field interface of the adjacent magnet, where magnet shape or features may control magnet properties. Altering the shape of magnets (118a-l) may change the magnetic field interface of the adjacent magnets (118a-1) by changing the distance between adjacent magnets (118a-l).

A. First Exemplary Alternative Magnet

Figure 14:
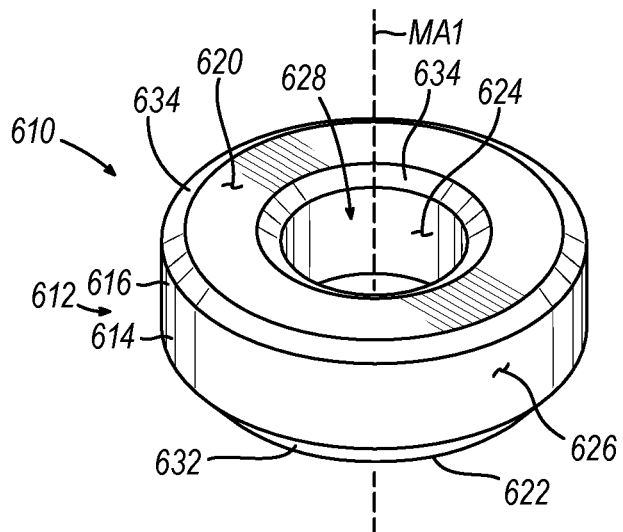
FIG. 14 depicts a perspective view of a first exemplary alternative magnet configured for use with the sphincter augmentation device of FIG. 3.
Figure 15:
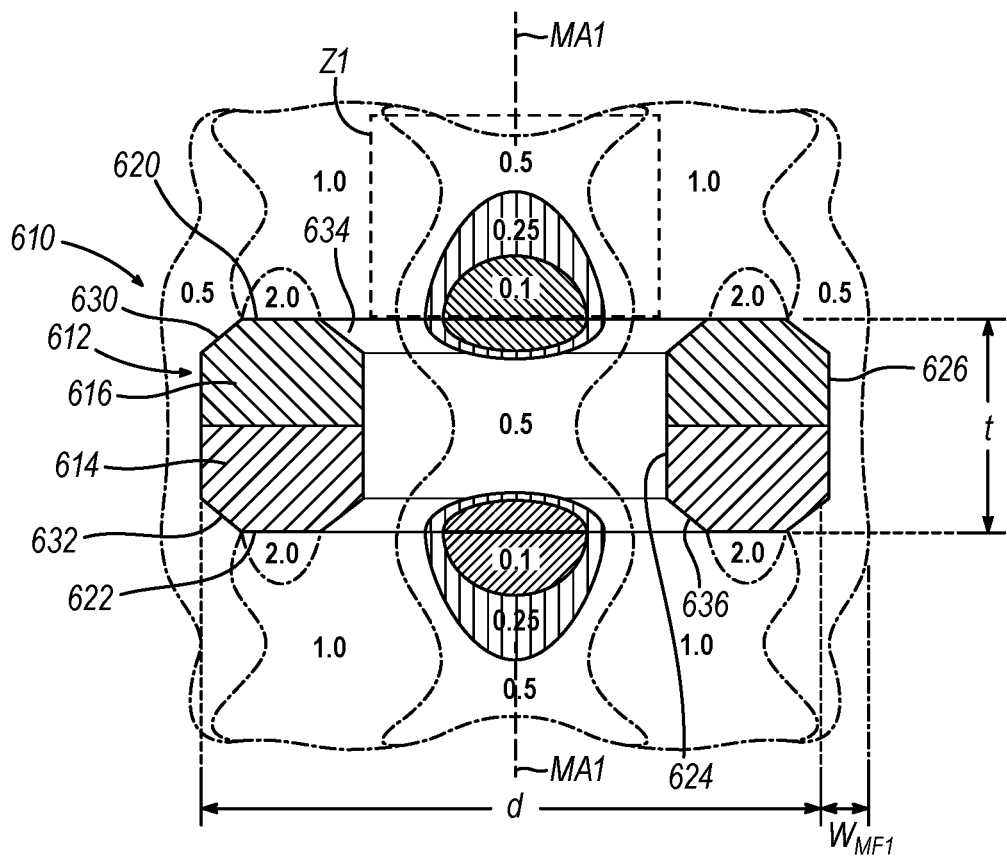
FIG. 15 depicts a sectional view of the magnet of FIG. 14 and the corresponding magnetic field intensity.

FIGS. 14-15 show a first exemplary alternative magnet (610) that may be used instead of magnets (118a-l, 218a-k, 318a-l) or magnets (60) for use with beads (30, 114a-1, 214a-k, 314a-l) of devices (20, 110, 210, 310). Magnet (610) includes an annular body (612). As shown in FIG. 15, annular body (612) has a thickness (t) and a diameter (d). Annular body (612) includes a north pole portion (614) and a south pole portion (616). Magnet (118a) includes first flat magnet surface (620), a second flat magnet surface (622), an inner magnet surface (624), and an outer magnet surface (626). Inner magnet surface (624) defines an aperture (628). A center of aperture (628) defines a magnet axis (MA1). Second flat magnet surface (622) is disposed opposite the first flat magnet surface (620). First flat magnet surface (620) includes south pole portion (616), and second flat magnet surface (622) includes north pole portion (614). Inner and outer magnet surfaces (624, 626) each include north pole portion (614) and south pole portion (616). Outer magnet surface (626) is disposed between the first and second magnet flat surfaces (620, 622). Outer magnet surface (626) defines an outer perimeter of magnet (610).

At least one of the first flat magnet surface (620), second flat magnet surface (622), inner magnet surface (624), or outer magnet surface (626) includes a surface feature. The surface feature may be in the form one or more of a first outer chamfered corner (630), a second outer chamfered corner (632), a first inner chamfered corner (634), or a second inner chamfered corner (636). First outer chamfered corner (630) is disposed between first flat magnet surface (620) and outer magnet surface (626). Second outer chamfered corner (632) is disposed between second flat magnet surface (622) and outer magnet surface (626). First inner chamfered corner (634) disposed between first flat magnet surface (620) and inner magnet surface (624). Second inner chamfered corner (636) is disposed between second flat magnet surface (622) and inner magnet surface (624). In some versions, first and second outer chamfered corners (630, 632) may have a dimension of between approximately 0.01 inches to approximately 0.015 inches. In some versions, first and second inner chamfered corners (634, 636) may have a dimension of approximately 0.005 inches. However, a variety of other sizes for chamfered corners (630, 632, 634, 636) are also envisioned.

Similar to FIG. 13, FIG. 15 shows various magnetic field regions, where the shape of magnet (610) may control the size and shape of each magnetic field region. As shown, the 1.0 value represents 100% of the ideal magnetic strength of device (20). The 2.0 value region represents 200% of the ideal magnetic strength of device (20), the 0.5 value region represents 50% of the ideal magnetic strength of device (20), the 0.25 value region represents 25% of the ideal magnetic strength of device (20), and the 0.1 value region represents 10% of the ideal magnetic strength of device (20). In FIG. 13, the area of the 0.1 value region is about 5% of a rectangular zone (Z). In FIG. 15, the area of the 0.1 value region is about 15% of a rectangular zone (Z1), which is comparable in size to rectangular zone (Z). The combined area of the 0.1 value region and the 0.25 value region in FIG. 15 is greater than the combined area of the 0.1 value region and the 0.25 value region in FIG. 13. A width ($w_{MF1}$) of the 0.5 value region in FIG. 15 is greater than a width ($w_{MF}$) of the 0.5 value region in FIG. 13. The area and dimensions (width and height) of the 2.0 value region in FIG. 13 is greater than the area and dimensions (width and height) of the 2.0 value region in FIG. 15.

Use of magnets (610) including chamfered corners (630, 632, 634, 636) may provide various benefits to devices (20, 110, 210, 310). As shown in FIG. 15, chamfered corners (630, 632, 634, 636) may concentrate or diffuse the magnetic field interactions of adjacent beads (30, 114a-l, 214a-k, 314a-l). For example, the magnetic field interactions of adjacent beads (30, 114a-l, 214a-k, 314a-l) may be concentrated moving toward the magnet axis (MA1) based on chamfered corners (630, 632, 634, 636). The magnetic field interactions of adjacent beads (30, 114a-l, 214a-k, 314a-l) may be diffused moving away from the magnet axis (MA1) (e.g., away from outer magnet surface (626)) based on chamfered corners (630, 632, 634, 636). Chamfered corners (630, 632, 634, 636) may induce magnetic pull in at least one predetermined location between the adjacent beads (30, 114a-l, 214a-k, 314a-l) due to the magnetic field interactions of adjacent beads (30, 114a-l, 214a-k, 314a-l). Chamfered corners (630, 632, 634, 636) may shift a focal point of the magnetic field interactions of adjacent beads (30, 114a-l, 214a-k, 314a-l) to a tunable point between the adjacent beads (30, 114a-l, 214a-k, 314a-l). Chamfered corners (630, 632, 634, 636) cause non-homogenous magnetic fields relative to top and bottom versus side-to-side. Chamfered corners (630, 632, 634, 636) allow for more accurate control of beads (30, 114a-l, 214a-k, 314a-l) which may ultimately affect the how the annular arrangement moves between the contracted configuration and the expanded configuration.

B. Second Exemplary Alternative Magnet

Figure 16:
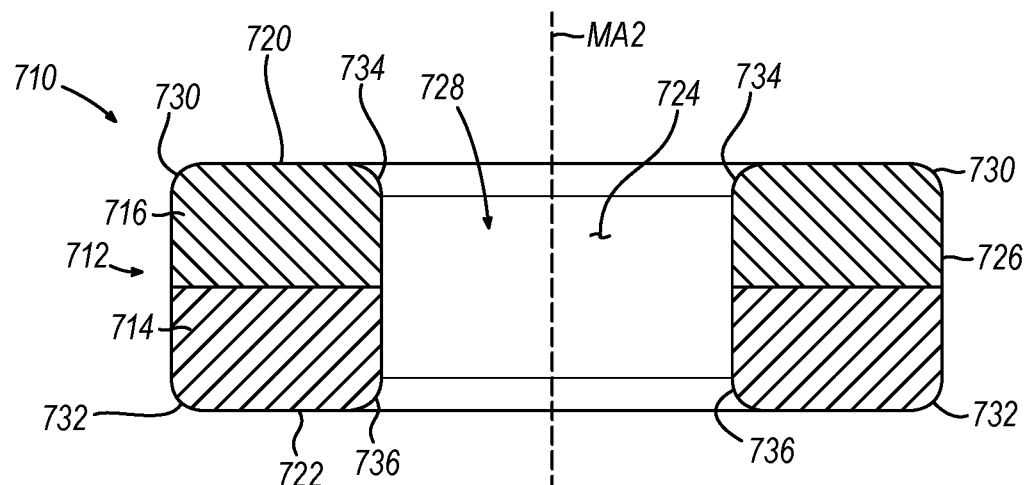
FIG. 16 depicts a perspective view of a second exemplary alternative magnet configured for use with the sphincter augmentation device of FIG. 3.

FIG. 16 shows a second exemplary alternative magnet (710) that may be used instead of magnet (610) for use with beads (30, 114a-l, 214a-k, 314a-l) of devices (20, 110, 210, 310). Magnet (710) includes an annular body (712). Annular body (712) includes a north pole portion (714) and a south pole portion (716). Magnet (118a) includes first flat magnet surface (720), a second flat magnet surface (722), an inner magnet surface (724), and an outer magnet surface (726). Inner magnet surface (724) defines an aperture (728). A center of aperture (728) defines a magnet axis (MA2). Second flat magnet surface (722) is disposed opposite first flat magnet surface (720). First flat magnet surface (720) includes south pole portion (716), and second flat magnet surface (722) includes north pole portion (714). Outer magnet surface (726) is disposed between the first and second magnet flat surfaces (720, 722). Outer magnet surface (726) defines an outer perimeter of magnet (710).

At least one of first flat magnet surface (720), second flat magnet surface (722), inner magnet surface (724), or outer magnet surface (726) includes a surface feature. The surface feature may be in the form one or more of a first outer radiused corner (730), a second outer radiused corner (732), a first inner radiused corner (734), or a second inner radiused corner (736). First outer radiused corner (730) is disposed between first flat magnet surface (720) and outer magnet surface (726). Second outer radiused corner (732) is disposed between second flat magnet surface (722) and outer magnet surface (726). First inner radiused corner (734) is disposed between first flat magnet surface (720) and inner magnet surface (724). Second inner radiused corner (736) is disposed between second flat magnet surface (722), inner magnet surface (724). First and second inner radiused corners (734, 736) have a dimension of approximately 0.005 inches. However, a variety of other sizes for radiused corners (730, 732, 734, 736) are also envisioned. First inner radiused corner (734) is the distance along the radiused corner from first flat magnet surface (720) to inner magnet surface (724). Second inner radiused corner (736) is the distance along the radiused corner from second flat magnet surface (722) to inner magnet surface (724).

Use of magnets (610) including radiused corners (730, 732, 734, 736) may provide various benefits to devices (20, 110, 210, 310). Radiused corners (730, 732, 734, 736) may concentrate or diffuse the magnetic field interactions of adjacent beads (30, 114a-l, 214a-k, 314a-l). Radiused corners (730, 732, 734, 736) may induce magnetic pull in at least one predetermined location between adjacent beads (30, 114a-l, 214a-k, 314a-l) due to the magnetic field interactions of adjacent beads (30, 114a-l, 214a-k, 314a-l). For example, the magnetic field interactions of adjacent beads (30, 114a-l, 214a-k, 314a-l) may be concentrated moving toward the magnet axis (MA2) based on radiused corners (730, 732, 734, 736). The magnetic field interactions of adjacent beads (30, 114a-l, 214a-k, 314a-l) may be diffused moving away from the magnet axis (MA2) (e.g., away from outer magnet surface (726)) based on radiused corners (730, 732, 734, 736). Radiused corners (730, 732, 734, 736) may shift a focal point of the magnetic field interactions of adjacent beads (30, 114a-l, 214a-k, 314a-l) to a tunable point between the adjacent beads (30, 114a-l, 214a-k, 314a-l). Radiused corners (730, 732, 734, 736) cause non-homogenous magnetic fields relative to top and bottom versus side-to-side. Radiused corners (730, 732, 734, 736) allow for more accurate control of beads (30, 114a-l, 214a-k, 314a-l) which may ultimately affect the manner the annular arrangement moves between the contracted configuration and the expanded configuration.

C. Third Exemplary Alternative Magnet

Figure 17:
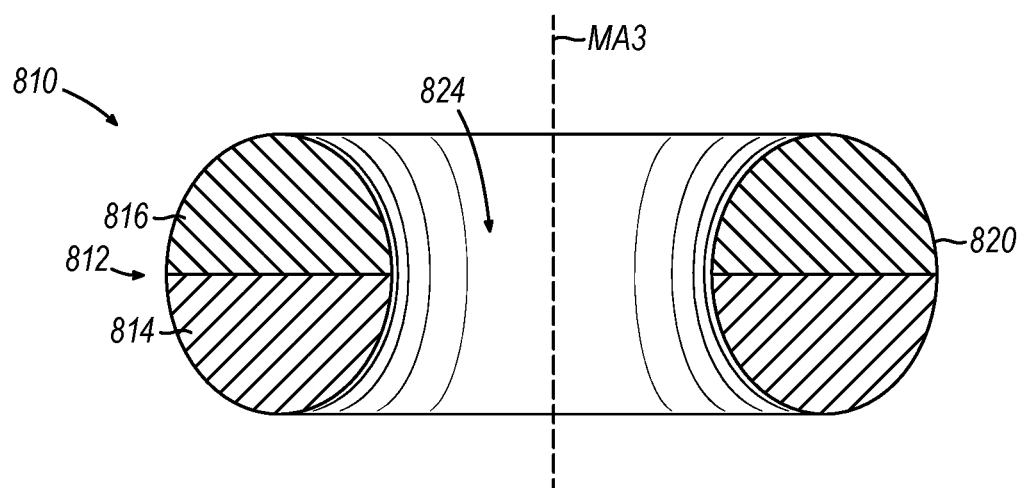
FIG. 17 depicts a perspective view of a third exemplary alternative magnet configured for use with the sphincter augmentation device of FIG. 3.

FIG. 17 shows a third exemplary alternative magnet (810) that may be used instead of magnets (610, 710) for use with beads (30, 114a-l, 214a-k, 314a-l) of devices (20, 110, 210, 310). Magnet (810) includes an annular body (812). Annular body (812) includes a north pole portion (814) and a south pole portion (816). Magnet (810) includes a surface feature in the form of outer arcuate magnet surfaces (820). Outer arcuate magnet surface (820) defines an aperture (824). A center of aperture (824) defines a magnet axis (MA3). Outer arcuate magnet surface (820) defines an outer perimeter of magnet (810). Annular body (812) has a toroid shape configured to induce magnetic pull in at least one predetermined location between adjacent beads (30) due to the magnetic field interactions of adjacent beads (30). The toroid shape is configured to concentrate or diffuse the magnetic field interactions of the adjacent beads (30) and/or shift a focal point of the magnetic field interactions of adjacent beads (30) to a tunable point between the adjacent beads (30). For example, the magnetic field interactions of adjacent beads (30) may be concentrated moving toward the magnet axis (MA3) based on the toroid shape. The magnetic field interactions of adjacent beads (30) may be diffused moving away from the magnet axis (MA3) (e.g., away from outer arcuate magnet surface (820)) based on the toroid shape.

D. Fourth Exemplary Alternative Magnet

Figure 18:
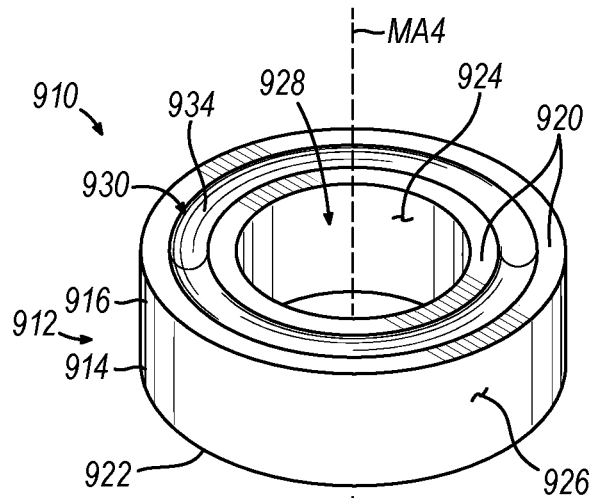
FIG. 18 depicts a perspective view of a fourth exemplary alternative magnet configured for use with the sphincter augmentation device of FIG. 3.
Figure 19:
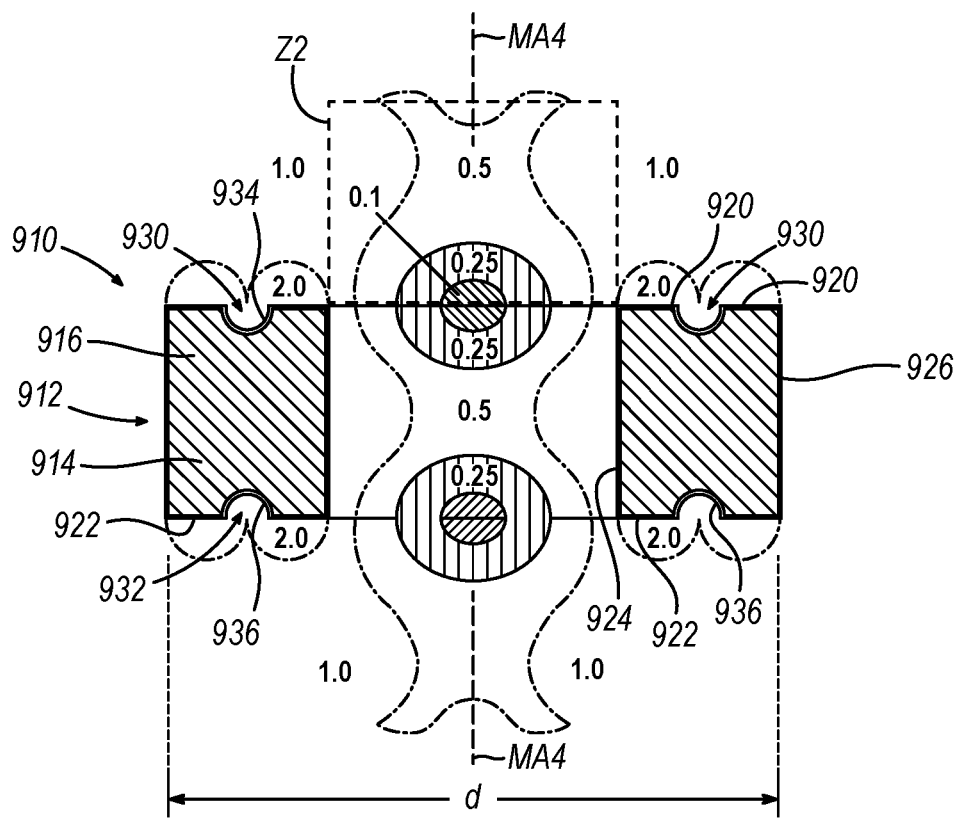
FIG. 19 depicts a sectional view of the annular magnet of FIG. 18 and the corresponding magnetic field intensity.

FIGS. 18-19 show a fourth exemplary alternative magnet (910) that may be used instead of magnets (610, 710, 810) for use with beads (30, 114a-l, 214a-k, 314a-l) in devices (20, 110, 210, 310). Magnet (910) includes an annular body (912). As shown in FIG. 19, annular body (912) has a diameter (d). Annular body (912) includes a north pole portion (914) and a south pole portion (916). Magnet (910) includes first flat magnet surface (920), a second flat magnet surface (922), an inner magnet surface (924), and an outer magnet surface (926). Inner magnet surface (924) defines an aperture (928). A center of aperture (928) defines a magnet axis (MA4). Second flat magnet surface (922) is disposed opposite to first flat magnet surface (920). First flat magnet surface (920) includes north pole portion (914), and second flat magnet surface (922) includes south pole portion (916). Outer magnet surface (926) is disposed between first and second flat magnet surfaces (920, 922). Outer magnet surface (926) defines an outer perimeter of magnet (910).

At least one of the first flat magnet surface (920), first flat magnet surface (922), inner magnet surface (924), or outer magnet surface (926) includes a surface feature. The surface feature may be in the form first and second grooves (930, 932). First groove (930) includes a first inner arcuate surface (934), and second groove (933) includes a second inner arcuate surface (936). While first and second inner arcuate surfaces (934, 936) are shown as being similar, first and second inner arcuate surfaces (934, 936) may be shaped and/sized differently. First groove (930) extends within first flat magnet surface (920) of north pole portion (914). Second groove (932) extends within second flat magnet surface (922) of south pole portion (916). While first and second grooves (930, 932) are shown as being annular grooves, other grooves are also envisioned.

Similar to FIG. 15, FIG. 19 shows various magnetic field regions, where the shape of magnet (910) may control the size and shape of the magnetic field regions. As shown, the 1.0 value represents 100% of the ideal magnetic strength of device (20). The 2.0 value region represents 200% of the ideal magnetic strength of device (20), the 0.5 value region represents 50% of the ideal magnetic strength of device (20), the 0.25 value region represents 25% of the ideal magnetic strength of device (20), and the 0.1 value region represents 10% of the ideal magnetic strength of device (20). In FIG. 13, the area of the 0.1 value region is about 5% of a rectangular zone (Z). In FIG. 19, the area of the 0.1 value region is about 15% of a rectangular zone (Z2), which is comparable in size to rectangular zone (Z). The combined area of the 0.1 value region and the 0.25 value region in FIG. 19 is greater than the combined area of the 0.1 value region and the 0.25 value region in FIG. 13. The area and dimensions (width and height) of the 2.0 value region in FIG. 13 is greater than the area and dimensions (width and height) of the 2.0 value region in FIG. 19.

First and second grooves (930, 932) are configured to concentrate or diffuse the magnetic field interactions of the adjacent beads (30, 114a-l, 214a-k, 314a-l). First and second grooves (930, 932) are configured to induce magnetic pull in at least one predetermined location between adjacent beads (30, 114a-l, 214a-k, 314a-l) due to the magnetic field interactions of adjacent beads (30, 114a-l, 214a-k, 314a-l). First and second grooves (930, 932) are configured to shift a focal point of the magnetic field interactions of adjacent beads (30, 114a-l, 214a-k, 314a-l) to a tunable point between adjacent beads (30, 114a-l, 214a-k, 314a-l). Laterally extending holes or voids (e.g., first and second grooves (930, 932)) create magnetic pull on the angular interactive surfaces than the largest diameter locations. For example, the magnetic field interactions of adjacent beads (30) may be concentrated moving toward the magnet axis (MA4) based on the toroid shape. The magnetic field interactions of adjacent beads (30, 114a-l, 214a-k, 314a-l) may be diffused moving away from the magnet axis (MA4) (e.g., away from outer magnet surface (926)) based on first and second grooves (930, 932). While not shown, it is envisioned that at least one of inner or outer magnet surface (924, 926) may include a groove (which may be similar to first and second grooves (930, 932)).

E. Fifth Exemplary Alternative Magnet

Figure 20:
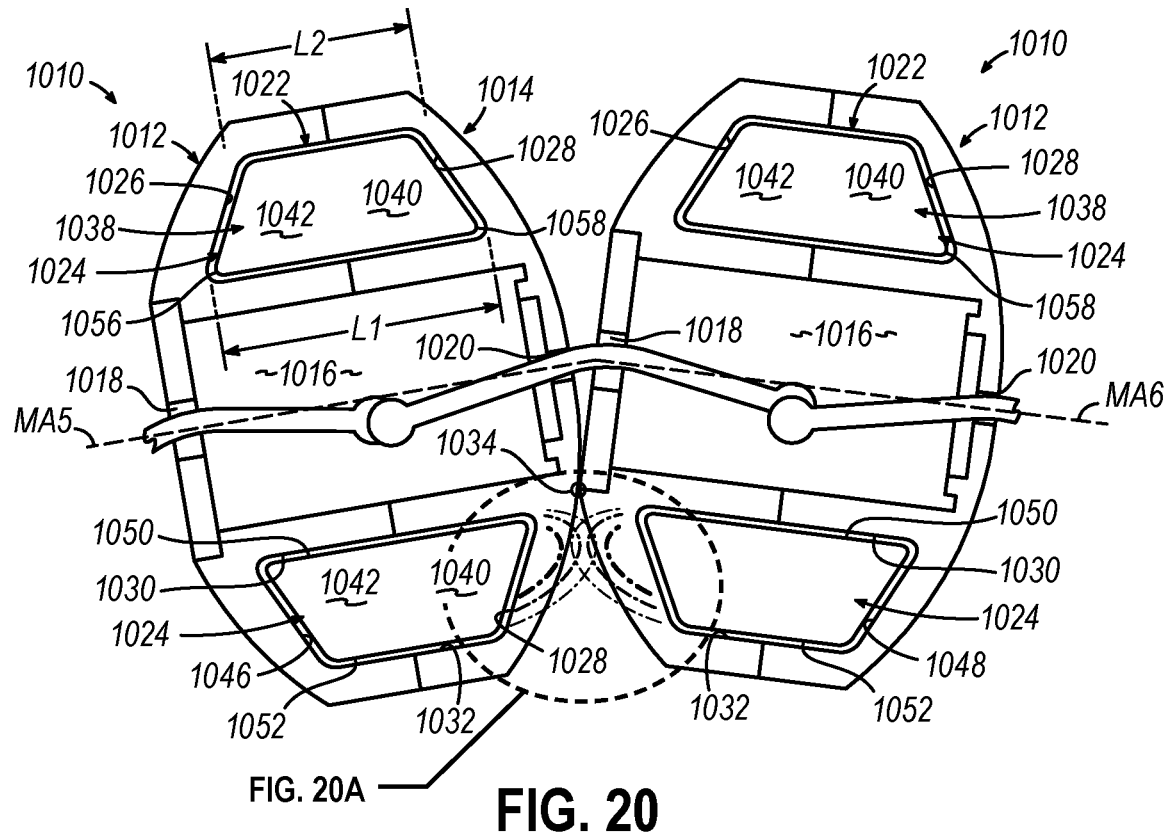
FIG. 20 depicts a sectional view of a pair of first exemplary alternative beads that each include a fifth exemplary alternative magnet configured for use with the sphincter augmentation device of FIG. 3.
Figure 20A:
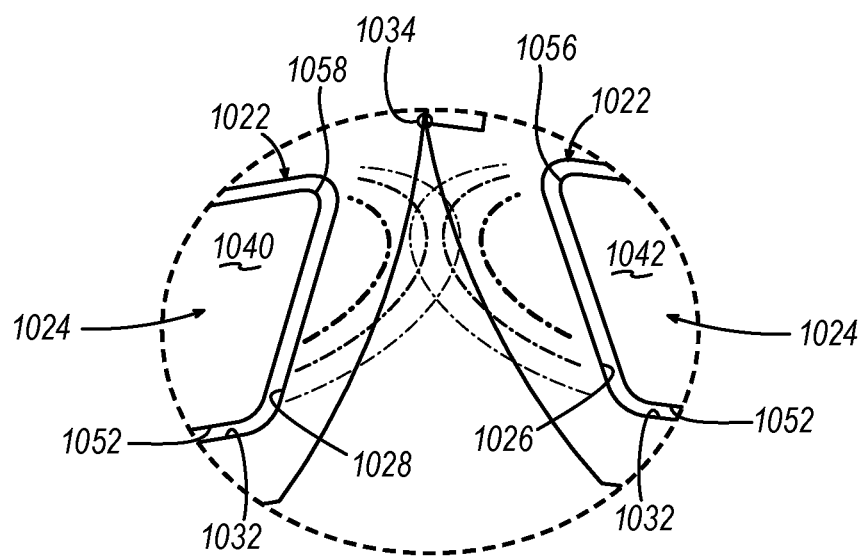
FIG. 20A depicts an enlarged sectional view of beads and magnets of FIG. 20.

FIGS. 20-20A show exemplary alternative beads (1010) connected together using links (40) that may be used in place of (30, 114a-l, 214a-k, 314a-l) of devices (20, 110, 210, 310). Similar to bead (30), each bead (1010) comprises a pair of housings (1012, 1014) that are securely fastened to each other. By way of example only, housings (1012, 1014) may be formed of a non-ferrous material (e.g., titanium, plastic, etc.). Each bead (1010) defines a chamber (1016) that is configured to receive a portion of a respective pair of links (40). Housing (1012) defines an opening (1018) at one end of chamber (1016), and housing (1014) defines an opening (1020) at the other end of chamber (1016). Housings (1012, 1014) collectively form a magnet chamber (1022) that is configured to house at least one magnet (1024). As shown in the cross-section of FIG. 20, magnet chamber (1022) includes a first lateral interior surface (1026), a second lateral interior surface (1028), an inner interior surface (1030), and an outer interior surface (1032). As shown, the cross-section of magnet chamber (1022) forms a trapezoid as compared to the rectangular cross-section formed by the chamber by of housings (32, 34). Housing (1012) includes contact surface (1034). Similarly, housing (1014) includes a contact surface (1036). Contact surfaces (1034, 1036) of adjacent beads (1010) are configured to abut against each other in when a version of device (20) formed by beads (1010) is in the contracted configuration.

Magnet (1024) may be used in place of magnet (118a-l, 218a-k, 318a-l, 610, 710, 810, 910) or magnets (60). Annular magnet (1024) includes an annular body (1038). Annular body (1038) includes a north pole portion (1040) and a south pole portion (1042). Magnet (1024) includes first flat magnet surface (1046), a second flat magnet surface (1048), an inner magnet surface (1050), and an outer magnet surface (1052). Inner magnet surface (1050) defines an aperture (1054). Second flat magnet surface (1048) is disposed opposite the first flat magnet surface (1046). First flat magnet surface (1046) includes south pole portion (1042), and second flat magnet surface (1048) includes north pole portion (1040). Outer magnet surface (1052) is disposed between the first and second flat magnet surfaces (1046, 1048). Outer magnet surface (1052) defines an outer perimeter of magnet (1024), which has a trapezoidal cross-sectional profile.

First lateral interior surface (1026) is configured to receive the first flat magnet surface (1046). Second lateral interior surface (1028) is disposed opposite and angled opposite first lateral interior surface (1026) and is configured to receive the second flat magnet surface (1048). Inner interior surface (1030) is disposed between first and second lateral interior surfaces (1026, 1028). Inner interior surface (1030) extends a first length (L1) between first and second lateral interior surfaces (1026, 1028). Outer interior surface (1032) is disposed between the first and second lateral interior surfaces (1026, 1028) and is configured to receive the outer magnet surface (1052). Outer interior surface (1032) extends a second length (L2) between the first and second lateral interior surfaces. The first length (L1) is greater than second length (L2).

First and second inner corners (1056, 1058) may constitute a surface feature that drive the focal point of the magnetic field to a tunable point with respect to housing (1012). First inner corner (1056) is disposed between inner magnet surface (1050) and first flat magnet surface (1046); and first inner corner (1056) is disposed between inner magnet surface (1050) and second flat magnet surface (1048). First and second inner corners (1056, 1058) may include a chamfer (similar to chamfered corners (630, 632, 634, 636)) and/or a fillet (e.g., radiused corners (730, 732, 734, 736)). The outward tapering of the trapezoid shape (when viewed in cross-section as shown in FIGS. 20 and 20A) positions first and second inner corners (1056, 1058) closer to contact surfaces (1034) of adjacent beads (1010), concentrating the magnetic field interactions between adjacent beads (1010). First and second inner corners (1056, 1058) are configured to induce magnetic pull in at least one predetermined location between adjacent beads (1010) due to the magnetic field interactions of adjacent beads (1010). First and second inner corners (1056, 1058) are configured to shift a focal point of the magnetic field interactions of adjacent beads (1010) to a tunable point between the adjacent beads (1010). For example, the magnetic field interactions of adjacent beads (1010) may be concentrated moving toward respective magnet axes (MA5, MA6) based on first and second inner corners (1056, 1058). The magnetic field interactions of adjacent beads (1010) may be diffused moving away from respective magnet axes (MA5, MA6) (e.g., away from outer arcuate magnet surface (822)) based on first and second inner corners (1056, 1058).

IV. EXAMPLES OF DEVICES WITH REDIRECTED OR FOCUSED MAGNETIC FIELDS FOR INTERACTION BETWEEN ADJACENT BEADS

Device (110) may include magnets (118a-i) (see FIG. 12) centered within housings (32, 34). Magnets (118a-i) generate a magnetic field, which is shown schematically in FIG. 21 using dot-dash lines. The thickness of the dot-dash lines is intended to represent the magnitude of the magnetic field, where thicker dot-dash lines represent stronger magnetic fields and thinner dot-dash lines represent weaker magnetic fields. The thickness (t) of magnet (60) may be selected based on the maximum thickness of magnet (60) that fits within housings (32, 34). Considering the annular shape of magnet (60) with first and second flat surfaces (520, 522) previously shown and described with reference to FIG. 12, the thickness (t) of magnet (60) is limited based on this maximum diameter of magnet (60).

It may be beneficial to increase the magnetic fields of magnets (60) and/or focus the magnetic fields to improve the interaction between beads (30). For example, it may be beneficial to incorporate differences in magnet spacing and/or contact between magnets (60) to improve the interaction between beads (30). As will be described in greater detail below with reference to FIGS. 22-25, it may be beneficial to include at least one additional magnetically sensitive element (e.g., temporary and/or permanent magnets) laterally adjacent to magnet (60). These magnetically sensitive element(s) may alter (e.g., increase) the magnetic field at a predetermined location (e.g., a contact surface between adjacent beads (30)). For example, one or more smaller magnetic sensitive elements may be disposed adjacent to magnets (60) within beads (30).

FIGS. 22-25 show first exemplary alternative beads (1210) which may be incorporated into device (20) in place of beads (30). Beads (1210) may be used in place of or incorporate aspects of beads (30, 114a-l, 214a-k, 314a-l, 1010) of devices (20, 110, 210, 310). Beads (1210) may be linked together to form a ring using links (1211), which may be similar to links (40). Each bead (1210) includes a housing (1212), a magnet (1214), and a secondary element (1216). Magnet (1214) may be similar to magnets (118*a-l*, 218*a-k*, 610, 710, 810, 910, 1024) or may comprise a plurality of magnets (similar to magnets (60)). Housings (1212) may include first and second housing portions (1218, 1220) similar to housings (32, 34). First and second housing portions (1218, 1220) collectively define a passageway (1222) for passage of links (1211). First and second housing portions (1218, 1220) collectively define a magnet chamber (1224) that is configured to receive magnet (1214). Secondary element (1216) is contained within magnet chamber (1224) of housing (1212). Each housing (1212) includes a contact surface (1226). Contact surfaces (1226) of adjacent beads (1210) are configured to selectively abut against each other when a version of device (20) incorporating beads (1210) is in the contracted configuration.

Magnet (1214) is disposed within magnet chamber (1224) of housing (1212) and is configured to generate a magnetic field. Magnet (1214) is constrained in location or is in contact with magnetic susceptible elements of secondary element (1216) to direct the magnetic field between beads (1210) in a predetermined manner or to a predetermined location. In some versions, magnet (1214) may include a permanent magnet that is magnetically coupled with secondary element (1216). Magnet (1214) includes a north pole portion (1228) and a south pole portion (1230). Magnet (1214) includes a first flat magnet surface (1234), a second flat magnet surface (1236), an inner magnet surface (1238), and an outer magnet surface (1240). Inner magnet surface (1238) defines an aperture (1242). Second flat magnet surface (1236) is disposed opposite first flat magnet surface (1234). First flat magnet surface (1234) includes south pole portion (1230). Similarly, second flat magnet surface (1236) includes north pole portion (1228). Outer magnet surface (1240) is disposed between first and second flat magnet surfaces (1234, 1236). Outer magnet surface (1240) defines an outer perimeter of magnet (1214). Magnet (1214) has first size parameters, which may include a first diameter (d1), a first thickness (t1), and a first volume (V1).

As will be described in greater detail below, secondary element (1216) is different from magnet (1214) and is configured to increase and focalize the magnetic field of magnet (1214). Secondary element (1216) is configured to cause the magnetic field produced by magnet (1214) to have focus-extending high magnetic flux in combination with increased areas of repressed magnetic field strength. In some versions, secondary element (1216) may include one or more magnetically susceptible elements that create irregular or fractal magnetic fields to improve the magnetic field interaction between adjacent beads (1210). In some versions, secondary element (1216) includes at least one temporary magnet having a high magnetic susceptibility that is not permanently uniaxial. In other versions, secondary element (1216) includes at least one permanent magnet, that includes one or more materials that is magnetized by an external magnetic field; and remains magnetized after the external magnetic field is removed. In some versions, the permanent magnet may have a uniaxial magnetocrystalline anisotropy. Uniaxial magnetocrystalline anisotropy is intended to mean that magnet (1214) has a magnetization susceptibility that varies based on angular position about a single axis. For example, a magnetic force of about a 35 gram-force may be adjacent outer magnet surface (1240) and a magnetic force of about a 50 gram-force may be adjacent secondary elements (1216). In other words, the magnetic force adjacent outer magnet surface (1240) may be approximately 70% of the magnetic force adjacent secondary elements (1216). Alternatively, the magnetic force adjacent outer magnet surface (1240) may be approximately 80% of the magnetic force adjacent secondary elements (1216); approximately 60% of the magnetic force adjacent secondary elements (1216); or any other percentage ranging from approximately 60% to approximately 80%.

Figure 22:
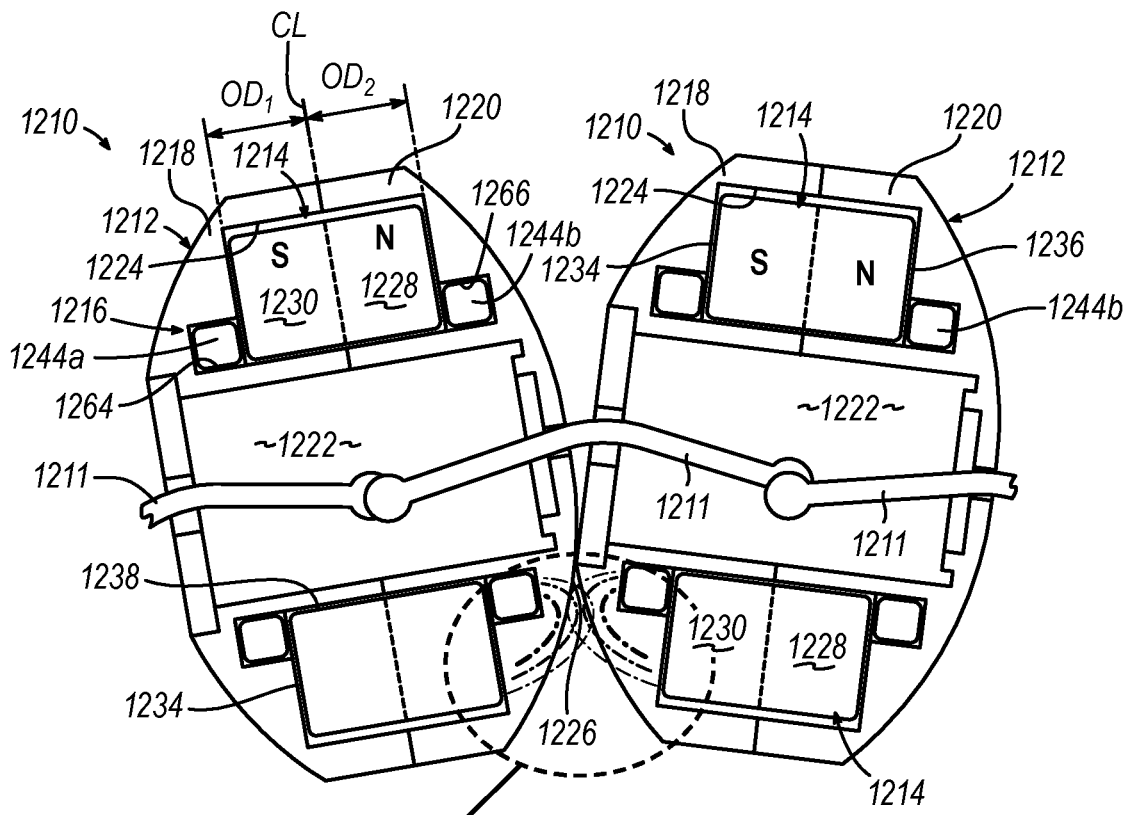
FIG. 22 depicts a schematic sectional view of a pair of second exemplary alternative beads configured for use with the sphincter augmentation device of FIG. 3, where each bead includes a magnet and a secondary element.
Figure 25:
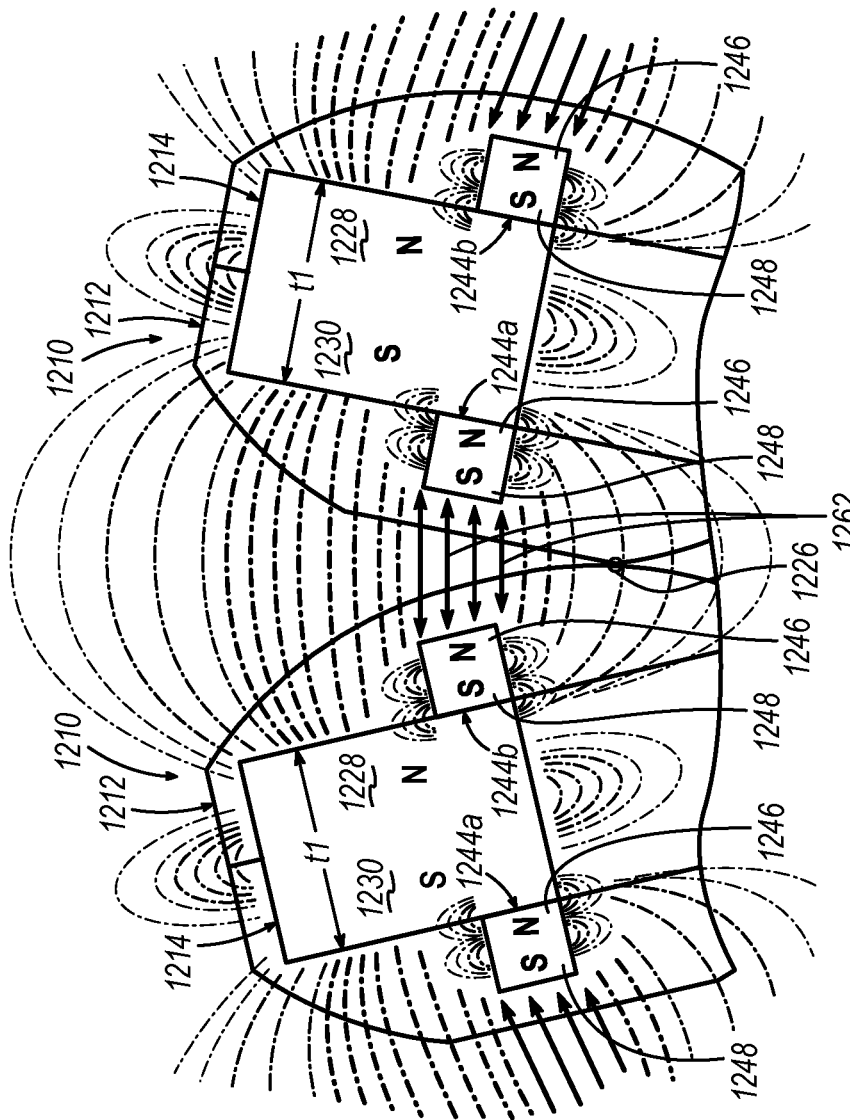
FIG. 25 depicts a schematic partial sectional view of the beads of FIG. 22 generating magnetic fields.

As shown in FIGS. 22-25, secondary element (1216) includes magnetically susceptible elements in the form of first and second annular ferromagnetic elements (1244*a-b*) that are configured to increase the magnetic field between adjacent beads (1210) at a predetermined location. As shown, the predetermined location is contact surface (1226) between beads (1210). First and second ferromagnetic elements (1244*a-b*) focus the magnetic field through the creation of temporary magnetic contacts. First and second ferromagnetic elements (1244*a-b*) each include a first flat magnet surface (1252), a second flat magnet surface (1254), an inner magnet surface (1256), and an outer magnet surface (1258). Inner magnet surface (1256) defines an aperture (1260). Second flat magnet surface (1254) is disposed opposite first flat magnet surface (1252). Outer magnet surface (1258) is disposed between first and second flat magnet surfaces (1252, 1254). Outer magnet surface (1258) defines an outer perimeter of first and second ferromagnetic elements (1244*a-b*). While first and second ferromagnetic elements (1244*a-b*) are shown as annular, a variety of other shapes and sizes are also envisioned. As shown in FIGS. 22 and 25, second flat magnet surface (1254) of first ferromagnetic element (1244*a*) is in direct contact with first flat magnet surface (1234) of magnet (1214). Similarly, first flat magnet surface (1252) of second ferromagnetic element (1244*b*) is in direct contact with second flat magnet surface (1236) of magnet (1214).

Figure 23:
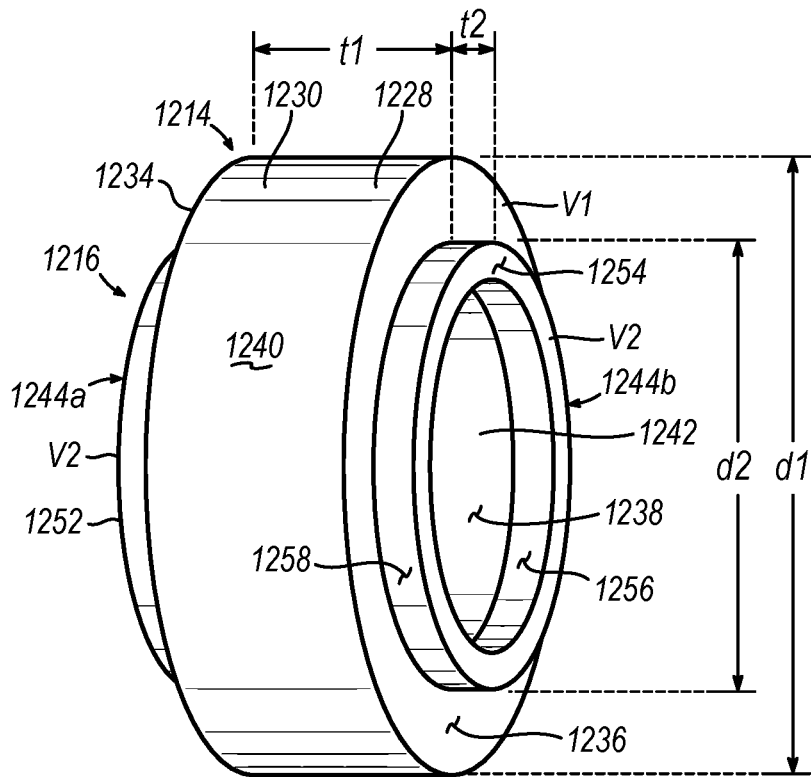
FIG. 23 depicts a perspective view of the magnet and the secondary element of FIG. 22.
Figure 24:
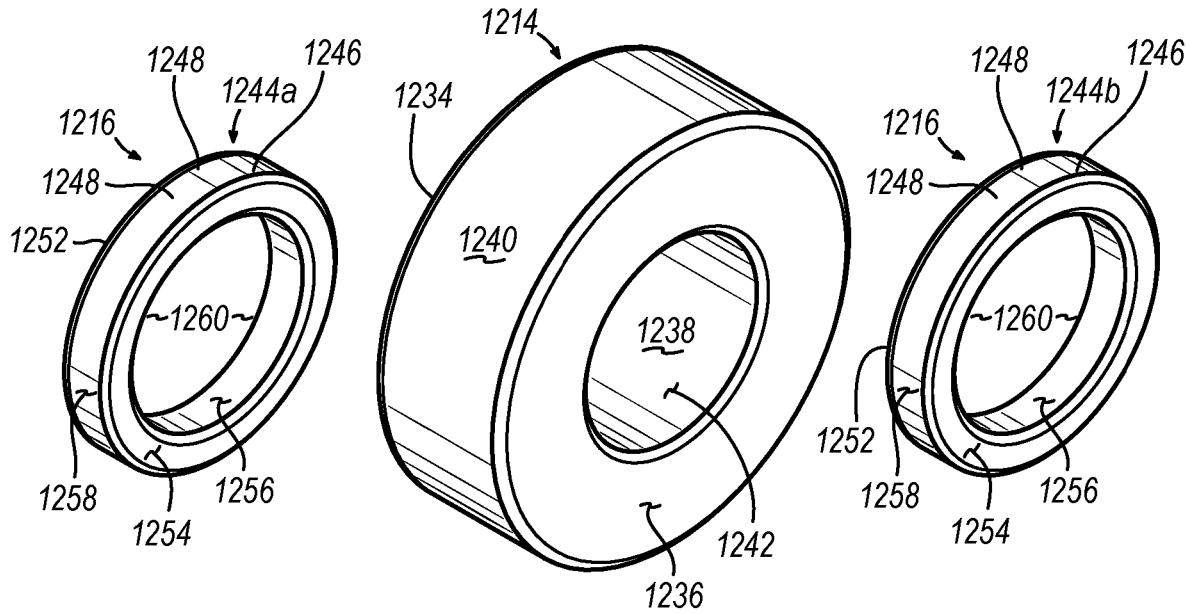
FIG. 24 depicts an exploded perspective view of the magnet and the secondary element of FIG. 23.

First and second ferromagnetic elements (1244*a-b*) are laterally positioned within magnet chamber (1224) of housing (1212) relative to magnet (1214). In other words, first and second ferromagnetic elements (1244*a-b*) are disposed closer to contact surface (1226) than magnet (1214). First and second ferromagnetic elements (1244*a-b*) each have the same inner diameter as magnet (1214), such that inner magnet surfaces (1238, 1256) are coextensive. However, first and second ferromagnetic elements (1244*a-b*) of secondary element (1216) have different thicknesses and outer diameters compared to magnet (1214). First and second ferromagnetic elements (1244*a-b*) each have second size parameters, which may include a second diameter (d2), a second thickness (t2), and a second volume (V2). As shown in FIG. 23, first diameter (d1) is greater than second diameter (d2), first thickness (t1) is greater than second thickness (t2), and first volume (V1) is greater than second volume (V2).

While first and second ferromagnetic elements (1244*a-b*) are shown as having the same shape, size parameters and material, first and second ferromagnetic elements (1244*a-b*) may have different shapes, have different size parameters, and be formed using different materials to adjust the magnetic field and/or intensity at defined locations to control the twist between beads (1210) within and outside externally applied separate magnetic fields. For example, first flat magnet surface (1252) of first ferromagnetic element (1244*a*) and second flat magnet surface (1254) of second ferromagnetic element (1244*b*) may be tapered moving away from magnet (1214) in a similar manner as magnet (1024) shown in FIGS. 20-20A. In some versions, first and second ferromagnetic elements (1244*a-b*) may include other features, such as apertures, bends, patterned surfaces, etc., to further adjust the magnetic field.

Figure 21:
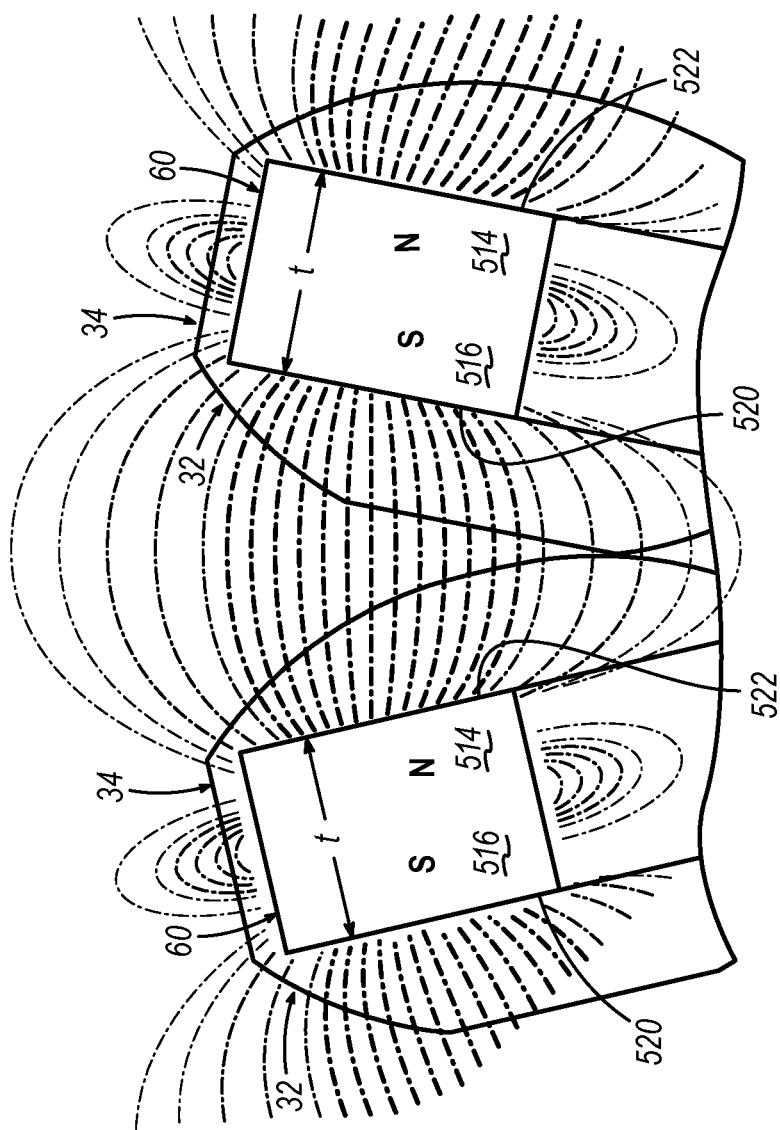
FIG. 21 depicts a schematic sectional view of a portion of the sphincter augmentation device of FIG. 12 generating magnetic fields.
Figure 22A:
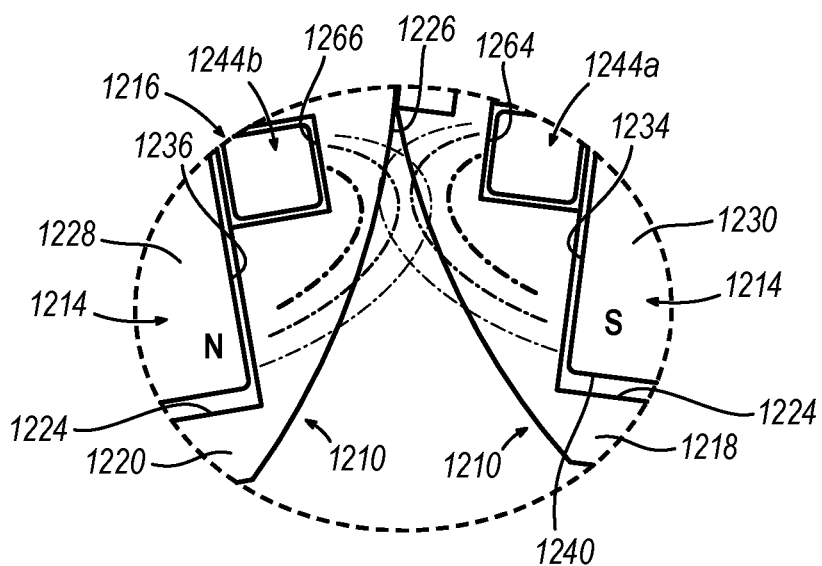
FIG. 22A depicts an enlarged schematic sectional view of a portion of the beads of FIG. 22 generating magnetic fields.

Similar to FIG. 21, the thickness of the dot-dash lines in FIGS. 22-22A and 25 is intended to represent the magnitude of the magnetic field, where thicker dot-dash lines represent stronger magnetic fields and thinner dot dash lines represent weaker magnetic fields. In FIG. 25, intensified magnetic fields due to first and second ferromagnetic elements (1244a-b) are shown using double sided opposing arrows (1262). First and second ferromagnetic elements (1244a-b) are magnetically attracted to magnet (1214). Magnet (1214) is interposed between first and second ferromagnetic elements (1244a-b). First and second ferromagnetic elements (1244a-b) each include a north pole portion (1246) and a south pole portion (1248). First flat magnet surface (1252) includes south pole section (1248), and second flat magnet surface (1254) includes north pole section (1246). Inner and outer magnet surfaces (1256, 1258) each include north pole portion (1246) and south pole portion (1248). North pole portion (1246) of first ferromagnetic element (1244a) is in direct contact with south pole portion (1230) of magnet (1214). South pole portion (1248) of second ferromagnetic element (1244b) is in direct contact with north pole portion (1228) of magnet (1214). The magnetic fields of magnet (1214) and first and second ferromagnetic elements (1244a-b) are shown in FIG. 25 using dot-dash lines.

First and second ferromagnetic elements (1244a-b) affect the overall magnetic field generated by beads (1210), such that magnets (1214) and ferromagnetic elements (1244a-b) together generate a magnetic field having greater complexity than the magnetic field that would otherwise be generated by magnets (1214) alone or by ferromagnetic elements (1244a-b) alone. Use of one or more ferromagnetic elements (1244a-b) may concentrate the magnetic force to a predetermined location. When magnet (1214) and first and second ferromagnetic elements (1244a-b) are stacked together with opposite poles in contact with each other (e.g., north pole in contact with south pole), magnet (1214) and first and second ferromagnetic elements (1244a-b) may function as a single magnet of the same overall height. As a result, stacking of first and second ferromagnetic elements (1244a-b) and magnet (1214) may increase the magnetic force closer to bead-to-bead contact surface (1226) and increase the magnetic pull force at contact surface (1226). It may be beneficial to control the distance from magnet (1214) to contact surface of bead (1210) relative to an adjacent magnet (1214).

Secondary element (1216) is restrained within housing (1212) asymmetrically relative to a centerline (CL) of magnet (1214). As shown, centerline (CL) of magnet (1214) is where first and second housing portions (1218, 1220) contact each other. As shown in FIG. 22, first ferromagnetic element (1244a) is offset a first offset distance (OD1) from centerline (CL) of magnet (1214), and second ferromagnetic element (1244d) is offset a second offset distance (OD2) from centerline (CL) of magnet (1214). While first and second offset distances (OD1, OD2) are shown as being the same, first and second offset distances (OD1, OD2) may be different. As shown in FIGS. 22-22A, first ferromagnetic element (1244a) is restrained within housing (1212) by first flat magnet surface (1234) and a first inner surface (1264) of magnet chamber (1224). Similarly, second ferromagnetic element (1244b) is restrained within housing (1212) by second flat magnet surface (1236) and a second inner surface (1266) of magnet chamber (1224). The asymmetry is configured to form paired sets of beads (1210) with mirrored symmetry between beads (1210) being coupled together and then away from each other between magnets (1214) of paired beads (1210).

First and second ferromagnetic elements (1244a-b) have a high susceptibility to magnetization, the strength of which may be selectively adjusted based on the applied magnetizing field. The strength of first and second ferromagnetic elements (1244a-b) depends on the strength of the magnetic field that persists after removal of the applied magnetizing field. Ferromagnetic materials may be used to control the rotation of beads (1210) relative to one another as the annular arrangement moves between the contracted configuration and the expanded configuration. First and second ferromagnetic elements (1244a-b) may include one or more of iron, cobalt, nickel, alloys thereof, compounds of rare earth metals, and/or other materials. In some versions, first and second ferromagnetic elements (1244a-b) may include iron components (e.g., an iron ring) and not an additional magnet. Incorporating a ring and/or sections of a ferromagnetic material at defined locations and/or zones may magnetize the ferromagnetic material, thereby increasing or decreasing the magnetic field at the predetermined locations. Interactive electrically conductive non-magnetic elements significantly vary magnetic fields between close approximation compared distanced housings (1212) of beads (1210). Passing a magnetic field through an interactive electrically conductive non-magnetic element (e.g., first and second ferromagnetic elements (1244a-b)) creates an electric current that alters the magnetic field because the interactive electrically conductive non-magnetic element creates a second magnetic field in the other element, which may damp the magnetic field. First and second ferromagnetic elements (1244a-b) may absorb the energy and create the second magnetic field to slow the speed of magnet (1214). Ferromagnetic metal material may redirect or alter the magnetic field and/or limit the magnetic pull force. The magnetic pull force may be driven by diameters (d1, d2) and thicknesses (t1, t2) of magnet (1214) and first and second ferromagnetic elements (1244a-b), such that any one or more of these parameters may be selectively altered.

V. EXAMPLES OF DEVICES WITH BIMODAL DISTRIBUTION OF MAGNETIC FIELD INTENSITY RATE-OF-CHANGE

It may be beneficial to create a temporary braking force between beads (30) when beads (30) converge within a predetermined distance from one another. This convergence may occur when beads (30) move as device (20) transitions from the expanded configuration to the contracted configuration. This temporary braking force may temporarily slow the movement of beads (30) as device (20) transitions from the expanded configuration to the contracted configuration. The following description provides examples of how beads (30) may be modified to provide a temporary braking force as a version of device (20) incorporating variations of beads (30) transitions from the expanded configuration to the contracted configuration.

A. Exemplary Alternative Beads with Bimodal Distribution

Figure 26A:
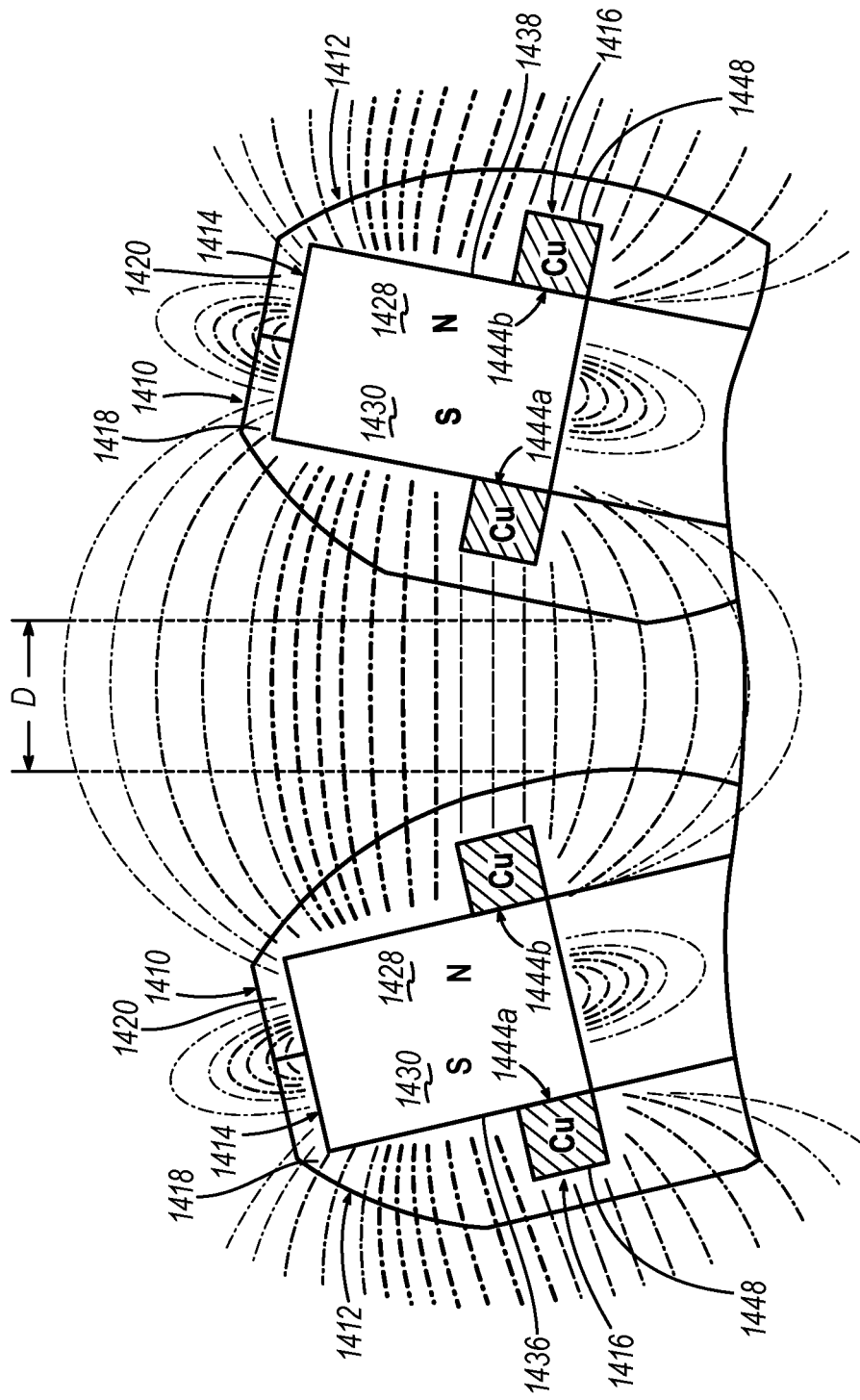
FIG. 26A depicts a schematic sectional view of a pair of third exemplary alternative beads generating magnetic fields in an open and expanded configuration, the beads being configured for use with the sphincter augmentation device of FIG. 3, where each bead includes a magnet and an exemplary non-magnetic feature.
Figure 26B:
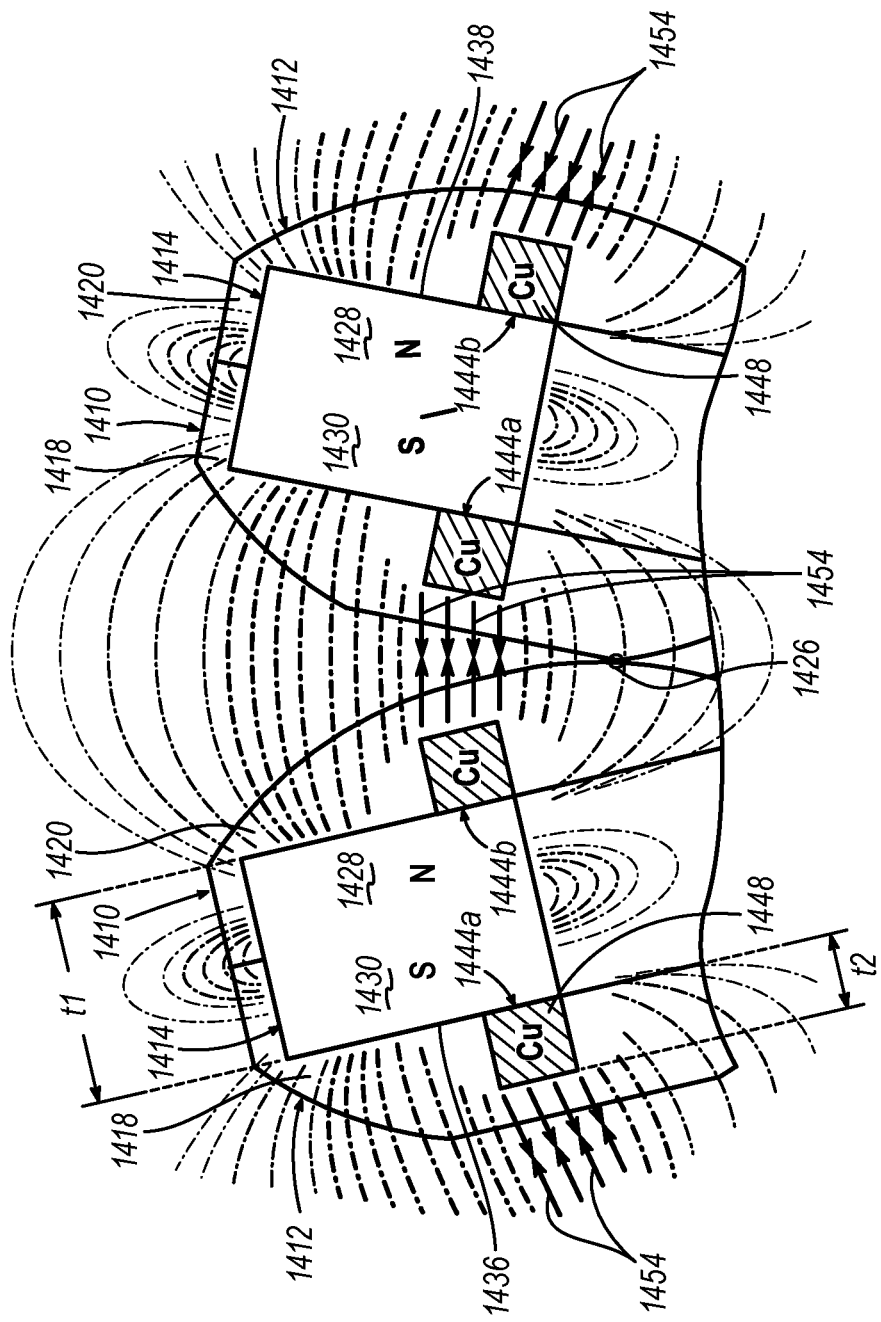
FIG. 26B depicts a schematic sectional view of the beads of FIG. 26A generating magnetic fields in a closed and contracted configuration.

FIGS. 26A-26B show exemplary alternative beads (1410) which may be used in place of beads (30) in device (20). Beads (1410) may also be used in place of, or incorporate aspects of, beads (30, 114a-l, 214a-k, 314a-l, 1010) of devices (20, 110, 210, 310). While not shown, beads (1410) may be linked together using links that may be similar to links (1211). Each bead (1410) includes a housing (1412), a magnet (1414), and a non-magnetic feature (1416). As shown schematically in FIGS. 26A-26B, beads (1410) include first and second housing portions (1418, 1420), which may be similar to first and second housing portions (1218, 1220), that collectively define a passageway and a magnet chamber. While not shown, the passageway may be similar to passageway (1222) and the magnet chamber may be similar to magnet chamber (1224). A contact surface (1426) is disposed between adjacent housings (1412) of beads (1410). Contact surfaces (1426) of adjacent beads (1410) are configured to selectively abut against each other in the contracted configuration.

Magnet (1414) may be similar to magnets (60, 118a-l, 218a-k, 610, 710, 810, 910, 1024). Magnet (1414) is configured to generate a magnetic field. The magnetic fields of adjacent magnets (1414) of beads (1410) are configured to proportionately change based on a distance (D) between adjacent beads (1410). The proportional change of the magnetic fields is based on cooperative engagement of the magnetic fields of magnets (1414). In other words, the cooperative engagement of the magnetic fields between adjacent beads (1410) changes proportionately with the proximity of adjacent beads (1410) from a fully expanded state to a close proximity state. The close proximity state is defined by adjacent magnets (1414) being separated by less than predetermined distance (D) (see FIG. 26A).

Figure 27:
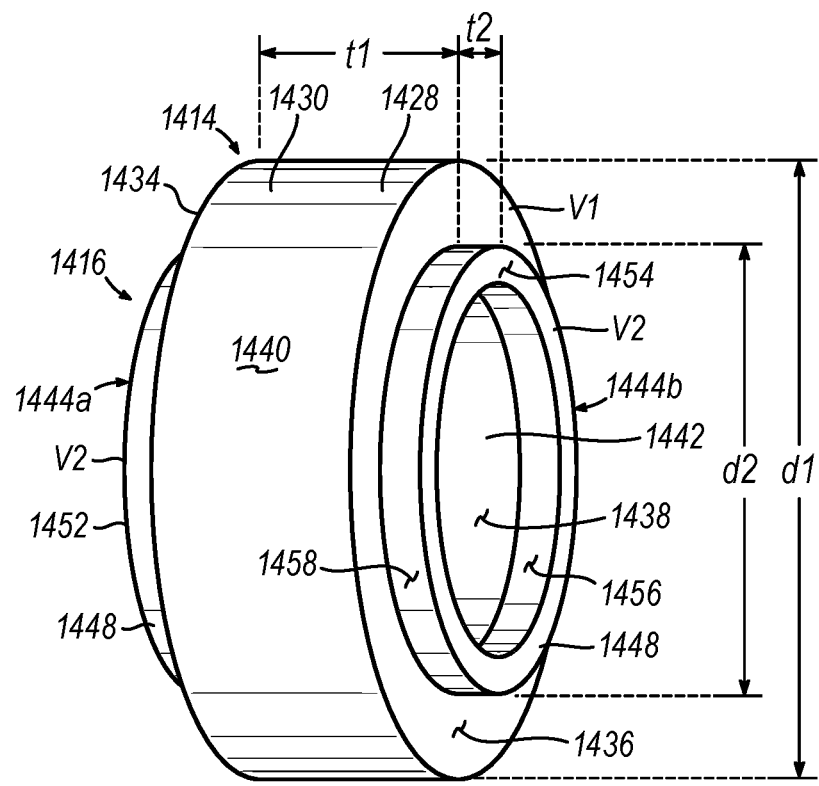
FIG. 27 depicts a perspective view of the magnet and the non-magnetic feature of FIG. 26A.
Figure 28:
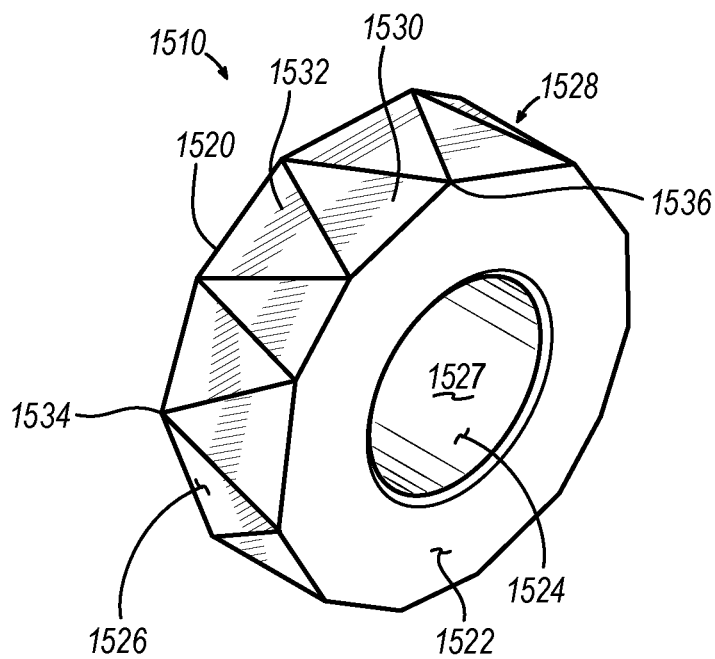
FIG. 28 depicts an exploded perspective view of an exemplary magnet and an exemplary ferromagnetic feature.

As shown in FIGS. 26A-26B, magnet (1414) includes a north pole portion (1428) and a south pole portion (1430). As shown in FIGS. 27-28, magnet (1414) includes a first flat magnet surface (1434), a second flat magnet surface (1436), an inner magnet surface (1438), and an outer magnet surface (1440). Inner magnet surface (1438) defines an aperture (1442). Second flat magnet surface (1436) is disposed opposite first flat magnet surface (1434). First flat magnet surface (1434) includes south pole portion (1430). Similarly, second flat magnet surface (1436) includes north pole portion (1428). Outer magnet surface (1440) is disposed between first and second flat magnet surfaces (1434, 1436). Outer magnet surface (1440) defines an outer perimeter of magnet (1414). Similar to magnet (1214), magnet (1414) has first size parameters, which may include a first diameter (d1), a first thickness (t1), and a first volume (V1).

Non-magnetic feature (1416) is disposed between and separates adjacent magnets (1414) of adjacent beads (1410). Non-magnetic feature (1416) is configured to create a temporary magnetic braking force by temporarily altering the proportionate change of the magnetic fields once adjacent beads (1410) are in a close proximity state. Non-magnetic feature (1416) creates this temporary magnetic braking force by inducing electron flow in non-magnetic feature (1416) disposed between adjacent magnets (1414) to reshape the magnetic fields of adjacent magnets (1414) of adjacent beads (1410). Non-magnetic feature (1416) is configured to create a bimodal distribution in the rate-of-change of the intensity of the magnetic fields with respect to the proximity of adjacent beads (1410). The bimodal distribution includes the constant rate and the decreased rate caused by the temporary magnetic braking force.

Non-magnetic feature (1416) may include at least one electrically conductive non-ferromagnetic spacer. As shown in FIGS. 26A-27, non-magnetic feature (1416) includes first and second electrically conductive non-ferromagnetic spacers (1444a-b). First and second electrically conductive non-ferromagnetic spacers (1444a-b) are in direct contact with magnet (1414). Magnet (1414) is interposed between first and second electrically conductive non-ferromagnetic spacers (1444a-b). As shown, first and second electrically conductive non-ferromagnetic spacers (1444a-b) include a first flat surface (1446), a second flat surface (1448), an inner surface (1450), and an outer surface (1452). Inner surface (1450) defines an aperture (1456). Second flat surface (1448) is disposed opposite first flat surface (1446). While first and second electrically conductive non-ferromagnetic spacers (1444a-b) are shown as including copper, at least one of first and second conductive non-ferromagnetic spacers (1444a-b) may alternatively or in addition to copper include gold, silver, or other nonferrous electrically conductive material. A combination of electrically conductive nonferrous materials may also be used for first and second conductive non-ferromagnetic spacers (1444a-b).

First and second electrically conductive non-ferromagnetic spacers (1444a-b) of non-magnetic feature (1416) have different thicknesses and outer diameters compared to magnet (1414). First and second electrically conductive non-ferromagnetic spacers (1444a-b) each have second size parameters, which may include a second diameter (d2), a second thickness (t2), and a second volume (V2). As shown in FIG. 27, first diameter (d1) is greater than second diameter (d2), first thickness (t1) is greater than second thickness (t2), and first volume (V1) is greater than second volume (V2). First and second electrically conductive non-ferromagnetic spacers (1444a-b) each have a second thickness (t2) that is at least half of the first thickness (t1) of magnet (1414). While first and second electrically conductive non-ferromagnetic spacers (1444a-b) are shown as the having the same shape and size parameters, first and second electrically conductive non-ferromagnetic spacers (1444a-b) may have different shapes and size parameters.

First and second electrically conductive non-ferromagnetic spacers (1444a-b) may allow for magnetic braking or temporary magnetic damping in the interaction between adjacent magnetic beads (1410) by the introduction of a non-magnetic electrically conductive metal element (e.g., first and second electrically conductive non-ferromagnetic spacers (1444a-b)) between the two paired magnetic elements (e.g., magnets (1414)). As the first magnet (1414) of a first bead (1410) induces an electrical field while the first magnet (1414) approaches a second magnet (1414) of a second bead (1410), the electrical movement of the electrons in a circular path (e.g., eddy currents) in spacers (1444a-b) creates a temporary magnetic field that slows the approach of the first magnet (1414) of the first bead (1410) towards the second magnet (1414) of the second bead (1410). The braking effect is produced by the eddy currents in first and second electrically conductive non-ferromagnetic spacers (1444a-b). The non-ferrous metal material of first and second electrically conductive non-ferromagnetic spacers (1444a-b) thus dampens and redirects the magnetic field. This can be seen by comparing the magnetic field of FIG. 21 regarding magnets (60) to FIG. 26B showing opposing arrows (of magnetic field causing a damping effect).

In addition to, or as an alternative to, using first and second electrically conductive non-ferromagnetic spacers (1444a-b), the above-described magnetic braking may be obtained by increasing the thickness of at least a portion of housing (1412). For example, housing (1412) may include an outer titanium wall having a non-uniform thickness. The secondary non-ferromagnetic feature (1416) may thus be defined by at least a portion of the titanium housing (1412) itself. In versions where a secondary non-ferromagnetic feature (1416) is defined by at least a portion of housing (1412), first bead (1410) may or may not include an additional electrically conductive non-ferromagnetic spacer such as spacers (1444a-b).

B. Exemplary Irregularly Shaped Magnet with Bimodal Distribution

FIG. 28 shows a magnet (1510) that may be incorporated into beads (30, 114a-l, 214a-k, 314a-l, 1010) of devices (20, 110, 210, 310). Magnet (1510) may be similar to magnets (60, 118a-l, 218a-k, 610, 710, 810, 910, 1024, 1214, 1414) described above. Similar to magnets (60, 118a-l, 218a-k, 610, 710, 810, 910, 1024, 1214, 1414), magnet (1510) includes a north pole portion and a south pole portion. Magnet (1510) includes a first flat magnet surface (1520), a second flat magnet surface (1522), an inner magnet surface (1524), and an outer magnet surface (1526). Inner magnet surface (1524) defines an aperture (1528). Second flat magnet surface (1522) is disposed opposite first flat magnet surface (1520). Outer magnet surface (1526) is disposed between first and second flat magnet surfaces (1520, 1522). Outer magnet surface (1526) defines an outer perimeter of magnet (1510).

As shown in FIG. 28, outer magnet surface (1526) includes a surface feature (1528). Irregular abrupt changes in surface feature (1528) of outer magnet surface (1526) cause abrupt changes in magnetic field intensity due to changes in distance between magnets (1510). In other words, the geometry of surface feature (1527) drives abrupt changes to the magnetic field. As shown, surface feature (1528) includes first and second pluralities of opposing angular features (1530, 1532). While opposing first and second pluralities of angular features (1530, 1532) are shown as opposing first and second pluralities of planar triangles, various other angular features are also envisioned. As shown, first plurality of angular features (1530) terminates at points (1534), and second plurality of angular features terminates at points (1536). First and second pluralities of angular features (1530, 1532) may be used to inverse the magnetic polarity at those locations to increase attraction or repel to change the effect of adjacent magnet (1510). Points (1534, 1536) have a magnetic flux that decreases at a greater rate than is more than distance based exponential decay. More or fewer points (1534, 1536) are also envisioned. First and second pluralities of angular features (1530, 1532) may include planar surfaces (1538).

C. Exemplary Ferromagnetic Surface Treatment with Bimodal Distribution

Figure 29:
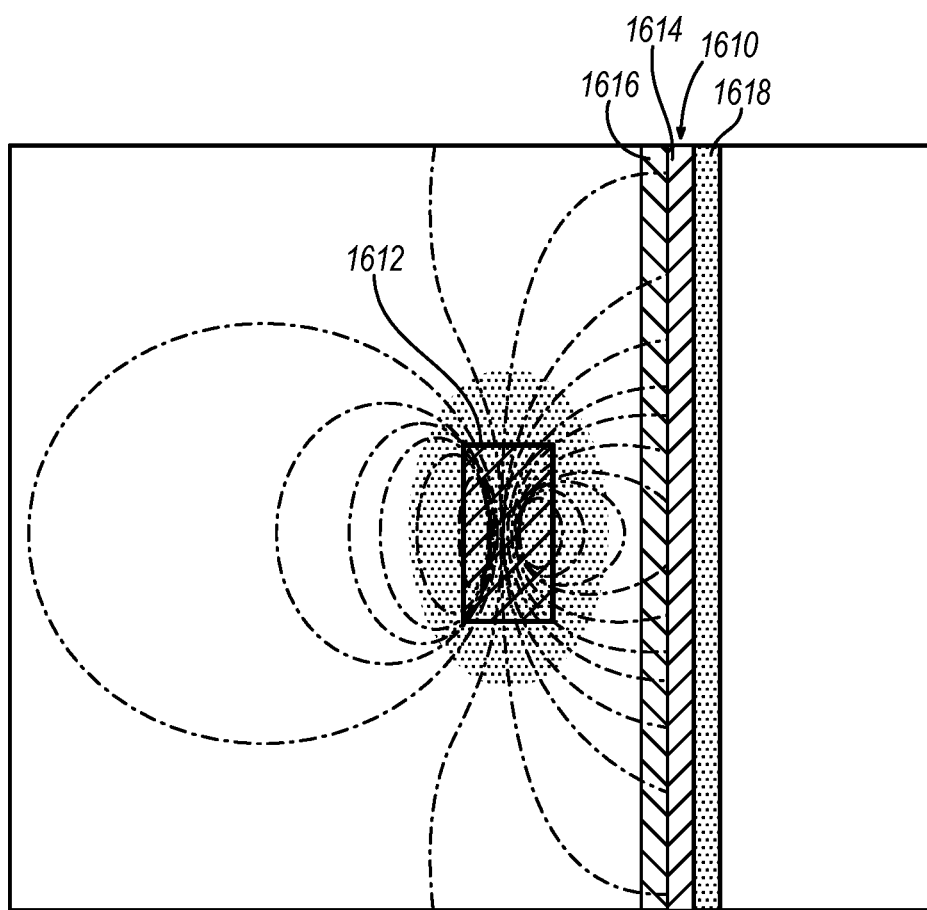
FIG. 29 depicts a schematic cross-sectional view of an exemplary magnet and another exemplary ferromagnetic feature.

FIG. 29 shows an exemplary ferromagnetic surface treatment (1610) that may be used together with beads (30, 114a-l, 214a-k, 314a-l, 1010) of devices (20, 110, 210, 310). Ferromagnetic surface treatment (1610) may alter the magnetic field by redirecting magnetic flux of a magnet (1612). Magnet (1612) may be similar to magnets (60, 118a-l, 218a-k, 610, 710, 810, 910, 1024, 1214, 1414, 1510). Ferromagnetic surface treatment (1610) may be coupled with a bead housing (1616), such as by being applied as a sleeve or other outer surface coating on the exterior of bead housing (1616). As shown, the magnetic field extends through bead housing (1616). Ferromagnetic surface treatment (1610) includes an externally located metal non-magnetic shielding (1614) to alter the magnetic fields as beads incorporating ferromagnetic surface (1610) move relative to each other. In other words, ferromagnetic surface treatment (1610) may adjust the magnetic field by shielding or intercepting and redirecting magnetic flux.

In some versions, ferromagnetic surface treatment (1610) includes Mu-metal and/or other ferromagnetic materials, and combinations thereof. Mu-metal is a nickel-iron soft ferromagnetic alloy with very high permeability, which may be used to shield against static or low-frequency magnetic fields. Ferromagnetic surface treatment (1610) may be woven to allow for expansion and contraction. Alternatively, ferromagnetic surface treatment (1610) may be oversized to allow expansion and contraction. A single side of ferromagnetic surface treatment (1610) is shown, with a protective coating (1618) being applied to the exterior of shielding (1614).

VI. EXAMPLES OF DEVICES WITH INTERACTIVE ADJACENT FIELD INTENSITY AND ANGULAR ORIENTATION BASED ON INTERCONNECTION LINK LENGTH

It may be beneficial to adjust the magnetic field strength between adjacent magnets (60) when device (20) moves from the contracted configuration of FIG. 5B to the expanded configuration of FIG. 5A. Particularly, it may be beneficial to control the expansion of adjacent beads (30) by adjusting the magnetic field strength between adjacent beads (30), so that beads (30) are pulled apart in response to dilation of the LES (6) in a more controlled manner. The following description provides examples of how beads (30) may be modified to provide adjustment of the magnetic field strength between adjacent beads (30), so that beads (30) are pulled apart in response to expansion of the LES (6) in a more controlled manner.

Figure 30:
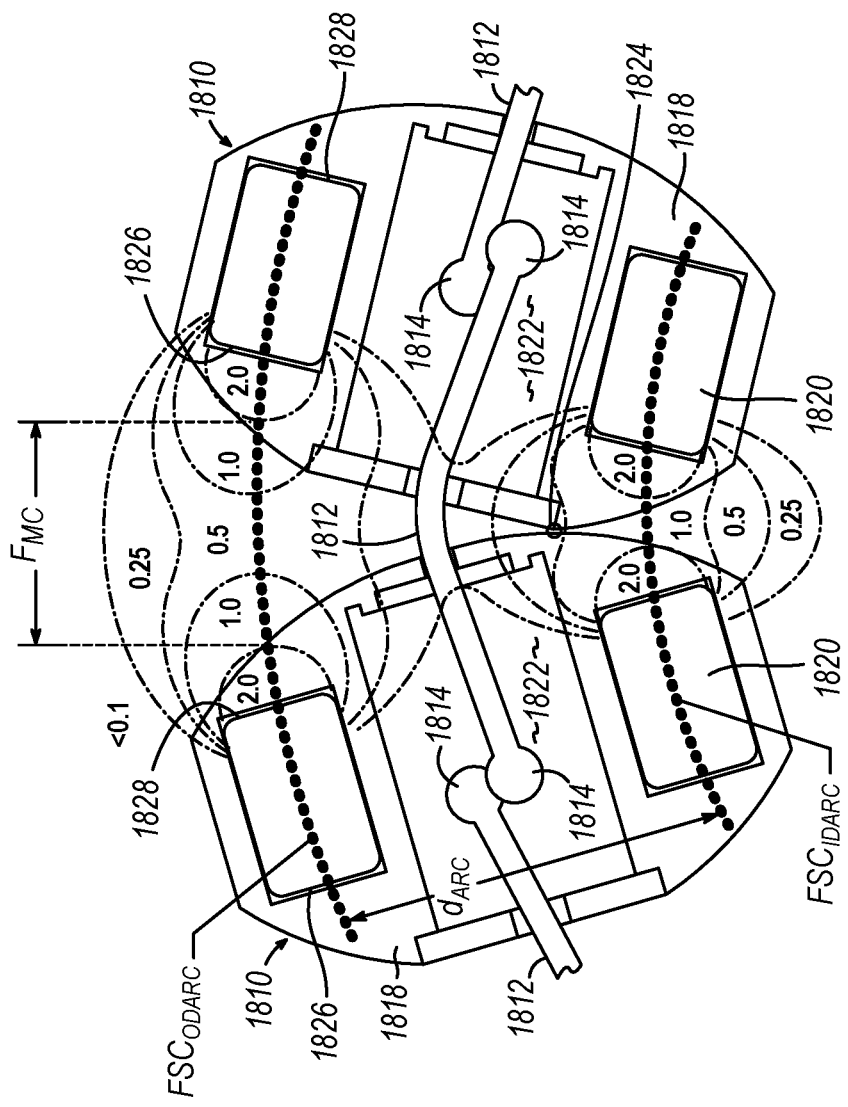
FIG. 30 depicts a schematic sectional view of a pair of fourth exemplary alternative beads generating magnetic fields in a closed and contracted configuration.
Figure 31:
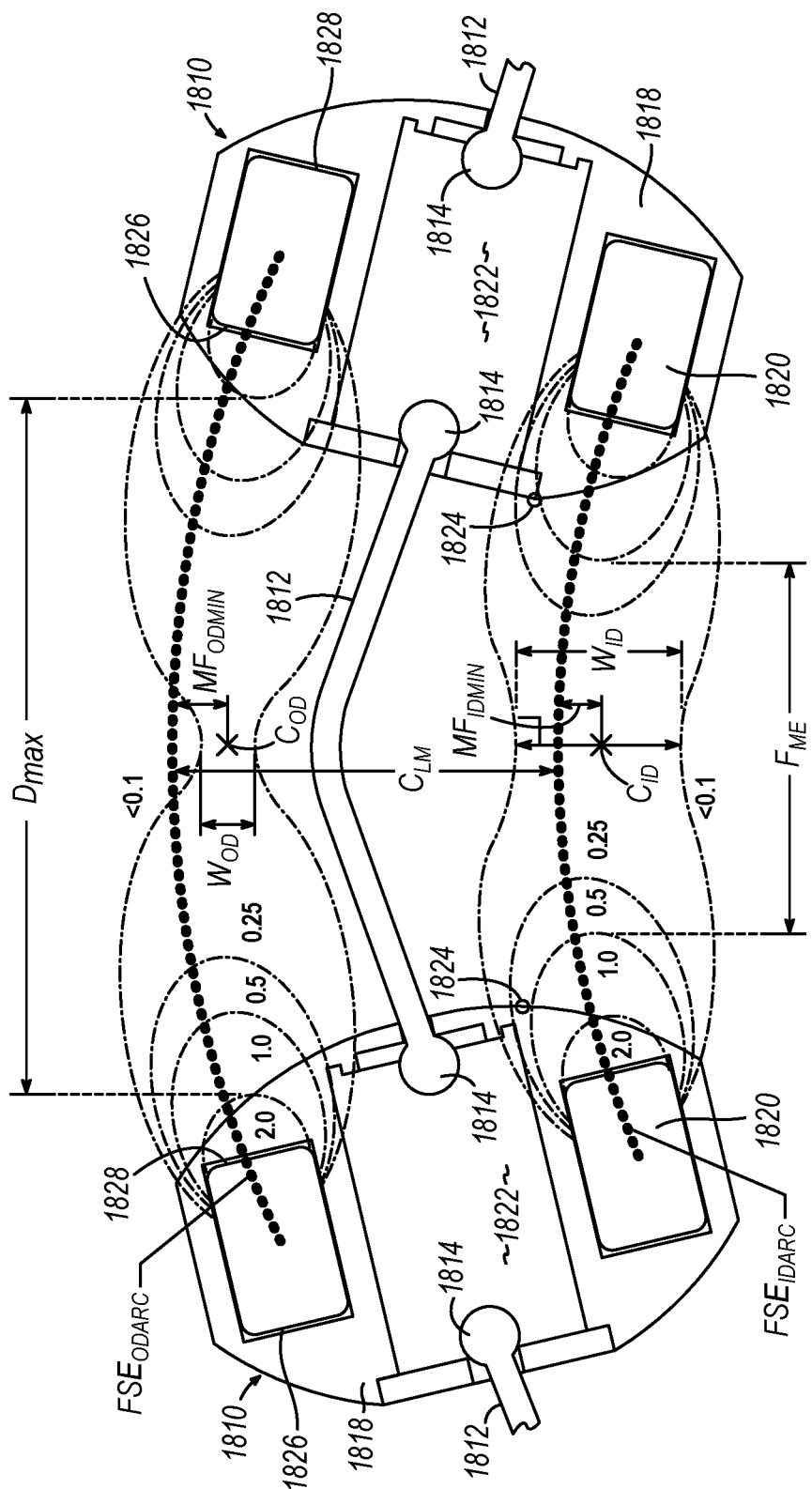
FIG. 31 depicts a schematic sectional view of the beads of FIG. 30 generating magnetic fields in an open and expanded configuration.
Figure 32:
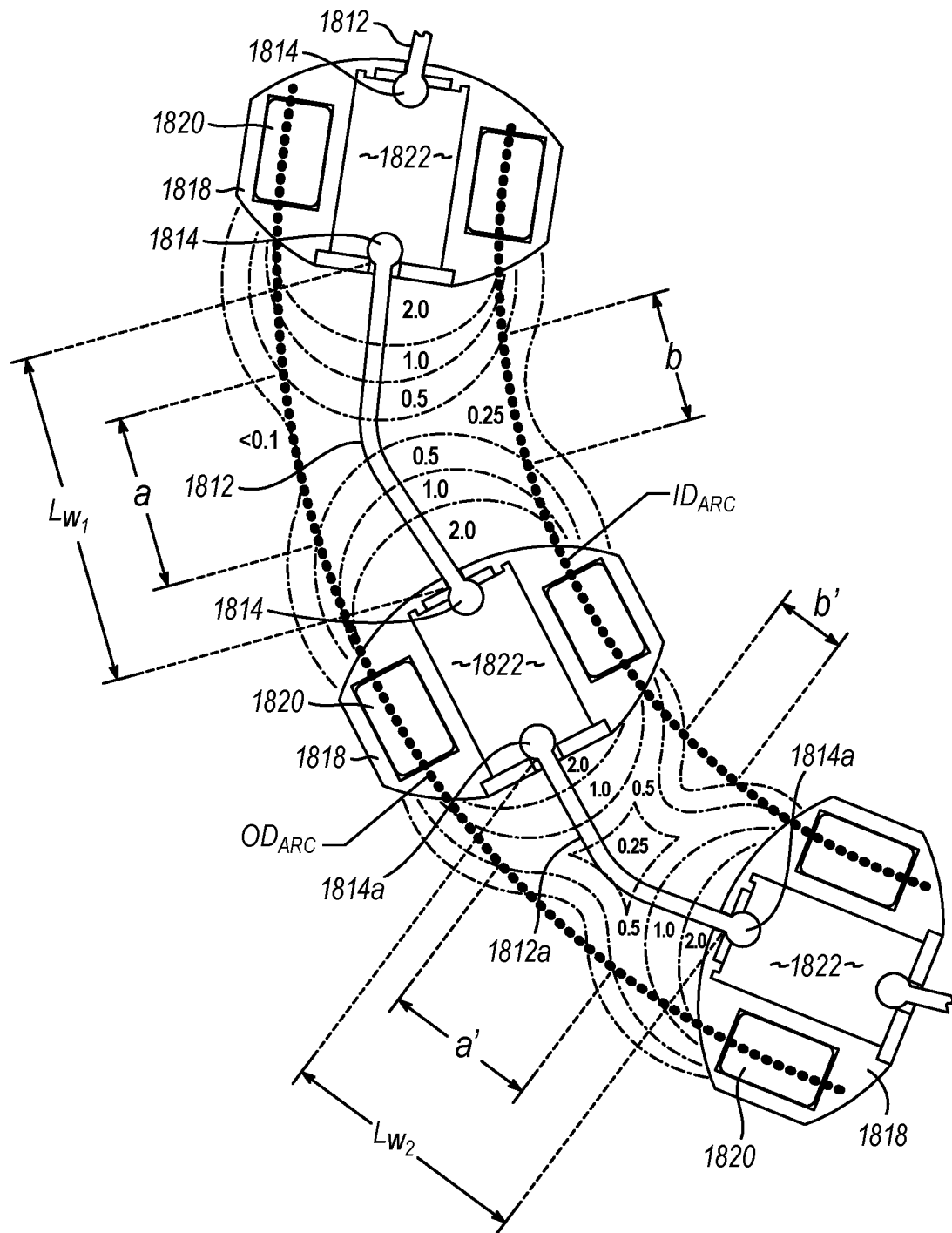
FIG. 32 depicts a schematic sectional view of the beads of FIG. 30 generating magnetic fields in a partially open and expanded configuration using first and second exemplary links.

FIGS. 30-32 show exemplary beads (1810) and exemplary links (1812, 1812a) which may be incorporated into devices (20, 110, 210, 310). The principles associated with beads (1810) may be used together with beads (30, 114a-l, 214a-k, 314a-l, 1010). Links (1812, 1812a) may be similar to links (40, 112, 1211). Adjacent beads (1810) are interconnected together using links (1812, 1812a). Each link (1812) includes retention features (1814, 1814a) (shown as ball tips (44)) positioned at opposing terminal ends of link (1812) that mechanically constrain the expanded configuration to prevent further expansion of the annular arrangement beyond the expanded configuration.

Beads (1810) may be arranged in an annular arrangement to encircle a sphincter such as the LES (6). Each bead (1810) includes a housing (1818) and at least one magnet (1820) configured to generate a magnetic field. Magnet (1820) may be similar to magnets (60, 118a-l, 218a-k, 610, 710, 810, 910, 1024, 1214, 1414, 1510, 1612). Housing (1818) forms a passageway (1822) that extends through housing (1818). Housing (1818) includes a contact surface (1824) disposed between beads (1810). Magnet (1820) is disposed around passageway (1822). Magnet (1820) may have a variety of suitable shapes and sizes. Magnets (1820) include opposing first and second magnet faces (1826, 1828).

In FIGS. 30-32, the 1.0 value region represents 100% of the ideal magnetic strength of device (20). The 2.0 value region represents 200% of the ideal magnetic strength of device (20), the 0.5 value region represents 50% of the ideal magnetic strength of device (20), the 0.25 value region represents 25% of the ideal magnetic strength of device (20), the 0.1 value region represents 10% of the ideal magnetic strength of device (20), and the <0.1 value region represents less than 10% of the ideal magnetic strength of device (20).

The annular arrangement is configured to move between a contracted configuration shown in FIG. 30, where adjacent beads (1810) are in contact with each other, and an expanded configuration shown in FIG. 31, where adjacent beads (1810) are spaced apart from each other. In the contracted configuration of FIG. 30, adjacent magnets (1820) define a contracted inner diameter arc ($FSC_{IDARC}$) and a contracted outer diameter arc ($FSC_{ODARC}$). An arc distance ($d_{ARC}$) separates contracted inner and outer diameter arcs ($FSC_{IDARC}$, $FSC_{ODARC}$). Intersections of housings (1818) and contracted outer diameter arc ($FSC_{ODARC}$) define a contracted spread distance ($F_{MC}$) between adjacent beads (1810). In some versions, the minimum threshold is at least about half of a contracted width of the magnetic field of magnets (1820) of adjacent beads (1810) in the contracted configuration. The minimum constraint state has both an inner diameter interactive field and an outer diameter interactive field, where the full couple covers the width between the inner diameter inside surface and the outer diameter outside surface. The geometric opening between beads (1810) when in physical contact and the distance of the magnetic gap define the force in contracted configuration. FIG. 30 shows beads (1810) physically contacting each other at contact surface (1824), the distance ($F_{MC}$) defines the magnetic force. The force at contracted inner diameter arc ($FSC_{IDARC}$) is greater than the force at contracted outer diameter arc ($FSC_{IDARC}$) based on separation distance between adjacent magnets (1820).

In moving from the contracted configuration of FIG. 30 to the expanded configuration of FIG. 31, magnetic fields of magnets (1820) of adjacent beads (1810) are configured to magnetically interact until magnets (1820) are separated beyond a minimum threshold. The minimum threshold defines a maximum allowable expansion of the annular arrangement while maintaining interaction between magnetic fields of magnets (1820) of adjacent beads (1810). The minimum threshold for the interactive adjacent magnetic field intensity and magnetic field angular orientation may be based on the maximum length of the link (1812). The minimum threshold has sufficient cooperative intensity to allow magnets (1820) forming adjacent magnetic fields to provide a magnetic pulling force relative to the weight of beads (1810) and the friction of links (1812). In other words, the minimum threshold is the maximum length that defines the minimum strength to magnetically bias adjacent beads (1810) towards each other while overcoming the weight of beads (1810) and the friction of links (1812). In FIG. 31, the width of the magnetic field is defined as the perpendicular distance between first and second lines that are parallel to a portion of the magnetic field where inside and outside collinear surfaces and the width is between the first and second lines. In other words, the thickness measure is defined as line parallel to the portion of the magnetic field where the inside and outside collinear surfaces and the width is between the first and second lines.

In the expanded configuration of FIG. 31, adjacent magnets (1820) define an expanded inner diameter arc ($FSE_{IDARC}$) and an expanded outer diameter arc ($FSE_{ODARC}$). Expanded outer diameter arc ($FSE_{ODARC}$) defines a maximum spread distance ($D_{MAX}$) between adjacent beads (1810). Expanded inner diameter arc ($FSE_{ODARC}$) is disposed closer to a center point (not shown, but similar to centerpoint (C) in FIGS. 6A-6C) of the annular arrangement than expanded outer diameter arc ($FSC_{ODARC}$). An intensity and an angular orientation of the interacting magnetic fields may be based on chord lengths ($L_{W1}$, $L_{W2}$) of links (1812, 1812a). Particularly, link (1812) has a chord length ($L_{W1}$) that is greater than chord length ($L_{W2}$) of link (1812a). The geometric centerline formed between adjacent magnets (1820) may be compared against a magnetic field centerline formed by magnetic fields of adjacent magnets (1820). For example, the minimum full extent of magnetic field strength and the X-shaped orientation is proportionate to chord lengths ($L_{W1}$, $L_{W2}$) of links (1812, 1812a). The maximum expansion state has a collapsed cooperative field where expanded outer diameter arc ($FSE_{ODARC}$) of adjacent magnets (1820) exhibit a dual magnetic. For expanded inner diameter arc ($FSE_{ODARC}$) the cooperative field collapses into a single magnetic field in an X-shaped manner.

With continued reference to FIG. 31, the minimum attractive field is related to the maximum length between adjacent beads (1810). This maximum length is limited by chord lengths ($L_{W1}$, $L_{W2}$) of links (1812, 1812a). This monitors magnetic field collapse to control a minimum width. Expanded outer diameter arc ($FSE_{ODARC}$) defines an outer diameter width ($W_{OD}$) at a position equidistant between beads (1810). Outer diameter width ($W_{OD}$) at the position equidistant between beads (1810) has an outer diameter center ($C_{OD}$). The distance between expanded outer diameter arc ($FSE_{ODARC}$) and outer diameter center ($C_{OD}$) is shown as a distance ($MF_{ODMIN}$). Similarly, expanded inner diameter arc ($FSE_{IDARC}$) defines an expanded inner diameter width ($W_{ID}$). Expanded inner diameter width ($W_{ID}$) is measured from a vector direction of the magnetic fields that is substantially perpendicular to the magnet faces. Expanded inner diameter width ($W_{ID}$) at the position equidistant between beads (1810) has an inner diameter center ($C_{ID}$). The distance between expanded inner diameter arc ($FSE_{IDARC}$) and inner diameter center ($C_{ID}$) is shown as a distance ($MF_{IDMIN}$).

With continued reference to FIG. 31, expanded outer diameter width ($W_{OD}$) of the expanded inner magnetic field is greater than expanded inner diameter width ($W_{ID}$) of the expanded outer magnetic field. In other words, the width of the magnetic field in the expanded configuration is defined by the vector direction of the interactive substantially perpendicular to flat magnet faces (1826, 1828). The vector direction is angled between about 80 degrees and about 90 degrees relative to flat magnet faces (1826, 1828) of adjacent magnets (1820).

As shown in FIG. 31, a ratio may be defined by at least one of a shape or an intensity of the adjacent magnetic fields when a version of device (20) incorporating beads (1810) is in the expanded configuration relative to at least one of the shape or strength of the adjacent magnetic fields when a version of device (20) incorporating beads (1810) is in the contracted configuration. This ratio may be used to determine the maximum allowable magnetic expansion. By way of example only, the force of contracted magnetic field ($F_{MC}$) between adjacent beads (1810) in the contracted configuration shown in FIG. 30 may be between about 1.5 to about 4 times greater than the force of expanded magnetic field ($F_{ME}$) between adjacent beads (1810) in the expanded configuration shown in FIG. 31. In some versions, the force of the contracted magnetic field ($F_{MC}$) between adjacent beads (1810) in the contracted configuration is between about 2 and about 3 times greater that the force of expanded magnetic field (FE) between adjacent beads (1810) in the expanded configuration. Magnetic field intensity is exponentially related to distance. For example, the expanded configuration versus the contracted configuration at the inner diameter may be shown by the expression $4\times\text{-}6\times FSE_{IDARC}$ which is greater than or equal to $FSC_{IDARC}$. The 4×-6× may refer to the intensity change in the magnetic fields as beads (1810) move from the expanded configuration to the contracted configuration.

FIG. 32 shows a schematic sectional view of beads (1810) in the expanded configuration. This maximum length is limited by chord lengths ($L_{W1}$, $L_{W2}$) of links (1812, 1812a). A distance (a) refers to the distance along outer diameter arc ($OD_{ARC}$) regarding link (1812), a distance (b) refers to the distance along inner diameter arc ($ID_{ARC}$) regarding link (1812), a distance (a') refers to the distance along outer diameter arc (OD$_{ARC}$) regarding link (1812*a*), and a distance (b') refers to the distance along inner diameter arc (ID$_{ARC}$) regarding link (1812*a*). A comparison of distance (a) and distance (b) shows that distance changes intensity of the magnetic field. Similarly, a comparison of distance (a') and distance (b') shows that distance changes based on the intensity of the magnetic field. A comparison of distance (a) to distance (a') shows that distance changes based on chord lengths (L$_{W1}$, L$_{W2}$) of links (1812, 1812*a*). Similarly, a comparison of distance (b) to distance (b') shows that distance changes based on chord lengths (L$_{W1}$, L$_{W2}$) of links (1812, 1812*a*).

Figure 33:
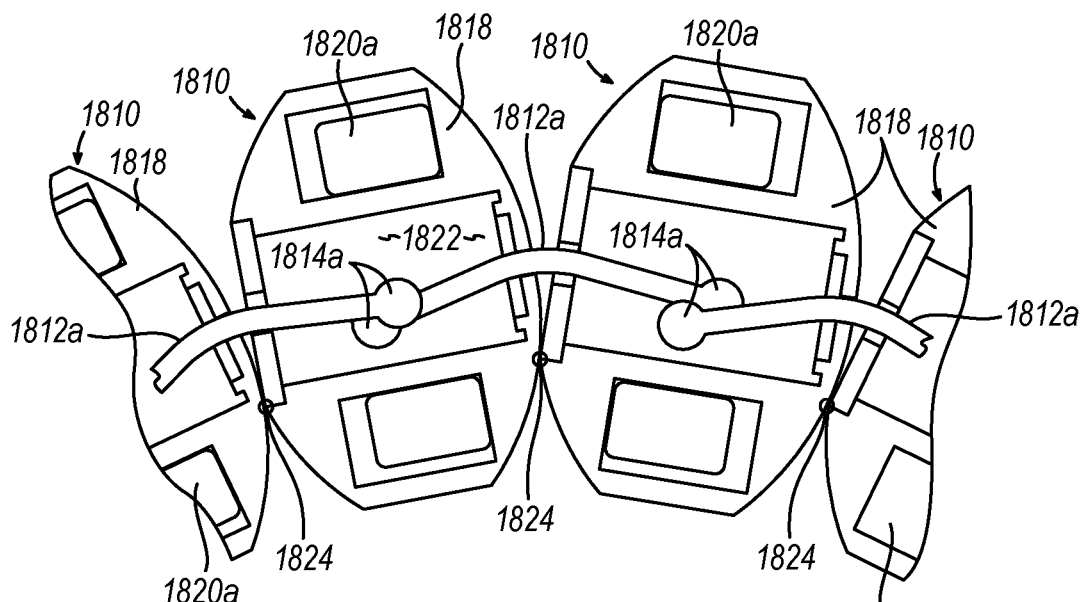
FIG. 33 depicts a schematic sectional view of an example of a variation of the beads of FIG. 30, where magnets of the adjacent beads move within the housing in the contracted configuration.
Figure 34:
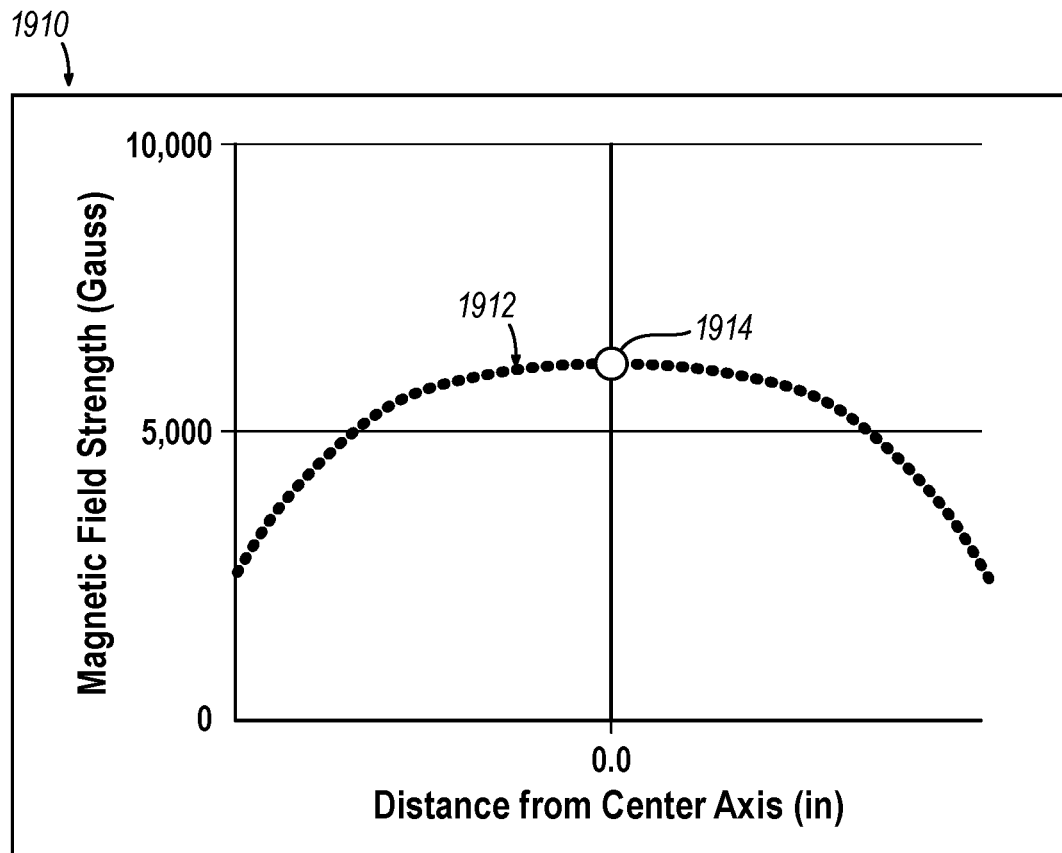
FIG. 34 depicts a graph of a plot of the magnetic field strength relative to a distance from the center axis for the beads of FIG. 33 in the contracted configuration.

FIGS. 33-36 show how the magnetic field strength changes based on a distance to a center axis (i.e., the geometric centerline between magnets (1820*a*)) for the contracted configuration and the expanded configuration. FIG. 33 shows a schematic sectional view of beads (1810) of FIG. 30, where magnets (1820*a*) of adjacent beads (1810) move within housings (1818) in the contracted configuration. FIG. 34 shows an exemplary graph (1910) of a plot (1912) of the magnetic field strength relative to a distance from the center axis for beads (1810) of FIG. 33 in the contracted configuration. Plot (1912) generally forms an inverse parabolic shape with a vertex (1914) located at zero inches from the center axis.

Figure 35:
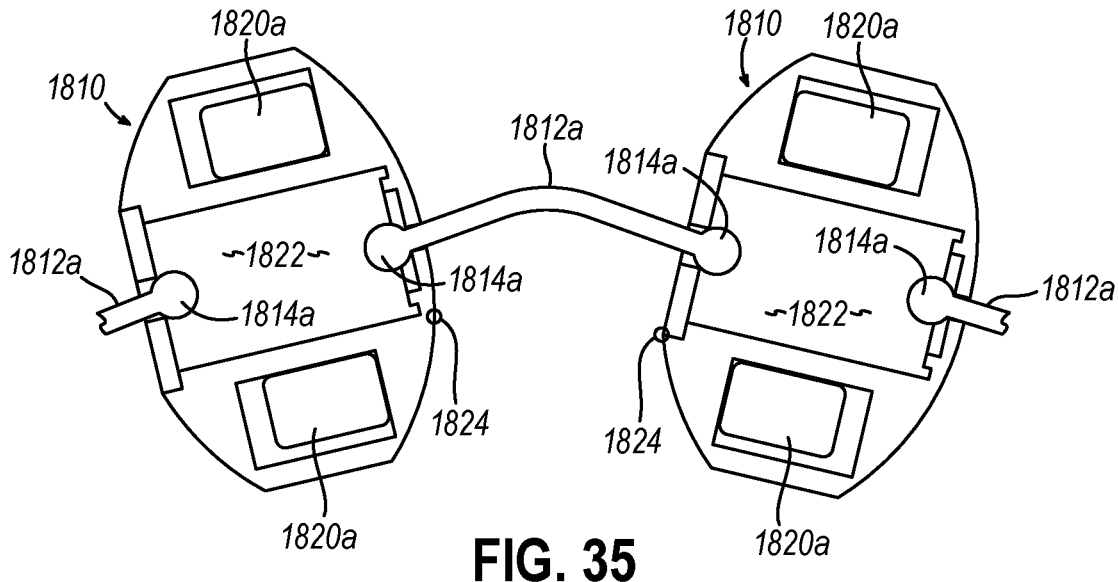
FIG. 35 depicts a schematic sectional view of the beads of FIG. 33, where the magnets move within the housing in the expanded configuration.
Figure 36:
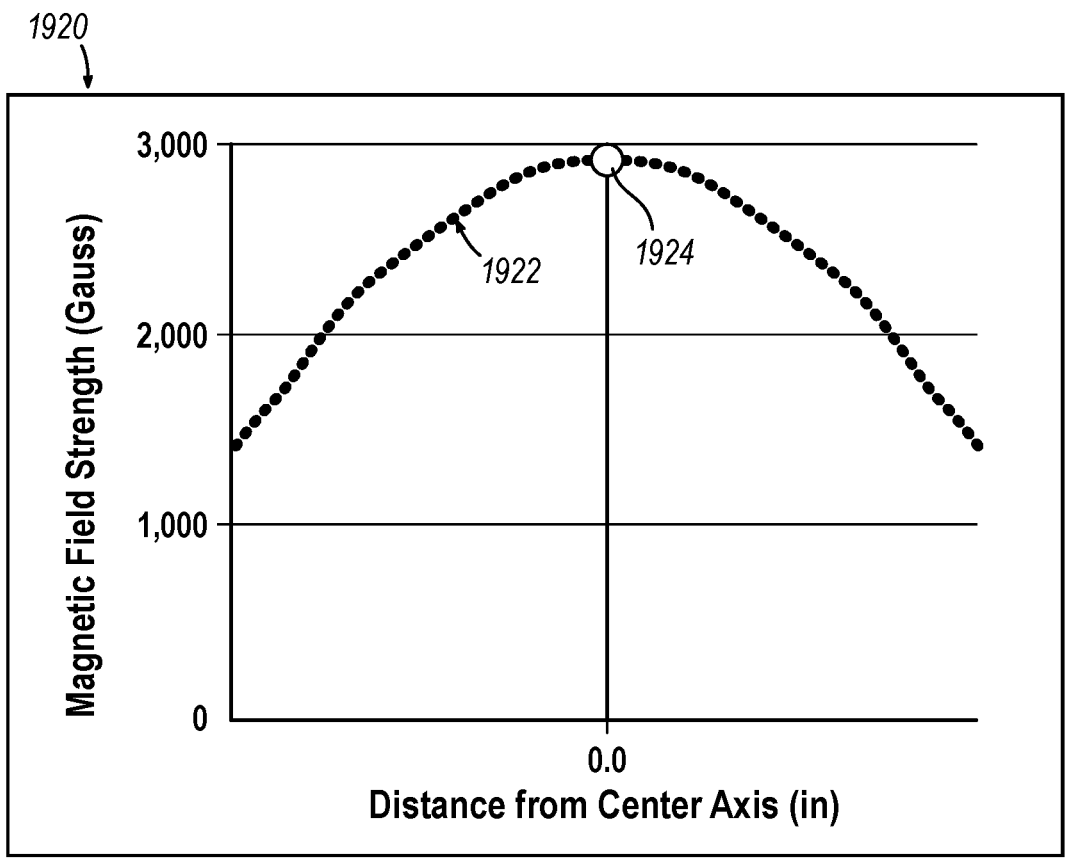
FIG. 36 depicts a graph of an exemplary plot of the magnetic field strength relative to a distance between the beads of FIG. 33 in the expanded configuration.

FIG. 35 shows a schematic sectional view of beads (1810) of FIG. 30, where magnets (1820*a*) move within housing (1818) in the expanded configuration. In FIG. 35, beads (1810) are separated by chord length of links (1812*a*). FIG. 36 shows a graph (1920) of a plot (1922) of the magnetic field strength relative to a distance that beads (1810) of FIG. 35 in the expanded configuration. Plot (1922) generally forms an inverse parabolic shape with a vertex (1924) located at zero inches from the center axis. Plots (1912, 1922) depict the magnetic field strength in the vertical direction along a line that is equidistant between magnet (1820*a*).

Figure 37:
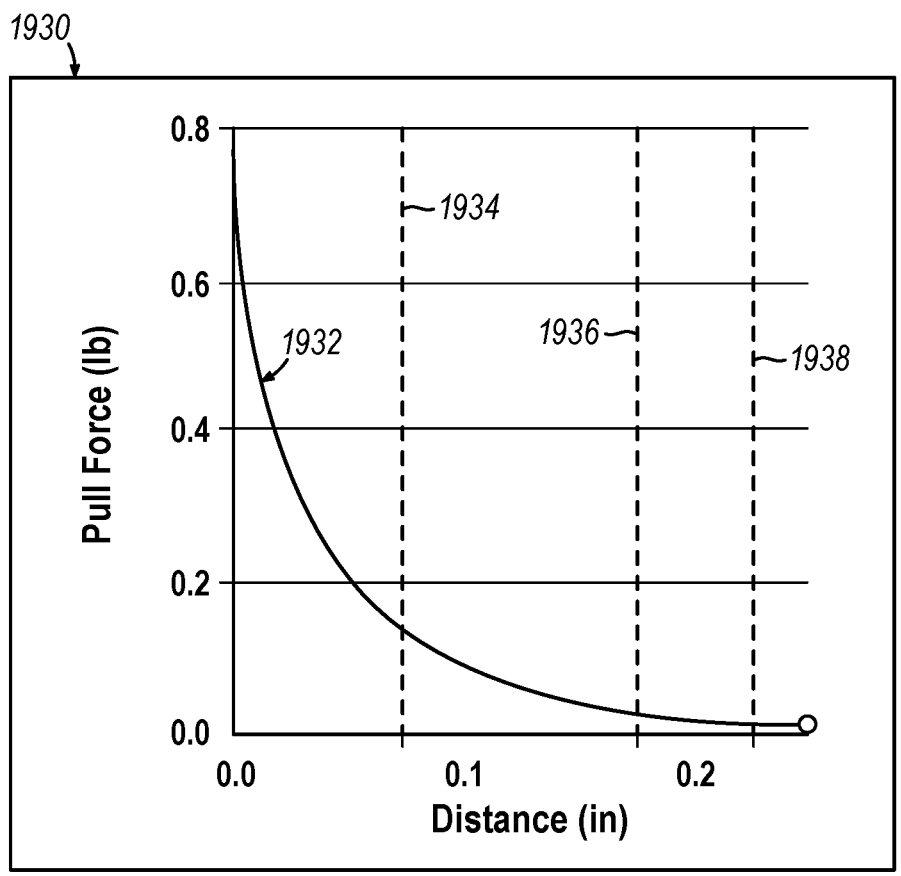
FIG. 37 depicts a graph of a plot of the pull force relative to a distance from the center axis for the beads of FIG. 33.

FIG. 37 shows a graph (1930) of a plot (1932) of a pull force relative to a distance from the center axis for beads (1810) of FIG. 33. The magnetic field strength may be unique to the size, thickness, shape, and material for each magnet (1820). The pull force is reduced the further magnets (1820, 1820*a*) are separated from each other, until a predetermined distance is satisfied, at which time the attraction force is exceeded and magnets (1820) are not reattracted to each other. In FIG. 37, the vertical lines refer to a magnetic pull force of a minimum inner diameter (1934), a magnetic pull force of a maximum inner diameter (1936), and a magnetic pull force that exceeds the minimum threshold (1938).

VII. EXAMPLES OF DEVICES WITH BIMODAL DISTRIBUTION OF MAGNETIC FIELD INTENSITY RATE-OF-CHANGE WITH SHELL-TO-SHELL ORIENTATION CONTROLLED BY FIELDS OF ADJACENT MAGNETS

It may be desirable to control the angular orientation of housings (32, 34) of adjacent beads (30) relative to a centerpoint (C) (see FIG. 3) of the annular arrangement to balance the magnetic fields of adjacent magnets (60) disposed within housings (32, 34) of adjacent beads (30). The angular orientation of housings (32, 34) may affect the cumulative magnetic field strength of adjacent beads (30). The following description provides examples of how beads (30) may be modified to provide control of the angular orientation of housings (32, 34), so that the magnetic fields of magnets (60) in adjacent beads (30) are better balanced throughout the annular arrangement.

FIGS. 38-41 show an exemplary sphincter augmentation device (2210), which may be similar to device (110) described above, with differences described below. Device (2210) includes at least one link (2212), a plurality of beads (2214*a-p*), and first and second coupling features (2216, 2218). Links (2212) may be substantially similar to links (112), and beads (114*a-l*) may be similar to beads (114*a-l*) described above. First and second coupling features (2216, 2218) selectively couple together to secure device (2210) in an annular arrangement. The annular arrangement is configured to move between a contracted configuration and an expanded configuration.

Figure 39:
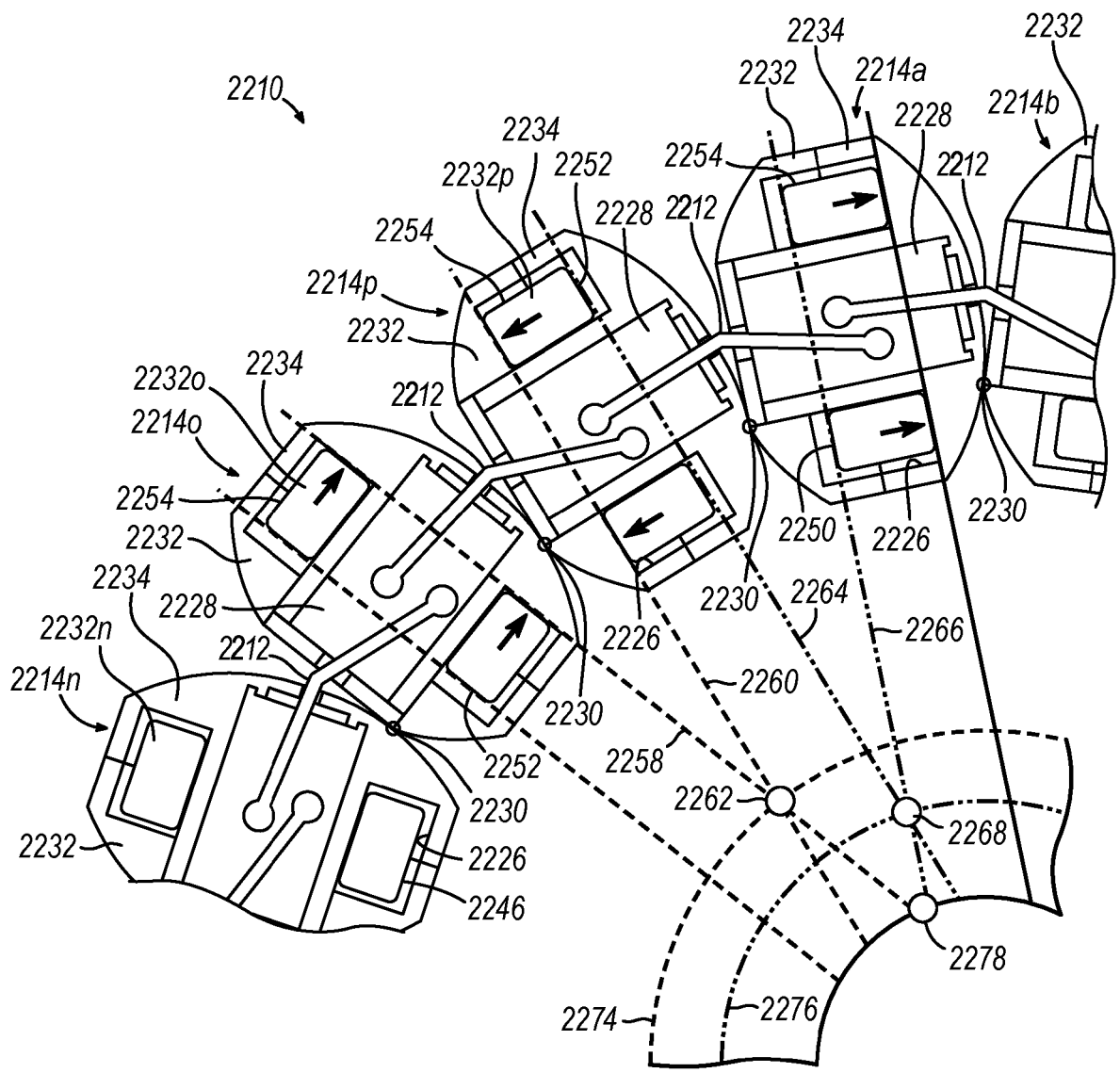
FIG. 39 depicts a partial schematic cross-sectional view of a portion of the sphincter augmentation device of FIG. 38.

Beads (2214*a-p*) are joined together using links (2212). While sixteen individual beads (2214*a-p*) are shown, more or fewer beads (2214*a-p*) are envisioned. Beads (2214*a-p*) include respective housings (2220). As shown in FIG. 39, each housing (2220) includes first and second housing portions (2222, 2224). Housings (2220) each include a magnet chamber (2226) and a passageway (2228) extending through housing (2220). Each housing (2220) includes a contact surface (2230). Contact surfaces (2230) of adjacent beads (2214*a-p*) are configured to abut against each other in the contracted configuration. At least one magnet (2232*a-p*) is sized and configured to be received within respective magnet chambers (2226) of housings (2220) may be similar to magnets (60, 118*a-l*). Magnets (2232*a-p*) are shown as a magnet disposed around passageway (2228). Magnets (2232*a-p*) are configured to generate a magnetic field. Magnets (2232*a-p*) are sized and configured to move within respective magnet chambers (2226). First coupling feature (2216) includes a magnet (2234). Similarly, second coupling feature (2218) includes a magnet (2236).

A consistent angular orientation of adjacent housings (2220) in the annular arrangement is determined by at least one adjustment parameter. The adjustment parameters include a directionality of the adjacent magnets (2232*a-p*) within magnet chambers (2226), a freedom of magnets (2232*a-p*) to move within magnet chambers (2226), and a magnitude of the magnetic fields of adjacent magnets (2232*a-p*). In other words, the angular orientation consistency between adjacent housings (2220) may be shifted using any of the adjustment parameters alone or in combination with another adjustment parameter. In some versions, the consistent angular orientation of adjacent housings (2220) in the annular arrangement is determined by at least two, or each, of the adjustment parameters shown and described herein.

Magnetic vector directional flow may be dependent on one or more of the following: the concentricity of magnets (2232*a-p*) within housings (2220), the lateral clearance within housing (2220), and/or the equality of the magnet strength of each of adjacent magnets (2232*a-p*) each of which will be discussed in detail below. Consistency in the magnetic vector field between adjacent magnets (2232*a-p*) may result in uniform annular arrangement of housings (2220) in the contracted state. In some instances, localized bunching of housings (2220) may provide a non-uniform annular arrangement. In some instances, localized bunching may cause a non-circular shaped restriction (e.g., a triangular shaped restriction). Avoiding bunching of housings (2220) in the contracted state may provide a uniform annular arrangement whereby housings (2220) are angularly spaced apart from each other equidistantly when device (2210) is in the contracted state.

Figure 40:
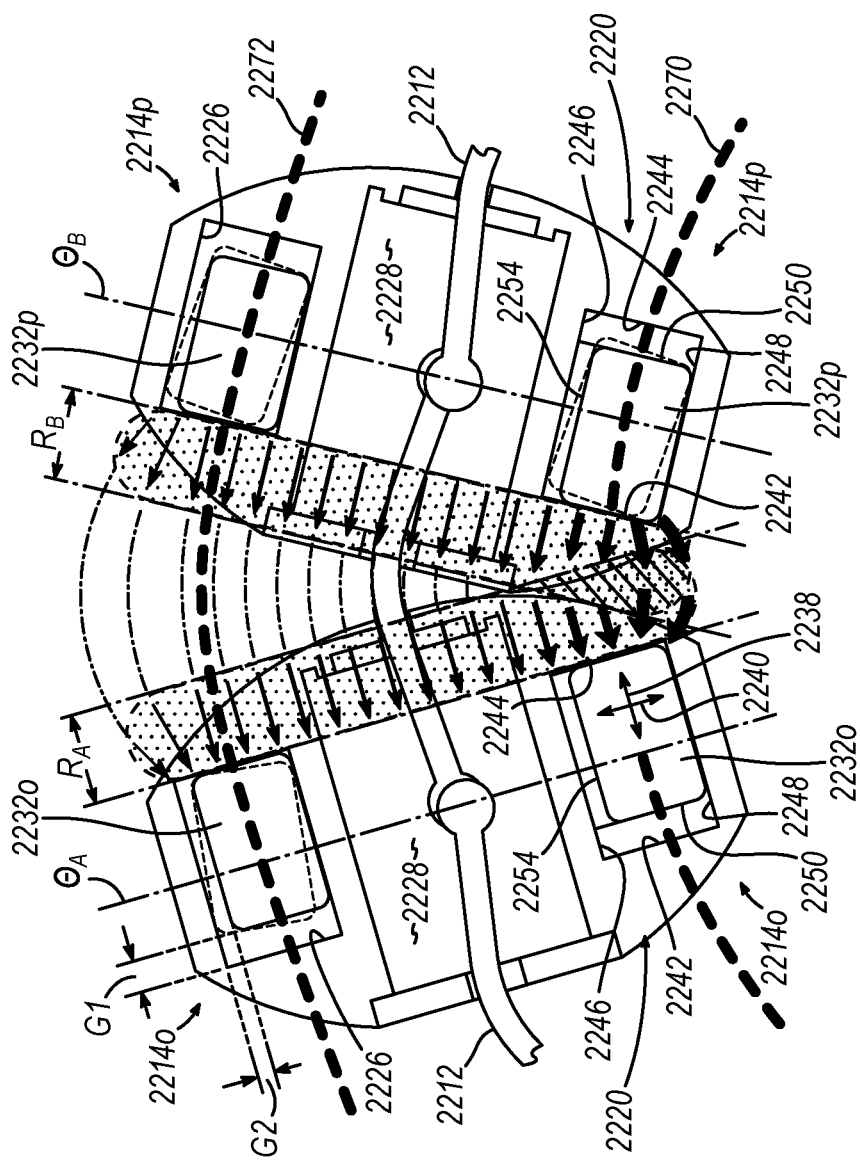
FIG. 40 depicts a partial schematic cross-sectional view of a portion of the sphincter augmentation device of FIG. 38 generating magnetic fields.

The freedom of magnets (2232a-p) to move within magnet chambers (2226) may include lateral movement of magnets (2232a-p) along first and second orthogonal dimensions (see arrows (2238, 2240) in FIG. 40) to maintain the consistent angular orientation. As shown in FIG. 40, magnet chamber (2226) includes a first lateral interior surface (2242), a second lateral interior surface (2244), an inner interior surface (2246), and an outer interior surface (2248). Second lateral interior surface (2244) is disposed opposite first lateral interior surface (2242). Inner interior surface (2246) is disposed between first and second lateral interior surfaces (2242, 2244). Outer interior surface (2248) is disposed between first and second lateral interior surfaces (2242, 2244) and opposite to inner interior surface (2246). Magnets (2232a-p) are configured to move laterally within magnet chamber (2226) through a first gap (G1) between first and second lateral interior surfaces (2242, 2244) to maintain the consistent angular orientation. Similarly, magnet (2232a-p) is configured to move radially (in a radial direction relative to a centerpoint (C) of annular arrangement) through a second gap (G2) within magnet chamber (2226) between inner and outer interior surfaces (2246, 2248) to maintain the consistent angular orientation. Magnets (2214a-p) include a first flat magnet surface (2250), a second flat magnet surface (2252), an inner magnet surface (2254), and an outer magnet surface (2256).

Figure 38:
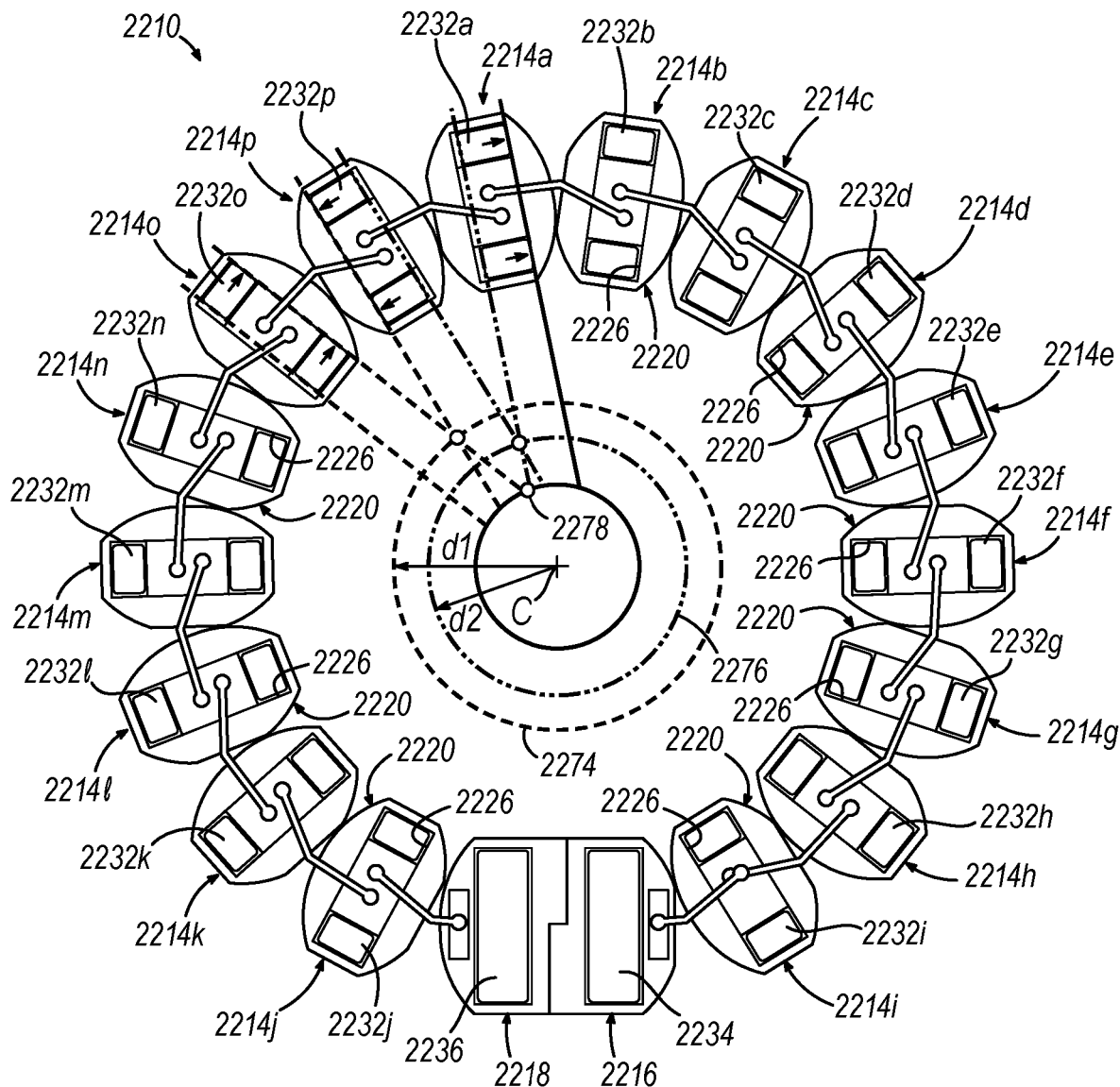
FIG. 38 depicts a top schematic cross-sectional view of a fourth exemplary alternative sphincter augmentation device in a closed and contracted configuration.

Stronger pairs of magnets (2214a-p) move to a common side of housings (2220), and weaker pairs of magnets (2214a-p) get pulled along based on the direction of the stronger magnet (2214a-p) sets. Regarding the annular arrangement shown in FIGS. 38-39, magnet (2232o) is laterally shifted toward bead (2114p) and away from bead (2114n). Similarly, magnet (2232p) is laterally shifted toward bead (21140) and away from bead (2114a). Similarly, magnet (2232a) is laterally shifted toward bead (2114b) and away from bead (2114p). As shown in FIGS. 38-39, a line (2258) is formed along a second lateral side of magnet (2232o) that intersects with a line (2260) formed along a first lateral side of magnet (2232p) at a first intersection point (2262). Similarly, a line (2264) formed along a second lateral side of magnet (2232p) that intersects with a line (2266) formed along a first lateral side of magnet (2232a) at a second intersection point (2268).

The consistent angular orientation may be measured using intersection points (e.g., first and second intersection points (2262, 2268)) of adjacent magnets (2232a-p). The intersection points for each of magnets (2232a-p) of the annular arrangement may be within a predetermined range maintain the consistent angular orientation. In other words, consistency of the annular arrangement may be measured using intersection points (e.g., intersection points (2262, 2268)) of adjacent magnet faces. As shown in FIG. 38, first intersection point (2262) is a first distance (d1) from centerpoint (C) of the annular arrangement. Similarly, second intersection point (2268) is a second distance (d2) from centerpoint (C) of the annular arrangement. As shown, the first and second distances (d1, d2) are different. The first and second distances (d1, d2) are within a predetermined range for each of the radial sets of magnets (2232a-p). First intersection point (2262) is disposed on a circumference of a first circle (2274), with a center of first circle (2274) being centerpoint (C). Similarly, second intersection point (2262) is disposed on a circumference of a second circle (2276), with a center of second circle (2276) being centerpoint (C). A third intersection point (2278) measures where line (2258), formed along a second lateral side of magnet (22320), intersects with line (2266), formed along a first lateral side of magnet (2232a).

Magnetic vector directional flow (see FIG. 40) of the magnetic fields is dependent on the concentricity of magnets (2232a-p) within housings (2220). The concentricity of the overall effective vector field is misaligned towards centerpoint (C) of device (2210). For example, this misalignment may be seen in FIGS. 38-39 where first intersection point (2262) is disposed first distance (d1) from centerpoint (C) and second intersection point (2268) is disposed second distance (d2) from centerpoint (C).

Intersecting versus parallel alignment of adjacent magnets (2232a-p) may be controlled by the magnetic intensity and may be amplified by the amount of lateral clearance within housings (2220) for movement of magnets (2232a-p). For example, the stronger the cumulative magnitude of the magnetic field, the more parallel the arrangement of magnets (2232a-p) as generally described above with reference to FIGS. 7-8. Similarly, the weaker the cumulative magnitude of the magnetic field, the more angled the arrangement of magnets (2232a-p). As shown in FIGS. 39-40, the lateral clearance of magnets (2232a-p) within magnet chambers (2226) and the controlled orientation of housings (2220) controls the alignment of the magnetic vectors when in close approximation to create a consistent angular alignment for each magnet (2232a-p) of the annular arrangement. Magnetic vector directional flow of the magnetic fields is dependent on the lateral clearance within housing (2220). The angular orientation of housings (2220) may be obtained by harmonizing the magnetic fields. The size and alignment of the unified inner diameter magnetic field (2270) is proportionate to the gaps (G1, G2) between magnets (2232a-p) and the restraining space within housing (2220).

The adjustment parameter of magnitude of the magnetic fields is shown and described with reference to FIG. 40. The magnitude of the magnetic fields defined between each of adjacent magnets (2232a-p) of the annular arrangement defines a vector field intensity within a predetermined range to maintain the consistent angular orientation.

Magnetic vector directional flow of the magnetic fields is dependent on the equality of the magnet strength of each of adjacent magnets (2232a-p). The magnitude of the magnetic fields is an aspect of the mating adjacent to adjacent magnet surfaces (2250, 2252, 2254, 2256), overall strength, and interfacing features (e.g., the geometry of contact surfaces (2232)) between housings (2220). The magnitude of the magnetic fields (e.g., the magnetic vector directional flow) of adjacent magnets (2232a-p) depends on the equality of the magnetic strength of magnets (2232a-p) to maintain the consistent angular orientation.

As shown in FIG. 40, adjacent magnetic fields include inner and outer diameter magnetic field regions (2270, 2272). Inner and outer diameter magnetic field regions (2270, 2272) are different regions of a single non-uniform magnetic field. Inner diameter magnetic field region (2270) is disposed closer to centerpoint (C) of the annular arrangement than outer diameter magnetic field region (2272). In the contracted configuration of FIG. 40, inner diameter magnetic field region (2270) has a unified magnetic field. Outer diameter magnetic field region (2272) has bifurcated magnetic fields ($R_A$, $R_B$). As shown in FIG. 40, bead-to-bead interactive vector field intensity is related to the resting position distance. The resulting outer diameter magnetic field region (2272) has bifurcated magnetic field aspects compared to the unified inner diameter magnetic field region (2270) extending from the inner diameter toward centerpoint (C) of annular arrangement more than the bifurcated field extends past the outer diameter. Control of the outer diameter bifurcation of the magnetic field through control of the radial orientation of magnets (2232a-p) affects the consistent angular orientation of the annular arrangement.

Figure 41:
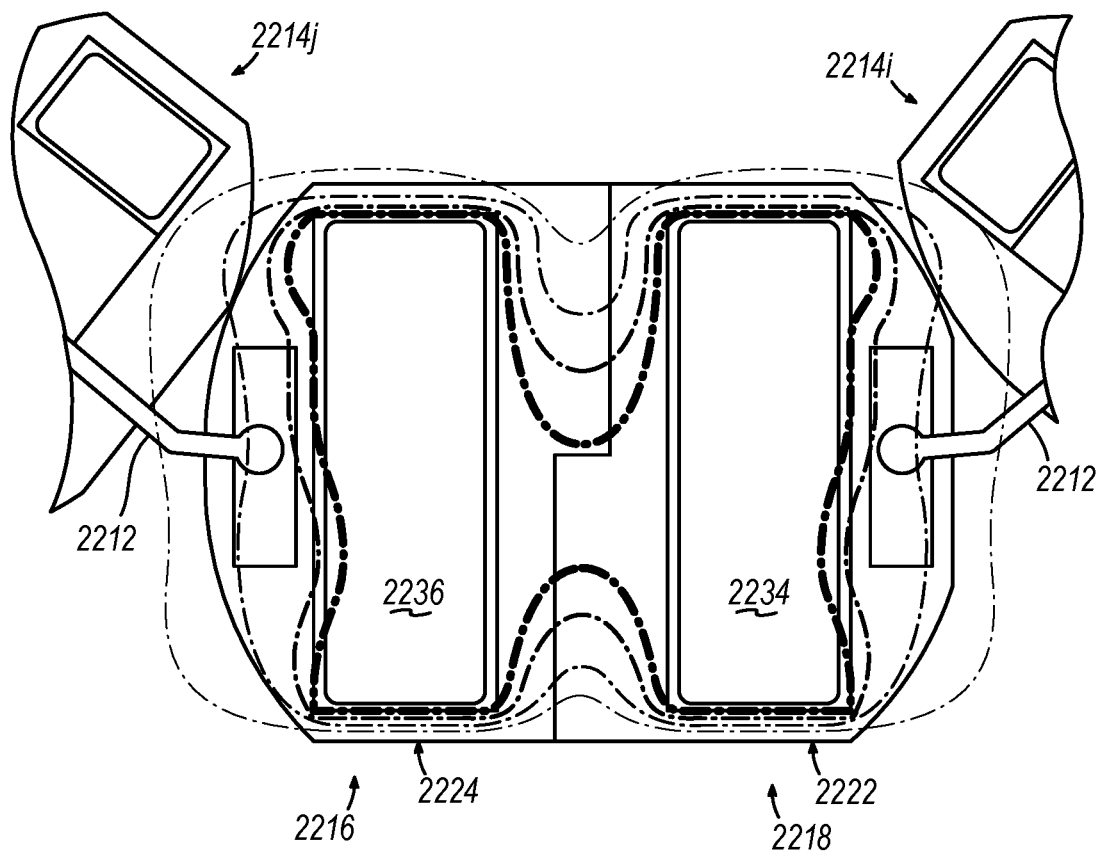
FIG. 41 depicts a partial schematic cross-sectional view of clasping features of the sphincter augmentation device of FIG. 38 generating magnetic fields.

The adjustment parameter of directionality of the adjacent magnets (2232a-p, 2234, 2236) is shown and described with reference to FIGS. 39-41. As shown in FIGS. 40-41, the directionality of magnet (2232a-p) may be affected by twist of magnets (2232a-p) within magnet chamber (2226) which affects the consistent angular orientation. As shown in phantom in FIG. 40, magnet (2232p) may twist within magnet chamber (2226) relative to a plane ($\theta_B$). Similarly, magnet (2232o) may twist within magnet chamber (2226) relative to plane ($\theta_A$).

As shown in FIG. 41, magnets (2234, 2236) of first and second coupling features (2216, 2218) have a uni-axial vector field. Particularly, first and second coupling features (2216, 2218) have a flat-to-flat vector field interaction that produces a significantly more intense and uni-axial vector field of the magnetic attraction forces. The magnetic field in magnets (2234, 2236) aligns due to first and second coupling features (2216, 2218) preventing first and second coupling features (2216, 2218) from articulating with respect to each other. As shown, the magnetic fields are flat and even. Magnets (2234, 2236) of first and second coupling features (2216, 2218) are not shown as including internal apertures (similar to aperture (528) of magnet (118a)); however, magnets (2234, 2236) may include internal apertures.

VIII. EXAMPLES OF COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) at least one link; and (b) a plurality of beads joined using the at least one link and configured to be arranged in an annular arrangement, wherein each bead of the plurality of beads includes at least one magnet, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the magnets are configured to magnetically bias the loop toward the contracted configuration; wherein adjacent beads of the plurality of beads are magnetically attracted together at a plurality of magnetic interfaces that include first and second magnetic interfaces, wherein the first magnetic interface has a first magnetic field strength, wherein the second magnetic interface has a second magnetic field strength that is less than the first magnetic field strength so that the beads forming the second interface are configured to separate prior to the beads forming the first interface when the loop moves from the contracted configuration to the expanded configuration, thereby providing uniform radial expansion of the loop.

Example 2

The apparatus of Example 1, wherein the beads forming the first interface are configured to contact each other prior to the beads forming the second interface when the annular arrangement moves from the expanded configuration to the contracted configuration.

Example 3

The apparatus of any of Examples 1 through 2, wherein the loop is configured to move between the contracted configuration, through an intermediate configuration, and to the expanded configuration, wherein the beads forming the second interface are configured to be spaced apart from each other when the loop is in the intermediate configuration while the beads forming the first interface are configured to remain in abutting contact with each other when the loop is in the intermediate configuration.

Example 4

The apparatus of Example 3, wherein placement of the first and second magnetic interfaces in the annular arrangement is configured to provide uniform radial expansion of the annular arrangement of the plurality of beads as the when the loop is moved from the contracted configuration to the intermediate configuration and from the intermediate configuration to the expanded configuration.

Example 5

The apparatus of any of Examples 3 through 4, wherein the plurality of magnetic interfaces further comprises a third magnetic interface having a third magnetic field strength that is less than the first or second magnetic field strengths, wherein the beads forming the third interface are configured to be spaced apart by a first distance when the loop is in the intermediate configuration, wherein the beads forming the second interface are configured to spaced apart by a second distance when the loop is in the intermediate configuration, wherein the second distance is smaller than the first distance.

Example 6

The apparatus of any of Examples 3 through 4, wherein the plurality of magnetic interfaces include third, fourth, fifth, and sixth magnetic interfaces, wherein the third and fifth magnetic interfaces have the first magnetic field strength, wherein the fourth and sixth magnetic interfaces have the second magnetic field strength, wherein the first, third, and fifth magnetic interfaces are angularly spaced apart from each other around the annular arrangement, wherein the second, fourth, and sixth magnetic interfaces are angularly spaced apart from each other around the annular arrangement.

Example 7

The apparatus of Example 6, wherein the plurality of magnetic interfaces further comprises seventh, eighth, and ninth magnetic interfaces having a third magnetic field strength that is less than the first or second magnetic field strengths, wherein the beads forming the third interface are configured to be spaced apart by a first distance when the loop is in the intermediate configuration, wherein the beads forming the second interface are configured to spaced apart by a second distance when the loop is in the intermediate configuration, wherein the seventh, eighth, and ninth magnetic interfaces are angularly spaced apart from each other around the annular arrangement.

Example 8

The apparatus of any of Examples 1 through 7, wherein the plurality of beads include at least first, second, and third beads, wherein when the loop is in the contracted configuration, the first bead is configured to abut the second bead at the first interface and the second bead is configured to abut the third bead at the second interface, wherein when the loop is in the intermediate configuration, the first and second beads are configured to remain in abutting contact while the second and third beads are configured to be spaced apart from one another, and wherein when the loop is in the expanded configuration, the first bead is configured to be spaced from the second bead and the second bead is configured to be spaced from the third bead.

Example 9

The apparatus of Example 8, further comprising a first magnet received within a first magnet chamber of the first bead, wherein the first magnet chamber is sized and configured to allow for movement of the first magnet within the first magnet chamber, wherein the movement of the first magnet is configured to change the first and second magnetic field strengths of the first interface.

Example 10

The apparatus of Example 9, wherein a second magnet chamber is received within a second magnet chamber of the second bead, wherein the second magnet chamber is sized and configured to allow for movement of the second magnet within the second magnet chamber, wherein the second magnet is configured to move to change the first and second magnetic field strengths of the first and second interfaces.

Example 11

The apparatus of Example 10, wherein the first and second magnets are configured to move to decrease a gap between the first and second magnets.

Example 12

The apparatus of any of Examples 10 through 11, wherein the first and second magnets are configured move to decrease an angle defined between the first and second magnets.

Example 13

The apparatus of any of Examples 8 through 12, wherein at least one of the second or third beads includes an outer coating, wherein the outer coating is configured to reduce the second magnetic field strength relative to the first magnetic field strength.

Example 14

The apparatus of Example 13, wherein each of the second and third beads includes the outer coating, wherein the outer coating of the first bead is thicker than the outer coating of the second bead.

Example 15

The apparatus of any of Examples 1 through 14, wherein each of the plurality of beads comprises: (i) a housing comprising a contact surface, (ii) a passageway extending through the housing, wherein the passageway defines an axis, and (iii) the at least one magnet disposed around the passageway, wherein the at least one magnet comprises at least one annular magnet.

Example 16

An apparatus comprising: (a) at least one link; and (b) a plurality of beads joined using the at least one link and configured to be arranged in an annular arrangement, wherein each of the plurality of beads includes at least one magnet, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the magnets are configured to magnetically bias the loop toward the contracted configuration, wherein adjacent beads of the plurality of beads are magnetically attracted together at a plurality of magnetic interfaces comprising: (i) a first magnetic interface having a first magnetic field strength, (ii) a second magnetic interface having a second magnetic field strength that is less than the first magnetic field strength so that the beads forming the second interface are configured to separate prior to the beads forming the first interface when the loop moves from the contracted configuration to the expanded configuration, (iii) a third magnetic interface having the first magnetic field strength, wherein the first and third magnetic interfaces are angularly spaced apart from each other around the annular arrangement, and (iv) a fourth magnetic interface having the second magnetic field strength, wherein the second and fourth magnetic interfaces are angularly spaced apart from each other around the annular arrangement.

Example 17

The apparatus of Example 16, wherein the plurality of magnetic interfaces further comprises fifth and sixth magnetic interfaces having a third magnetic field strength that is less than the first or second magnetic field strengths, wherein the fifth and sixth magnetic interfaces are angularly spaced apart from each other around the annular arrangement.

Example 18

A method of using an apparatus, the method comprising: (a) coupling an apparatus around an outer surface of a lower esophageal sphincter, the apparatus including a plurality of beads serially joined using at least one link and arranged in an annular arrangement; (b) magnetically attracting together adjacent beads of the plurality of beads at a plurality of magnetic interfaces that include first and second magnetic interfaces, wherein the first magnetic interface has a first magnetic field strength, wherein the second magnetic interface has a second magnetic field strength that is less than the first magnetic field strength; (c) overcoming a magnetic attraction at the second magnetic interface to separate the beads forming the second interface as the annular arrangement moves from a contracted configuration to an intermediate configuration; and (d) overcoming a magnetic attraction at the first magnetic interface after overcoming the magnetic attraction at the second magnetic interface as the annular arrangement moves from the intermediate configuration to an expanded configuration.

Example 19

The method of Example 18, wherein the acts of overcoming the magnetic attractions of the first and second interfaces provides uniform radial expansion of the annular arrangement when moving from the contracted configuration through the intermediate configuration and to the expanded configuration.

Example 20

The method of any of Examples 18 through 19, wherein the plurality of beads includes at least first, second and third beads, wherein the act of overcoming the magnetic attraction at the second magnetic interface further comprises overcoming the magnetic attraction between the first and second beads while not overcoming a magnetic attraction having the first magnetic strength between the second and third beads to provide uniform radial expansion of the annular arrangement when moving from the contracted configuration to the intermediate configuration, and wherein the act of overcoming the magnetic attraction at the first magnetic interface further comprises overcoming the magnetic attraction between the first and second beads after overcoming the magnetic attraction between second and third beads to provide uniform radial expansion of the annular arrangement when moving from the intermediate configuration to the expanded configuration.

Example 21

An apparatus comprising: (a) a plurality of links; and (b) a plurality of beads joined using the plurality of links and configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein each bead comprises: (i) a housing, (ii) a passageway extending through the housing, and (iii) at least one annular magnet disposed around the passageway of the bead, wherein the at least one annular magnet includes an aperture defining a magnet axis, wherein the least one annular magnet of each of the beads is configured to magnetically bias the loop toward the contracted configuration, wherein for at least one of the plurality of beads, the at least one annular magnet comprises a feature configured to concentrate or diffuse a magnetic field interaction of adjacent beads of the plurality of beads toward the magnet axis.

Example 22

The apparatus of Example 21, wherein the feature is configured to diffuse the magnetic field interaction of the adjacent beads away from the magnet axis.

Example 23

The apparatus of any of Examples 21 through 22, wherein the feature comprises a trapezoid cross-sectional shape of the annular magnet, the trapezoid cross-sectional shape being configured to concentrate or diffuse magnetic field interactions of the adjacent beads.

Example 24

The apparatus of any of Examples 21 through 22, wherein the feature comprises a circular cross-sectional shape of the annular magnet, the circular cross-sectional shape being configured to concentrate the magnetic field interactions of the adjacent beads.

Example 25

The apparatus of any of Examples 21 through 24, wherein the feature is configured to induce magnetic pull in at least one predetermined location between the adjacent beads due to the magnetic field interactions of the adjacent beads and shift a focal point of the magnetic field interactions of the adjacent beads to a tunable point between the adjacent beads.

Example 26

The apparatus of any of Examples 21 through 25, wherein for at least one of the plurality of beads, the at least one annular magnet comprises: (A) a first magnet surface, (B) a second magnet surface disposed opposite the first magnet surface, (C) an inner magnet surface disposed between the first and second magnet surfaces, and (D) an outer magnet surface disposed between the first and second magnet surfaces defining an outer perimeter of the annular magnet, wherein at least one of the first magnet surface, the first magnet surface, the inner magnet surface, or the outer the magnet surface includes the feature configured to concentrate or diffuse the magnetic field interactions of the adjacent beads.

Example 27

The apparatus of Example 26, the feature comprising: (A) a first outer chamfered or radiused corner disposed between the first magnet surface and the outer magnet surface, and (B) a second outer chamfered or radiused corner disposed between the second magnet surface and the outer magnet surface.

Example 28

The apparatus of any of Examples 26 through 27, the feature comprising: (A) a first inner chamfered or radiused corner disposed between the first magnet surface and the inner magnet surface, and (B) a second inner chamfered or radiused corner disposed between the second magnet surface and the inner magnet surface.

Example 29

The apparatus of any of Examples 26 through 28, wherein a perimeter shape formed by the first magnet surface, the second magnet surface, the outer magnet surface, and the inner magnet surface is configured to alter the magnetic field interactions of the adjacent beads to control twist between the adjacent beads within and outside externally applied separate magnetic fields.

Example 30

The apparatus of any of Examples 26 through 29, wherein the housing includes a magnet chamber configured to house the at least one annular magnet, the magnet chamber comprising: (A) a first lateral interior surface configured to receive the first magnet surface, (B) a second lateral interior surface disposed opposite the first lateral surface and configured to receive the second magnet surface, (C) an inner interior surface disposed between the first and second lateral surfaces that extends a first length between the first and second lateral interior surfaces, and (D) an outer interior surface disposed between the first and second lateral surfaces and configured to receive the outer magnet surface, wherein the outer interior surface extends a second length between the first and second lateral interior surfaces, wherein the first length is greater than the second length.

Example 31

The apparatus of any of Examples 26 through 30, wherein the feature includes a first groove disposed in at least one of the first and second magnet surfaces between the inner and outer magnet surfaces.

Example 32

The apparatus of Example 31, wherein the first groove is a first annular groove that extends completely within the first magnet surface.

Example 33

The apparatus of Example 32, further comprising a second annular groove that extends completely within the second magnet surface.

Example 34

The apparatus of any of Examples 21 through 29 or Examples 31 through 33, wherein the housing includes a magnet chamber configured to house the at least one annular magnet, wherein a cross-section of the magnet chamber forms a trapezoid, wherein a cross section of the at least one annular magnet forms a trapezoid.

Example 35

The apparatus of any of Examples 21 through 29 or Examples 31 through 33, wherein the housing includes a magnet chamber sized and configured to allow the at least one annular magnet to shift laterally based on a distance to the adjacent bead.

Example 36

An apparatus comprising: (a) a series of beads configured to interconnect to form a loop around an anatomical structure in a patient, wherein the loop is configured to transition between a contracted configuration and an expanded configuration, wherein the loop in the contracted configuration is configured to prevent fluid flow through the anatomical structure, wherein the loop in the expanded configuration is configured to permit fluid flow through the anatomical structure; and (b) at least one annular magnet contained within each bead in the series of beads configured to magnetically bias the loop toward the contracted configuration, the at least one annular magnet comprising: (i) a first magnet surface, (ii) a second magnet surface disposed opposite the first surface, (iii) an inner magnet surface disposed between the first and second magnet surfaces, and (iv) an outer magnet surface disposed between the first and second magnet surfaces defining an outer perimeter of the annular magnet, wherein at least one of the first magnet surface, first magnet surface, the inner magnet surface, or the outer magnet surface includes a feature configured to diffuse magnetic field interactions of adjacent beads moving away from the outer magnet surface.

Example 37

The apparatus of any of Examples 21 through 36, wherein the at least one annular magnet comprises a circular toroid shape configured to induce magnetic pull in at least one predetermined location between the adjacent beads due to the magnetic field interactions of the adjacent beads.

Example 38

The apparatus of any of Examples 21 through 36, wherein the each of the adjacent beads includes a magnet chamber configured to house the at least one annular magnet, wherein a cross-section of the magnet chamber forms a trapezoid.

Example 39

A method of using an apparatus that includes a plurality of beads serially joined together using at least one link, the method comprising: coupling the apparatus around an outer surface of a lower esophageal sphincter, wherein a feature of magnets concentrates or diffuses magnetic field interactions of the magnets of adjacent beads of the plurality of beads after the apparatus is coupled around the outer surface of the lower esophageal sphincter.

Example 40

The method of Example 39, wherein each of the magnets includes an aperture defining a magnet axis, wherein the feature of the magnets concentrates the magnetic field interactions of the magnets of the adjacent beads toward the magnet axis.

Example 41

An apparatus comprising: (a) at least one link; and (b) a plurality of beads joined using the at least one link and configured to be arranged in an annular arrangement, wherein the annular arrangement is sized and configured to form a loop around an anatomical structure in a patient, wherein the annular arrangement is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, each bead of the plurality of beads comprising: (i) a housing, (ii) a magnet contained within the housing, wherein the magnet is configured to emit a magnetic field, wherein the magnets of the plurality of beads are configured to magnetically bias the loop toward the contracted configuration, and (iii) a secondary element that is different from the magnet, wherein the secondary element contained within the housing and is configured to increase the magnetic field of the magnet.

Example 42

The apparatus of Example 41, wherein the magnet has a first size parameter, wherein the secondary element has a second size parameter that is smaller than the first size parameter.

Example 43

The apparatus of Example 42, wherein the first size parameter is a first diameter of the magnet, wherein the second size parameter is a second diameter of the secondary element, wherein the second diameter is less than the first diameter.

Example 44

The apparatus of any of Examples 41 through 43, wherein the secondary element includes a temporary magnet having a high magnetic susceptibility.

Example 45

The apparatus of Example 44, wherein the temporary magnet is not permanently uniaxial.

Example 46

The apparatus of any of Examples 41 through 45, wherein the secondary element includes a permanent magnet magnetically coupled with the magnet.

Example 47

The apparatus of Example 46, wherein the permanent magnet has a uniaxial magnetocrystalline anisotropy.

Example 48

The apparatus of any of Examples 41 through 47, wherein the magnet includes first and second lateral surfaces, wherein the secondary element is in direct contact with at least one of the first and second lateral surfaces.

Example 49

The apparatus of any of Examples 41 through 48, wherein the secondary element includes a first magnetic susceptible metal element configured to direct the magnetic field between adjacent beads of the plurality of beads at a predetermined location.

Example 50

The apparatus of any of Examples 41 through 49, wherein the secondary element is configured to cause the magnetic field to have focus extending high magnetic flux in combination with increased areas of repressed magnetic field strength.

Example 51

The apparatus of any of Examples 41 through 50, wherein the secondary element includes a first ferromagnetic element configured to increase the magnetic field between adjacent beads of the plurality of beads at a predetermined location.

Example 52

The apparatus of Example 51, wherein each of the housings include a contact surface, wherein the predetermined location is the contact surface, wherein the contact surfaces of adjacent beads in the plurality of beads are configured to selectively abut against each other at the contact surface.

Example 53

The apparatus of any of Examples 51 through 52, wherein the secondary element further includes a second ferromagnetic element, wherein the magnet is interposed between the first and second ferromagnetic elements.

Example 54

The apparatus of Example 53, wherein the first and second ferromagnetic elements are magnetically attracted to the magnet and are laterally biased within the housing relative to magnet.

Example 55

The apparatus of any of Examples 53 through 54, wherein the magnet has north and south poles, wherein each of the first and second ferromagnetic elements have north and south poles, wherein the north pole of the first ferromagnetic element is in direct contact with the south pole of the magnet, wherein the south pole of the second ferromagnetic element is in direct contact with the north pole of the magnet.

Example 56

An apparatus comprising: (a) a series of beads configured to be interconnected to form a loop around an anatomical structure in a patient, wherein the loop is configured to transition between a contracted configuration and an expanded configuration, wherein the loop in the contracted configuration is configured to prevent fluid flow through the anatomical structure, wherein the loop in the expanded configuration is configured to permit fluid flow through the anatomical structure; (b) a magnet disposed within each bead in the series of beads and configured to generate a magnetic field to magnetically bias the loop toward the contracted configuration; and (c) a secondary element disposed within each of the beads and configured to increase the magnetic field of the magnet, wherein the secondary element is configured to cause the magnetic field to have

Example 57

The apparatus of any of Examples 41 and Examples 43 through 56, wherein the magnet has a first size parameter, wherein the secondary element has a second size parameter that is smaller than the first size parameter.

Example 58

The apparatus of any of Examples 41 through 50 and Example 56 through 57, wherein the secondary element includes a first ferromagnetic element, the apparatus further comprising a second ferromagnetic element, wherein the magnet is interposed between the first and second ferromagnetic elements, wherein the first and second ferromagnetic elements are magnetically attracted to the magnet.

Example 59

A method of using an apparatus that includes a plurality of beads serially joined via at least one link, the method comprising: coupling the apparatus around an outer surface of a lower esophageal sphincter, wherein each bead of the plurality of beads includes a magnet and a secondary element different from the magnet disposed within each of the beads, wherein the secondary element alters a magnetic field at a contact surface between adjacent beads to direct the magnetic field between the adjacent beads.

Example 60

The method of Example 59, wherein the secondary element includes first and second ferromagnetic elements disposed on first and second lateral sides of the magnet, wherein the first and second ferromagnetic elements alter the magnetic field at a contact surface between the adjacent beads.

Example 61

An apparatus comprising: (a) at least one link; and (b) a plurality of beads joined using the at least one link and configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, each bead of the plurality of beads comprising: (i) a magnet configured to emit a magnetic field, wherein the magnetic fields of adjacent magnets of adjacent beads of the plurality of beads are configured to proportionately change based on a distance between the adjacent beads, wherein the magnet of each of the beads is configured to magnetically bias the loop toward the contracted configuration, and (ii) a non-magnetic feature disposed between the adjacent magnets and configured to create a temporary magnetic braking force by temporarily altering the proportionate change of the magnetic fields once the adjacent beads are in a close proximity state.

Example 62

The apparatus of Example 61, wherein the proportional change of the magnetic fields is based on cooperative engagement of the magnetic fields of the adjacent magnets.

Example 63

The apparatus of any of Examples 61 through 62, wherein the non-magnetic feature is configured to create the temporary magnetic braking force once the adjacent beads are in the close proximity state by reshaping the magnetic fields of the adjacent magnets by inducing electron flow in the non-magnetic feature disposed between the adjacent magnets.

Example 64

The apparatus of any of Examples 61 through 63, wherein the close proximity state is defined by the adjacent magnets being separated by less than a predetermined distance.

Example 65

The apparatus of any of Examples 61 through 64, wherein the non-magnetic feature is configured to create a bimodal distribution in a rate-of-change of the magnetic fields of the adjacent magnets.

Example 66

The apparatus of any of Examples 61 through 65, wherein the magnet includes opposing first and second surfaces, wherein the non-magnetic feature is in direct contact with at least one of the first and second surfaces.

Example 67

The apparatus of any of Examples 61 through 66, wherein the non-magnetic feature includes a first electrically conductive non-ferromagnetic spacer.

Example 68

The apparatus of Example 67, wherein the magnet has a first thickness, wherein the first electrically conductive non-ferromagnetic spacer has a second thickness that is at least half of the first thickness.

Example 69

The apparatus of any of Examples 67 through 68, further comprising a second electrically conductive non-ferromagnetic spacer, wherein the magnet is interposed between the first and second electrically conductive non-ferromagnetic spacers.

Example 70

The apparatus of Example 69, wherein the first and second electrically conductive non-ferromagnetic spacers are in direct contact with the magnet.

focus extending high magnetic flux in combination with increased areas of repressed magnetic field strength.

Example 71

The apparatus of any of Examples 67 through 70, wherein the first electrically conductive non-ferromagnetic spacer includes copper.

Example 72

The apparatus of any of Examples 1 through 17, Examples 21 through 38, Examples 48 through 58, or Examples 61 through 71, wherein each of the beads includes a ferromagnetic surface or sleeve to alter the magnetic field by redirecting magnetic flux.

Example 73

The apparatus of any of Examples 1 through 14, Examples 16 through 17, Examples 36 through 37, Examples 56 through 57, or Examples 61 through 72, wherein each bead includes a housing, wherein the housing includes a magnet chamber configured to house the magnet, wherein the housing includes an outer wall having a non-uniform thickness.

Example 74

The apparatus of any of Examples 61 through 74, wherein the magnet has a first size parameter, wherein the non-magnetic feature has a second size parameter that is smaller than the first size parameter.

Example 75

The apparatus of Example 74, wherein the first size parameter is a first diameter of the magnet, wherein the second size parameter is a second diameter of the non-magnetic feature, wherein the second diameter is smaller than the first diameter.

Example 76

An apparatus comprising: (a) a series of beads configured to interconnect to form a loop around an anatomical structure in a patient, wherein the loop is configured to transition between a contracted configuration and an expanded configuration, wherein the loop in the contracted configuration is configured to prevent fluid flow through the anatomical structure, wherein the loop in the expanded configuration is configured to permit fluid flow through the anatomical structure; (b) a magnet disposed within each bead of the series of beads and configured to generate a magnetic field to magnetically bias the loop toward the contracted configuration, wherein the magnetic fields of adjacent magnets of the beads are configured to proportionately change based on a distance between adjacent beads of the series of beads; and (c) a non-magnetic feature disposed between the adjacent magnets and configured to create a temporary magnetic braking force by temporarily altering the proportionate change of the magnetic fields once the adjacent magnets are in a close proximity state.

Example 77

The apparatus of any of Examples 61 through 66 or Examples 72 through 76, wherein the non-magnetic feature includes a first electrically conductive non-ferromagnetic spacer, wherein the apparatus further comprises a second electrically conductive non-ferromagnetic spacer, wherein the magnet is interposed between the first and second electrically conductive non-ferromagnetic spacers.

Example 78

The apparatus of any of Examples 61 through 67 or Examples 69 through 77, wherein the magnet has a first thickness, wherein the non-magnetic feature has a second thickness that is at least half of the first thickness.

Example 79

A method of using an apparatus that includes a plurality of beads serially joined via at least one link, the method comprising: coupling the apparatus around an outer surface of a lower esophageal sphincter, wherein each bead of the plurality of beads includes a magnet and a non-magnetic element, wherein the non-magnetic feature creates a temporary magnetic braking force to temporarily alter magnetic fields once adjacent magnets of adjacent beads of the plurality of beads are in a close proximity state.

Example 80

The method of Example 79, wherein the non-magnetic feature to induces electron flow to temporarily reshape the magnetic fields of the adjacent magnets.

Example 81

An apparatus comprising: (a) a plurality of links, wherein each link of the plurality of links defines a chord length; and (b) a plurality of beads interconnected together using the plurality of links and configured to be arranged in an annular arrangement, wherein each bead of the plurality of beads includes at least one magnet configured to emit a magnetic field, wherein the annular arrangement is sized and configured to form a loop around an anatomical structure in a patient, wherein the loop is configured to move between a contracted configuration where adjacent beads of the plurality of beads are in contact, and an expanded configuration where the adjacent beads are spaced apart, wherein the loop in the contracted configuration is configured to prevent fluid flow through the anatomical structure, wherein the loop in the expanded configuration is configured to permit fluid flow through the anatomical structure, wherein the magnets are configured to magnetically bias the loop toward the contracted configuration, wherein adjacent magnetic fields of adjacent magnets of the adjacent beads are configured to interact until separated past a minimum threshold in response the annular arrangement moving from the contracted configuration to the expanded configuration, wherein the minimum threshold is based on the chord length of the links.

Example 82

The apparatus of Example 81, wherein an intensity and an angular orientation of the interacting adjacent magnetic fields are based on the chord length of the links.

Example 83

The apparatus of any of Examples 81 through 82, wherein the minimum threshold is at least about half of a contracted width of the magnetic field of the magnets of the adjacent beads in the contracted configuration.

Example 84

The apparatus of Example 83, wherein the contracted width is defined as first and second lines parallel to a portion of the magnetic field where inside and outside collinear surfaces and the contracted width is between the first and second lines.

Example 85

The apparatus of any of Examples 1 through 17, Examples, 41 through 55, Examples 61 through 78, or Examples 81 through 84, wherein the magnets include magnet faces, wherein the magnetic fields between the adjacent beads define an expanded width in the expanded configuration, wherein the expanded width is measured from a vector direction of the magnetic fields that is substantially perpendicular to the magnet faces.

Example 86

The apparatus of Example 85, wherein the vector direction is angled between about 80 degrees and about 90 degrees relative to the magnet faces of the adjacent magnets.

Example 87

The apparatus of any of Examples 81 through 86, wherein the minimum threshold defines a maximum allowable expansion of the annular arrangement while maintaining the magnetic fields of the adjacent magnets.

Example 88

The apparatus of Example 87, wherein a ratio defined by at least one of a shape or an intensity of the adjacent magnetic fields in the expanded configuration relative to at least one of the shape or strength of the adjacent magnetic fields in the contracted configuration is configured to determine the maximum allowable expansion.

Example 89

The apparatus of any of Examples 81 through 88, wherein the minimum threshold based on a maximum length of the link is further based at least in part on an interactive intensity of the adjacent magnetic fields and an angular orientation of the adjacent beads.

Example 90

The apparatus of any of Examples 81 through 89, wherein the minimum threshold is configured to have sufficient cooperative intensity to overcome an expansion force that includes weight of the magnets and friction of the links.

Example 91

The apparatus of any of Examples 1 through 17, Examples 21 through 38, Examples 49 through 52, Examples 61 through 78, or Examples 81 through 90, wherein the magnetic field between the adjacent beads in the contracted configuration is between about 1.5 to about 4 times greater that the magnetic field between the adjacent beads in the expanded configuration.

Example 92

The apparatus of any of Examples 1 through 17, Examples 21 through 38, Examples 49 through 52, Examples 61 through 78, or Examples 81 through 91, wherein the magnetic field between the adjacent beads in the contracted configuration is between about 2 to about 3 times greater that the magnetic field between the adjacent beads in the expanded configuration.

Example 93

The apparatus of any of Examples 1 through 17, Examples 21 through 35, Examples 41 through 55, Examples 61 through 75, or Examples 81 through 92, wherein the adjacent magnetic fields include inner and outer magnetic fields, wherein the inner magnetic field is disposed closer to a center point of the annular arrangement than the outer magnetic field, wherein a first width of the inner magnetic field is greater than a second width of the outer magnetic field.

Example 94

The apparatus of any of Examples 21 through 35 or Examples 81 through 93, wherein each link of the plurality of links includes first and second retention features positioned at opposing terminal ends of the link that mechanically constrain the expanded configuration to prevent further expansion of the annular arrangement beyond the expanded configuration.

Example 95

The apparatus of any of Examples 81 through 94, wherein a minimum full extent magnetic field strength and an X-shaped orientation is proportionate to the chord length of the links.

Example 96

An apparatus comprising: (a) a plurality of links; and (b) a plurality of beads interconnected together using the plurality of links and configured to be arranged in an annular arrangement, wherein each bead of the plurality of beads includes at least one magnet configured to emit a magnetic field, wherein the annular arrangement is sized and configured to form a loop around an anatomical structure in a patient, wherein the loop configured to move between a contracted configuration where adjacent beads of the plurality of beads are in contact, and an expanded configuration where the adjacent beads are spaced apart, wherein the loop in the contracted configuration is configured to prevent fluid flow through the anatomical structure, wherein the loop in the expanded configuration is configured to permit fluid flow through the anatomical structure, wherein the magnets are configured to magnetically bias the loop toward the contracted configuration, wherein adjacent magnetic fields of adjacent magnets of the adjacent beads are configured to interact until separated past a minimum threshold in response the annular arrangement moving from the contracted configuration to the expanded configuration, wherein the minimum threshold is at least about half of a contracted width of the magnetic field of the magnets of the adjacent beads in the contracted configuration.

Example 97

The apparatus of Example 96, wherein the contracted width is defined as first and second lines parallel to a portion of the magnetic field where inside and outside collinear surfaces and the contracted width is between the first and second lines.

Example 98

The apparatus of any of Examples 1 through 17, Examples 41 through 55, Examples 61 through 78, or Examples 81 through 97, wherein the magnets include magnet faces, wherein the magnetic fields between the adjacent beads define an expanded width in the expanded configuration, wherein the expanded width is measured from a vector direction of the magnetic fields that is substantially perpendicular to magnet faces.

Example 99

A method of using an apparatus, the method comprising: coupling the apparatus around an outer surface of a lower esophageal sphincter, the apparatus including a plurality of beads serially joined using a plurality of links and arranged in an annular arrangement, wherein adjacent magnetic fields of adjacent magnets of adjacent beads of the plurality of beads interact until separated past a minimum threshold in response the annular arrangement moving from a contracted configuration to an expanded configuration, wherein the minimum threshold is based on a chord length of the links.

Example 100

The method of Example 99, wherein the minimum threshold is at least about half of a width of the magnetic field of the magnets of the adjacent beads in the contracted configuration Example 101

An apparatus comprising: (a) at least one link; and (b) a plurality of beads joined using the at least one link and configured to be arranged to form an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, each bead of the plurality of beads comprising: (i) a housing that includes a magnet chamber, and (ii) a magnet configured to emit a magnetic field to magnetically bias the loop toward the contracted configuration, wherein the magnet is sized and configured to move within the magnet chamber, wherein a consistent angular orientation of adjacent housings of the plurality of beads in the annular arrangement is determined by at least one of the following adjustment parameters: (A) a magnitude of the magnetic fields of adjacent magnets disposed in the adjacent housings by altering a distance between the adjacent housings, (B) a directionality of the adjacent magnets within adjacent magnet chambers of the plurality of beads by allowing for twist of the magnet within the magnet chamber, or (C) a freedom of the adjacent magnets to move within the adjacent magnet chambers by allowing the magnets to move laterally within the respective magnet chambers.

Example 102

The apparatus of Example 101, wherein the consistent angular orientation of the adjacent housings in the annular arrangement is adjustable by at least two of the following adjustment parameters: (a) the magnitude of the magnetic fields of the adjacent magnets disposed in the adjacent housings by altering a distance between the adjacent housings, (b) the directionality of the adjacent magnets within the adjacent magnet chambers by allowing for twist of the magnet within the magnet chamber, or (c) the freedom of the adjacent magnets to move within the adjacent magnet chambers by allowing the magnets to move laterally within the respective magnet chambers.

Example 103

The apparatus of Example 101, wherein the consistent angular orientation of the adjacent housings in the annular arrangement is adjustable by each of the following adjustment parameters: (a) the magnitude of the magnetic fields of the adjacent magnets disposed in the adjacent housings by altering a distance between the adjacent housings, (b) the directionality of the adjacent magnets within the adjacent magnet chambers by allowing for twist of the magnet within the magnet chamber, or (c) the freedom of the adjacent magnets to move within the adjacent magnet chambers by allowing the magnets to move laterally within the respective magnet chambers.

Example 104

The apparatus of any of Examples 101 through 103, wherein the magnitude of the magnetic fields between each of the adjacent magnets defines a vector field intensity that is within a predetermined range to maintain the consistent angular orientation.

Example 105

The apparatus of any of Examples 101 through 104, wherein the freedom of the magnets to move within the adjacent magnet chambers includes lateral movement of the magnets along first and second directions that separated by about 90 degrees to maintain the consistent angular orientation.

Example 106

The apparatus of any of Examples 101 through 105, wherein the magnet is configured to twist within the magnet chamber to change the directionality of the magnet to maintain the consistent angular orientation.

Example 107

The apparatus of any of Examples 101 through 106, wherein the consistent angular orientation is measured by intersection points between each of the adjacent magnets, wherein each of the intersection points is within a predetermined range to maintain the consistent angular orientation.

Example 108

The apparatus of any of Examples 1 through 17, Examples 21 through 35, Examples 41 through 55, Examples 61 through 75, Examples 81 through 98, or Examples 101 through 107, wherein the annular arrangement has a center, wherein the magnets are configured to be misaligned towards the center of the annular arrangement.

Example 109

The apparatus of any of Examples 101 through 108, wherein the plurality of beads includes first, second, and third beads, wherein lines parallel to lateral sides of the magnets of the first and second beads are configured to intersect at a first intersection point that is a first distance from a center of the annular arrangement, wherein lines parallel to adjacent lateral sides of the magnets of the second and third beads are configured to intersect at a second intersection point that is a second distance from the center of the annular arrangement, wherein the first and second distances are different.

Example 110

The apparatus of any of Examples 101 through 109, wherein the magnitude of the magnetic fields is dependent upon a distance between adjacent magnet faces of the adjacent magnets, an overall magnetic strength of the adjacent magnets, and interfacing features between the housings.

Example 111

The apparatus of any of Examples 101 through 110, wherein the magnitude of the magnetic fields of the adjacent magnets depends on equality in individual magnetic strength of the adjacent magnets to maintain the consistent angular orientation of the annular arrangement.

Example 112

The apparatus of any of Examples 101 through 111, the magnet chamber comprising: (A) a first lateral interior surface, and (B) a second lateral interior surface disposed opposite the first lateral interior surface, wherein the magnet is configured to move laterally within the magnet chamber between the first and second lateral interior surfaces to maintain the consistent angular orientation.

Example 113

The apparatus of any of Examples 101 through 112, the magnet chamber comprising: (A) an inner interior surface disposed between the first and second lateral interior surfaces, and (B) an outer interior surface disposed between the first and second lateral interior surfaces and opposite to the inner interior surface, wherein the magnet is configured to move laterally within the magnet chamber between the inner and outer interior surfaces to maintain the consistent angular orientation.

Example 114

The apparatus of any of Examples 101 through 113, wherein adjacent magnetic fields of the adjacent magnets include inner and outer magnetic field regions, wherein the inner magnetic field region is disposed closer to a center point of the annular arrangement than the outer magnetic field region, wherein in the contracted configuration: (a) the inner magnetic field region has a unified magnetic field, and (b) the outer magnetic field region has a bifurcated magnetic field.

Example 115

The apparatus of any of Examples 101 through 114, further comprising: (a) a first coupling feature that includes a magnet; and (b) a second coupling feature configured to selectively couple with the first coupling feature to secure the apparatus in the annular arrangement, wherein the second coupling feature includes a magnet, wherein the magnets of the first and second coupling features have a uni-axial vector field.

Example 116

An apparatus comprising: (a) at least one link; and (b) a plurality of beads joined using the at least one link and configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, each bead of the plurality of beads comprising: (i) a housing that includes a magnet chamber, and (ii) a magnet configured to emit a magnetic field to magnetically bias the loop toward the contracted configuration, wherein a consistent angular orientation of adjacent housings of the plurality of beads in the annular arrangement is determined by each of the following adjustment parameters: (A) a directionality of the adjacent magnets within adjacent magnet chambers of the plurality of beads by allowing for twist of the magnet within the magnet chamber, and (B) a freedom of the adjacent magnets to move within the adjacent magnet chambers by allowing the magnets to move laterally within the respective magnet chambers.

Example 117

The apparatus of any of Examples 101 through 116, wherein each of the housings includes a contact surface, wherein the contact surfaces of the adjacent housings are configured to abut against each other in the contracted configuration at the consistent angular orientation.

Example 118

The apparatus of any of Examples 101 through 111 or Examples 114 through 117, the magnet chamber comprising: (A) an inner interior surface disposed between the first and second lateral interior surfaces, and (B) an outer interior surface disposed between the first and second lateral interior surfaces and opposite to the inner interior surface, wherein the magnet is configured to move laterally within the magnet chamber between the inner and outer interior surfaces to maintain the consistent angular orientation.

Example 119

A method of using an apparatus including a plurality of beads serially joined via at least one link, the method comprising: coupling the apparatus around an outer surface of a lower esophageal sphincter, the apparatus forming an annular arrangement around the lower esophageal sphincter, wherein adjacent housings of the plurality of beads in the annular arrangement maintain a consistent angular orientation using at least one of the following adjustment parameters: (a) a magnitude of magnetic fields of adjacent magnets disposed in the adjacent housings by altering a distance between the adjacent housings, (b) a directionality of the adjacent magnets within adjacent magnet chambers of the plurality of beads by allowing for twist of the magnet within the magnet chamber, or (c) a freedom of the adjacent magnets to move within the adjacent magnet chambers by allowing the magnets to move laterally within the respective magnet chambers.

Example 120

The method of Example 119, wherein the annular arrangement has a center, wherein the magnets are misaligned towards the center of the annular arrangement.

IX. MISCELLANEOUS

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
(a) at least one link; and
(b) a plurality of beads joined using the at least one link and configured to be arranged in an annular arrangement, wherein the annular arrangement is sized and configured to form a loop around an anatomical structure in a patient, wherein the annular arrangement is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, each bead of the plurality of beads comprising:
(i) a housing,
(ii) a magnet contained within the housing, wherein the magnet is configured to emit a magnetic field, wherein the magnets of the plurality of beads are configured to magnetically bias the loop toward the contracted configuration, and
(iii) a secondary element that is different from the magnet, wherein the secondary element contained within the housing and is configured to increase the magnetic field of the magnet.

2. The apparatus of claim 1, wherein the magnet has a first size parameter, wherein the secondary element has a second size parameter that is smaller than the first size parameter.

3. The apparatus of claim 2, wherein the first size parameter is a first diameter of the magnet, wherein the second size parameter is a second diameter of the secondary element, wherein the second diameter is less than the first diameter.

4. The apparatus of claim 1, wherein the secondary element includes a temporary magnet having a high magnetic susceptibility.

5. The apparatus of claim 4, wherein the temporary magnet is not permanently uniaxial.

6. The apparatus of claim 1, wherein the secondary element includes a permanent magnet magnetically coupled with the magnet.

7. The apparatus of claim 6, wherein the permanent magnet has a uniaxial magnetocrystalline anisotropy.

8. The apparatus of claim 1, wherein the magnet includes first and second lateral surfaces, wherein the secondary element is in direct contact with at least one of the first and second lateral surfaces.

9. The apparatus of claim 1, wherein the secondary element includes a first magnetic susceptible metal element configured to direct the magnetic field between adjacent beads of the plurality of beads at a predetermined location.

10. The apparatus of claim 1, wherein the secondary element is configured to cause the magnetic field to have focus extending high magnetic flux in combination with increased areas of repressed magnetic field strength.

11. The apparatus of claim 1, wherein the secondary element includes a first ferromagnetic element configured to increase the magnetic field between adjacent beads of the plurality of beads at a predetermined location.

12. The apparatus of claim 11, wherein each of the housings include a contact surface, wherein the predetermined location is the contact surface, wherein the contact surfaces of adjacent beads in the plurality of beads are configured to selectively abut against each other at the contact surface.

13. The apparatus of claim 11, wherein the secondary element further includes a second ferromagnetic element, wherein the magnet is interposed between the first and second ferromagnetic elements.

14. The apparatus of claim 13, wherein the first and second ferromagnetic elements are magnetically attracted to the magnet and are laterally biased within the housing relative to magnet.

15. The apparatus of claim 13, wherein the magnet has north and south poles, wherein each of the first and second ferromagnetic elements have north and south poles, wherein the north pole of the first ferromagnetic element is in direct contact with the south pole of the magnet, wherein the south pole of the second ferromagnetic element is in direct contact with the north pole of the magnet.

16. An apparatus comprising:
(a) a series of beads configured to be interconnected to form a loop around an anatomical structure in a patient, wherein the loop is configured to transition between a contracted configuration and an expanded configuration, wherein the loop in the contracted configuration is configured to prevent fluid flow through the anatomical structure, wherein the loop in the expanded configuration is configured to permit fluid flow through the anatomical structure;
(b) a magnet disposed within each bead in the series of beads and configured to generate a magnetic field to magnetically bias the loop toward the contracted configuration; and
(c) a secondary element disposed within each of the beads and configured to increase the magnetic field of the magnet, wherein the secondary element is configured to cause the magnetic field to have focus extending high magnetic flux in combination with increased areas of repressed magnetic field strength.

17. The apparatus of claim 16, wherein the magnet has a first size parameter, wherein the secondary element has a second size parameter that is smaller than the first size parameter.

18. The apparatus of claim 16, wherein the secondary element includes a first ferromagnetic element, the apparatus further comprising a second ferromagnetic element, wherein the magnet is interposed between the first and second ferromagnetic elements, wherein the first and second ferromagnetic elements are magnetically attracted to the magnet.

* * * * *